US011808767B2

(12) United States Patent
Chiu et al.

(10) Patent No.: US 11,808,767 B2
(45) Date of Patent: Nov. 7, 2023

(54) METHODS, COMPOSITIONS AND SYSTEMS FOR MICROFLUIDIC ASSAYS

(71) Applicant: UNIVERSITY OF WASHINGTON THROUGH ITS CENTER FOR COMMERCIALIZATION, Seattle, WA (US)

(72) Inventors: Daniel T. Chiu, Seattle, WA (US); Mengxia Zhao, Seattle, WA (US); Wyatt Nelson, Seattle, WA (US); Perry G. Schiro, Seattle, WA (US)

(73) Assignee: UNIVERSITY OF WASHINGTON THROUGH ITS CENTER FOR COMMERCIALIZATION, Seattle, WA (US)

(*) Notice: Subject to any disclaimer, the term of this patent is extended or adjusted under 35 U.S.C. 154(b) by 0 days.

(21) Appl. No.: 17/932,687

(22) Filed: Sep. 16, 2022

(65) Prior Publication Data

US 2023/0023536 A1 Jan. 26, 2023

Related U.S. Application Data

(63) Continuation of application No. 16/702,176, filed on Dec. 3, 2019, now Pat. No. 11,480,575, which is a
(Continued)

(51) Int. Cl.
*G01N 33/574* (2006.01)
*B01L 3/00* (2006.01)
(Continued)

(52) U.S. Cl.
CPC .. *G01N 33/57492* (2013.01); *B01L 3/502761* (2013.01); *B01L 3/561* (2013.01);
(Continued)

(58) Field of Classification Search
CPC ............ G01N 33/57492; G01N 33/49; G01N 33/5304; G01N 15/0612; G01N 15/1456;
(Continued)

(56) References Cited

U.S. PATENT DOCUMENTS 5,602,042 A 2/1997 Farber
6,150,173 A 11/2000 Schubert
(Continued)

FOREIGN PATENT DOCUMENTS

CN 102015998 A 4/2011
JP S6182168 A 4/1986
(Continued)

OTHER PUBLICATIONS

Yu et al., "Circulating breast tumor cells exhibit dynamic changes in epithelial and mesenchymal composition," Science, 339(6119):580-584, doi: 10.1126/science.1228522, Feb. 2013.
(Continued)

*Primary Examiner* — Jennifer Wecker
*Assistant Examiner* — Kathryn Elizabeth Limbaugh
(74) *Attorney, Agent, or Firm* — Christensen O'Connor Johnson Kindness PLLC

(57) ABSTRACT

Provided herein, among other aspects, are methods and apparatuses for analyzing particles in a sample. In some aspects, the particles can be analytes, cells, nucleic acids, or proteins and contacted with a tag, partitioned into aliquots, detected by a ranking device, and isolated. The methods and apparatuses provided herein may include a microfluidic chip. In some aspects, the methods and apparatuses may be used to quantify rare particles in a sample, such as cancer cells and other rare cells for disease diagnosis, prognosis, or treatment.

20 Claims, 26 Drawing Sheets

Related U.S. Application Data continuation of application No. 14/903,012, filed as application No. PCT/US2014/045094 on Jul. 1, 2014, now Pat. No. 10,527,626.

(60) Provisional application No. 61/894,788, filed on Oct. 23, 2013, provisional application No. 61/843,252, filed on Jul. 5, 2013.

(51) Int. Cl.

| | |
|---|---|
| *G01N 15/06* | (2006.01) |
| *G01N 15/14* | (2006.01) |
| *G01N 33/49* | (2006.01) |
| *G01N 21/64* | (2006.01) |
| *G01N 33/53* | (2006.01) |
| *G01N 35/10* | (2006.01) |
| *G01N 35/00* | (2006.01) |
| *G01N 15/10* | (2006.01) |

(52) U.S. Cl.
CPC .......... *B01L 3/567* (2013.01); *G01N 15/0612* (2013.01); *G01N 15/0656* (2013.01); *G01N 15/1456* (2013.01); *G01N 15/1484* (2013.01); *G01N 21/6428* (2013.01); *G01N 21/6456* (2013.01); *G01N 33/49* (2013.01); *G01N 33/5304* (2013.01); *B01L 3/502738* (2013.01); *B01L 3/502776* (2013.01); *B01L 2200/0652* (2013.01); *B01L 2200/0668* (2013.01); *B01L 2200/0673* (2013.01); *B01L 2200/10* (2013.01); *B01L 2300/0636* (2013.01); *B01L 2300/0681* (2013.01); *B01L 2300/0816* (2013.01); *B01L 2300/0832* (2013.01); *B01L 2300/0864* (2013.01); *B01L 2300/0883* (2013.01); *B01L 2400/0406* (2013.01); *B01L 2400/0415* (2013.01); *B01L 2400/0487* (2013.01); *B01L 2400/06* (2013.01); *B01L 2400/0633* (2013.01); *B01L 2400/086* (2013.01); *G01N 15/0618* (2013.01); *G01N 35/0098* (2013.01); *G01N 2015/0681* (2013.01); *G01N 2015/0693* (2013.01); *G01N 2015/1006* (2013.01); *G01N 2015/149* (2013.01); *G01N 2035/00237* (2013.01); *G01N 2035/00356* (2013.01); *G01N 2035/1034* (2013.01)

(58) Field of Classification Search
CPC .......... G01N 15/1484; G01N 15/0618; G01N 21/6428; G01N 21/6456; G01N 35/0098; G01N 2015/0681; G01N 2015/0693; G01N 2015/1006; G01N 2015/149; G01N 2035/00237; G01N 2035/00356; G01N 2035/1034; B01L 3/502761; B01L 3/561; B01L 3/567; B01L 3/502738; B01L 3/502776; B01L 2200/0652; B01L 2200/0668; B01L 2200/0673; B01L 2200/10; B01L 2300/0636; B01L 2300/0681; B01L 2300/0816; B01L 2300/0832; B01L 2300/0864; B01L 2300/0883; B01L 2400/0406; B01L 2400/0415; B01L 2400/0487; B01L 2400/06; B01L 2400/0633; B01L 2400/086
See application file for complete search history.

(56) References Cited

U.S. PATENT DOCUMENTS

| | | |
|---|---|---|
| 6,365,362 B1 | 4/2002 | Terstappen et al. |
| 7,745,221 B2 | 6/2010 | Butler et al. |
| 2002/0037499 A1 | 3/2002 | Quake et al. |
| 2002/0081569 A1 | 6/2002 | Anderson |
| 2003/0175980 A1 | 9/2003 | Hayenga et al. |
| 2003/0232425 A1 | 12/2003 | Bachalo et al. |
| 2004/0072278 A1 | 4/2004 | Chou et al. |
| 2005/0103690 A1 | 5/2005 | Kawano et al. |
| 2006/0078888 A1 | 4/2006 | Griffiths et al. |
| 2006/0266679 A1 | 11/2006 | Bohm et al. |
| 2007/0025883 A1 | 2/2007 | Tai et al. |
| 2007/0037172 A1 | 2/2007 | Chiu et al. |
| 2007/0172954 A1 | 7/2007 | Ismagilov et al. |
| 2008/0003142 A1 | 1/2008 | Link et al. |
| 2008/0145286 A1 | 6/2008 | Maltezos et al. |
| 2008/0163946 A1 | 7/2008 | Gomez et al. |
| 2008/0248499 A1 | 10/2008 | Chiu et al. |
| 2008/0261295 A1 | 10/2008 | Butler et al. |
| 2008/0318324 A1 | 12/2008 | Chiu et al. |
| 2009/0014360 A1 | 1/2009 | Mehmet et al. |
| 2009/0035838 A1 | 2/2009 | Quake et al. |
| 2010/0003666 A1 | 1/2010 | Lee et al. |
| 2010/0055766 A1 | 3/2010 | Hwang et al. |
| 2010/0279321 A1 | 11/2010 | Chiu et al. |
| 2012/0015347 A1 | 1/2012 | Singhal et al. |
| 2012/0129190 A1 | 5/2012 | Chiu et al. |
| 2013/0078163 A1 | 3/2013 | Chung et al. |
| 2014/0073042 A1 | 3/2014 | Igata |

FOREIGN PATENT DOCUMENTS

| | | |
|---|---|---|
| JP | 2003-294604 A | 10/2003 |
| JP | 2005-134372 A | 5/2005 |
| JP | 2005-245317 A | 9/2005 |
| JP | 2007-209910 A | 8/2007 |
| JP | 2008-516251 A | 5/2008 |
| JP | 2009-063375 A | 3/2009 |
| JP | 2009-066512 A | 4/2009 |
| JP | 2010525325 A | 7/2010 |
| JP | 2012120542 A | 6/2012 |
| JP | 2012523572 A | 10/2012 |
| JP | 2012-528329 A | 11/2012 |
| JP | 2012-255810 A | 12/2012 |
| JP | 2012237607 A | 12/2012 |
| KR | 20050047540 A | 5/2005 |
| TW | 574130 B | 2/2004 |
| WO | 02/097122 A1 | 12/2002 |
| WO | 2006/110855 A2 | 10/2006 |
| WO | 2007/081387 A1 | 7/2007 |
| WO | 2008/130871 A2 | 10/2008 |
| WO | 2009/128948 A1 | 10/2009 |
| WO | 2010/120818 A2 | 10/2010 |
| WO | 2011/063416 A2 | 5/2011 |
| WO | 2012/162779 A1 | 12/2012 |
| WO | 2015/002975 A1 | 1/2015 |
| WO | 2006/067715 A2 | 6/2016 |

OTHER PUBLICATIONS

Zabaglo et al., "Cell filtration-laser scanning cytometry for the characterization of circulating breast cancer cells," Cytometry Part A, 55A(2):102-108, 2003.

Zhang, "The introduction of the flow cytometer. Construction and Working Principles of Flow Cytometer," Information of Medical Equipment, 20(8):25-26, Aug. 31, 2005 (in Chinese with English abstract).

Zhao et al., "Flow cytometry. Principles and Methods for Histiocyte Molecular Experiment," China Press of Traditional Chinese Medicine, pp. 324-327, Sep. 30, 2003 (in Chinese with English translation).

Zhao et al., "An automated high-throughput counting method for screening circulating tumor cells in peripheral blood," Anal Chem., 85(4):2465-2471, doi: 10.1021/ac400193b, Feb. 2013.

(56) References Cited

OTHER PUBLICATIONS

Zhao et al., "Imaging multiple biomarkers in captured rare cells by sequential immunostaining and photobleaching," Methods, 64(2):108-113, doi: 10.1016/j.ymeth.2013.08.006, Dec. 2013 (epublished Aug. 2013).
Zhao et al., "Method for the accurate preparation of cell-spiking standards," Anal Chem., 81(3):1285-1290, doi: 10.1021/ac802250d, Feb. 2009.
Zheng et al., "Membrane microfilter device for selective capture, electrolysis and genomic analysis of human circulating tumor cells," J Chromatogr A, 1162(2):154-161, Aug. 2007 (epublished May 2007).
Zieglschmid et al., "Detection of disseminated tumor cells in peripheral blood," Crit Rev Clin Lab Sci., 42(2):155-196, 2005.
Office Action dated Nov. 17, 2016 for CN Application No. 201480048902.
Extended European Search Report and Search Opinion dated Dec. 13, 2017 for European Patent Application No. EP17187038.9.
Office Action dated Jan. 4, 2017, for CA Application No. 2,758,382.
Office Action dated Mar. 23, 2017 for U.S. Appl. No. 13/257,571.
Office Action dated Jun. 16, 2017 for CN Application No. 201510585927.
Office Action dated Jun. 29, 2017 for U.S. Appl. No. 13/257,571.
Office Action dated Aug. 16, 2017 for CN Application No. 201480048902.0.
Office Action dated Aug. 30, 2016 for CN Application No. 201510585927.0.
Office Action dated Sep. 14, 2017 for JP Application No. 2017-18205.
Office Action dated Oct. 19, 2017 for CN Application No. 201510585927.0.
Office Action dated Nov. 10, 2016 for AU Application No. 2015234379.
Office Action dated Nov. 21, 2017 for KR Application No. KR-2011-7027042.
Office Action dated Jan. 23, 2018 for TW Application No. 103123208.
Office Action dated Feb. 13, 2018 for U.S. Appl. No. 13/257,571.
Supplementary European Search Report and Opinion dated Mar. 24, 2017 for EP Application No. 14819852.6.
Kruger et al., "Development of a microfluidic device for fluorescence activated cell sorting," Journal of Micromechanics and Microengineering, 12:486-494, 2002.
Third Office Action dated May 3, 2018, for CN 201480048902.0 (w/ English translation).
Schiro et al., "Sensitive and high-throughput isolation of rare cells from peripheral blood with ensemble-decision aliquot ranking," Angew Chem Int. Ed Engl., 51(19):4618-4622, doi:10.1002/anie.201108695. May 2012 (epublished Feb. 2012), with Supporting Information, total 17 pages.
Office Action dated May 11, 2018, for JP 201718205 (with English translation).
Office Action dated Jul. 30, 2018 for U.S. Appl. No. 13/257,571.
Allen et al., "Pressure-driven laminar flow switching for rapid exchange of solution environment around surface adhered biological particles," Lab Chip, 10(6):727-733, doi: 10.1039/b919639k, Mar. 2010 (epublished Jan. 2010).
Office Action dated Jan. 29, 2019 for U.S. Appl. No. 13/257,571.
Office Action dated Jan. 21, 2019 for JP Application No. 2017-018205.
Office Action dated Jan. 22, 2019 for EP Application No. 17187038.9.
Fourth Office Action dated Apr. 22, 2019, issued in corresponding Chinese Patent Application No. 201480048902.0, filed Jul. 1, 2014, 9 pages.
Office Action for Taiwan Patent Application No. 103123208, dated Jul. 24, 2019, with English Translation, 9 pages.
Notice of Reasons for Refusal dated Feb. 4, 2022, issued in corresponding Japanese Application No. 2021-22510, filed Jul. 1, 2014, 4 pages.
Wiodkowic, D., et al., "Microfluidic Single Cell Array Cytometry for the Analysis of Tumour Apoptosis," Anal Chem. Jul. 1, 2009; 81(13), 16 pages.
Kobel, S., et al., "Optimization of Microfluidic Single Cell Trapping for Long-term On-chip Culture," Lab on a Chip, 2010, vol. 10, No. 7, p. 857-863.
Notice of Reasons for Rejection dated Jun. 26, 2020, issued in corresponding Divisional Japanese Application No. 2019-123063, filed Jul. 1, 2014, 7 pages.
Communication Pursuant to Article 94(3) EPC, European Office Action dated Jul. 6, 2021, in corresponding European Patent Application No. 14819852.6, 8 pages.
Denial of Entry of Amendment dated Jun. 25, 2021. in Japanese Patent Application No. 2019-123063. 5 pages (includes English translation).
Notice of Final Rejection dated Jun. 25, 2021, in Japanese Patent Application No. 2019-123063, 4 pages (includes English translation).
Penultimate Office Action dated Mar. 5, 2021, in corresponding Japanese Application No. 2019-123063, 7 pages.
Schiro P.G. et al., "Sensitive and High-Throughput Isolation of Rare Cells from Peripheral Blood with Ensemble-Decision Aliquot Ranking", Angew Chem Int Ed Engl. May 7, 2012;51(19):4618-22.
First Chinese Office Action dated Jan. 28, 2023, issued in corresponding Chinese App. No. 201911089720.9, filed on Jul. 1, 2014, and its English translation thereof.
Bode et al., "Toponome imaging system (TIS): imaging the proteome with functional resolution," Nature Methods, iii-iv, Jan. 2007.
Evans et al., "Toponome imaging system: multiplex biomarkers in oncology," Trends Mol 18(12):723-731, doi: 10.1016/j.molmed.2012.10.003, Dec. 2012 (epublished Nov. 2012).
International Search Report and Written Opinion dated Nov. 7, 2014 for PCT/US2014/045094.
Schubert et al., "Toponome mapping in prostate cancer: detection of 2000 cell surface protein clusters in a single tissue section and cell type specific annotation by using a three symbol code," J Proteome Res, 8(6):2696-2707, doi: 10.1021/pr800944f, Jun. 2009.
Schubert, "A three-symbol code for organized proteomes based on cyclical imaging of protein locations," Cytometry A, 71(6):352-360, Jun. 2007.
Schubert, "Exploring molecular networks directly in the cell," Cytometry A, 69(3):109-112, Mar. 2006.
Schubert, "Multiple antigen mapping microscopy of human tissue," in Advances in Analytical Cellular Pathology, Excerpta Medica, eds. G. Burger et al., Elsevier: Amsterdam, pp. 97-98, 1990.
Adams et al., "Highly efficient circulating tumor cell isolation from whole blood and label-free enumeration using polymer-based microfluidics with an integrated conductivity sensor," J Am Chem Soc, 130(27):8633-8641, doi: 10.1021/ja8015022, Jul. 2008 (epublished Jun. 2008).
Adams et al., "Integrated acoustic and magnetic separation in microfluidic channels," Appl Phys Lett, 95(25):254103, Dec. 2009.
Aktas et al., "Stem cell and epithelial-mesenchymal transition markers are frequently overexpressed in circulating tumor cells of metastatic breast cancer patients," Breast Cancer Res, 11(4):R46, doi:10.1186/bcr2333, 2009 (epublished Jul. 2009).
Al-Hajj et al., "Prospective identification of tumorigenic breast cancer cells," Proc Natl Acad Sci USA, 100(7):3983-3988, Apr. 2003 (epublished Mar. 2003).
Allard et al., "Tumor cells circulate in tlle peripheral blood of all major carcinomas but not in healthy subjects or patients with nonmalignant diseases," Clin Cancer Res, 10(20):6897-6904, Oct. 2004.
Alsalameh et al., "Identification of mesenchymal progenitor cells in normal and osteoarthritic human articular cartilage," Arthritis Rheum, 50(5):1522-1532, May 2004.
Alunni-Fabbroni et al., "Circulating tumour cells in clinical practice: Methods of detection and possible characterization," Methods, 50(4):289-297, doi: 10.1016/j.ymeth.2010.01.027, Apr. 2010 (epublished Jan. 2010 Review).
Andreopoulou et al., "Circulating tumor cells as prognostic marker in metastatic breast cancer," Expert Rev Anticancer Ther, 10(2):171-177. doi: 10.1586/era.09.105, Feb. 2010.

(56) References Cited

OTHER PUBLICATIONS

Aurilio et al., "Prognostic value of circulating tumor cells in primary and metastatic breast cancer," Expert Rev Anticancer Ther, 12(2):203-214, doi:10.1586/era.11.208, Feb. 2012.

Balasubramanian et al., "Confocal images of circulating tumor cells obtained using a methodology and technology that removes normal cells," Mol Pharm, 6(5):1402-1408, doi: 10.1021/mp9000519, Sep.-Oct. 2009.

Balasubramanian et al., "β3 integrin in cardiac fibroblast is critical for extracellular matrix accumulation during pressure overload hypertrophy in mouse," PLoS One, 7(9):e45076, doi: 10.1371/journal.pone.0045076, 2012 (epublished Sep. 2012).

Chaffer et al., "A perspective on cancer cell metastasis," Science, 331(6024):1559-1564, doi: 10.1126/science.1203543, Mar. 2011.

Cohen et al., "Relationship of circulating tumor cells to tumor response, progression-free survival, and overall survival in patients with metastatic colorectal cancer," J Clin Oncol, 26(19):3213-3221, doi: 10.1200/JC0.2007.15.8923, Jul. 2008.

Cristofanilli et al., "Circulating tumor cells in breast cancer: Advanced tools for "tailored" therapy?" Proc Natl Acad Sci USA, 103(46):17073-17074, Nov. 2006 (epublished Nov. 2006).

Cristofanilli et al., "Circulating tumor cells, disease progression, and survival in metastatic breast cancer," N Engl J Med, 351(8):781-791, Aug. 2004.

Danila et al., "Circulating tumor cells as biomarkers in prostate cancer," Clin Cancer Res, 17(12):3903-3912, doi: 10.1158/1078-0432.CCR-10-2650, Jun. 2011.

De Bono et al., "Translating cancer research into targeted therapeutics," Nature, 467(7315):543-549, doi: 10.1038/nature09339, Sep. 2010.

Dharmasiri et al., "High-throughput selection, enumeration, electrokinetic manipulation, and molecular profiling of low-abundance circulating tumor cells using a microfluidic system," Anal Chem, 83(6):2301-2309, doi: 10.1021/acl03172y, Mar. 2011 (epublished Feb. 2011).

Dharmasiri et al., "Microsystems for the capture of low-abundance cells," Annu Rev Anal Chem (Palo Alto Calif), 3:409-431, doi: 10.1146/annurev.anchem.111808.073610, 2010.

Edgar et al., "Compartmentalization of chemically separated components into droplets," Angew Chem Int Ed Engl, 48(15):2719-2722, doi: 10.1002/anie.200805396, 2009.

European office action dated Sep. 27, 2016, for EP Application No. 15188512.6.

European search report dated Sep. 6, 2012, for EP Application No. 10765047.5.

European search report dated Dec. 10, 2015, for EP Application No. 15188512.6.

Fidler, "The pathogenesis of cancer metastasis: the 'seed and soil' hypothesis revisited," Nat Rev Cancer, 3(6):453-458, Jun. 2003.

Fiorini et al., "Disposable microfluidic devices: fabrication, function, and application," Biotechniques, 38(3):429-446, Mar. 2005.

Fokas et al., "Metastasis: the seed and soil theory gains identity." Cancer Metastasis Rev, 26(3-4):705-715, Dec. 2007.

Friel et al., "Relevance of circulating tumor cells, extracellular nucleic acids, and exosomes in breast cancer," Breast Cancer Res Treat, 123(3):613-625, doi: 10.1007/s10549-010-0980-2, Oct. 2010 (epublished Jun. 2010).

Goda et al., "High-throughput single-microparticle imaging flow analyzer," Proc Natl Acad Sci USA, 109(29):11630-11635, doi: 10.1073/pnas.1204718109, Jul. 2012 (epublished Jul. 2012).

Gorges et al., "Circulating tumour cells escape from EpCAM-based detection due to epithelial-to-mesenchymal transition," BMC Cancer, 12:178, doi: 10.1186/1471-2407-12-178, May 2012.

Gossett et al., "Label-free cell separation and sorting in microfluidic systems," Anal Bioanal Chem, 397(8):3249-3267, doi: 10.1007/s00216-010-3721-9, Aug. 2010 (epublished Apr. 2010).

Gross et al., "Detection of rare cells at a frequency of one per million by flow cytometry," Cytometry, 14(5):519-526, 1993.

Gross et al., "Model study detecting breast cancer cells in peripheral blood mononuclear cells at frequencies as low as 10(−7)," Proc Natl Acad Sci USA, 92(2):537-541, Jan. 1995.

Guetta et al., "Analysis of fetal blood cells in the maternal circulation: challenges, ongoing efforts, and potential solutions" Stem Cells Dev., 13(1):93-99, Feb. 2004.

Hoshino et al., "Microchip-based immunomagnetic detection of circulating tumor cells," Lab Chip, 11(20):3449-3457, doi: 10.1039/cllc20270g, Oct. 2011 (epublished Aug. 201).

Hou et al., "Circulating tumor cells as a window on metastasis biology in lung cancer," Am J Pathol., 178(3):989-996, doi: 10.1016/j.ajpath.2010.12.003, Mar. 2011.

Hisieh et al., "High speed detection of circulating tumor cells," Biosens Bioelectron., 21(10):1893-1899, Apr. 2006 (epublished Feb. 2006).

Hulme et al., "Incorporation of prefabricated screw, pneumatic, and solenoid valves into microfluidic devices," Lab Chip. 9(1):79-86, doi: 10.1039/b809673b, Jan. 2009 (epublished Oct. 2008).

Issadore et al., "Ultrasensitive clinical enumeration of rare cells ex vivo using a micro-hall detector," Sci Transl Med, 4(141):14Ira92, doi: 10.1126/scitranslmed.3003747, Jul. 2012.

Jaggupilli et al., "Significance of CD44 and CD24 as cancer stem cell markers: an enduring ambiguity," Clin Dev Immunol., 2012:708036, doi: 10.1155/2012/708036, epublished May 2012.

Jeffries et al., "Ultrasensitive and high-throughput fluorescence analysis of droplet contents with orthogonal line confocal excitation," Anal Chem., 82(23):9948-9954, doi: 10.1021/acl02173m, Dec. 2010 (epublished Nov. 2010).

Kahn et al., "Enumeration of circulating tumor cells in the blood of breast cancer patients after filtration enrichment: correlation with disease stage," Breast Cancer Res Treat., 86(3):237-247, Aug. 2004.

Khoja et al., "A pilot study to explore circulating tumour cells in pancreatic cancer as a novel biomarker," Br J Cancer, 106(3):508-516, doi: 10.1038/bjc.2011.545, Jan. 2012 (epublished Dec. 2011).

English translation of the Japanese Notice of Final Rejection dated Mar. 29, 2023, issued in the corresponding Japanese Patent Application No. 2021-022510, filed on Jul. 1, 2014, 13 pages.

Kirby et al., "Functional characterization of circulating tumor cells with a prostate-cancer-specific microfluidic device," PLoS One, 7(4):e35976. doi: 10.1371/journal.pone.0035976, epublished Apr. 2012.

Krivacic et al., "A rare-cell detector for cancer," Proc Natl Acad Sci USA, 101(29):10501-10504, Jul. 2004.

Kuo et al., "Deformability considerations in filtration of biological cells," Lab Chip, 10(7):837-842, doi: 10.1039/b922301k, Apr. 2010 (epublished Jan. 2010).

Lara et al., "Enrichment of rare cancer cells through depletion of normal cells using density and flow-through, immunomagnetic cell separation," Exp Hematol., 32(10):891-904, Oct. 2004.

Lee et al., "Polymethylhydrosiloxane (PMHS) as a functional material for microfluidic chips," J Micromech Microeng., 18:025026, 2008.

Li et al., "Probing circulating tumor cells in microfluidics," Lab Chip, 13(4):602-609, doi: 10.1039/c2lc90148j, Feb. 2013.

Lianidou et al., "Molecular characterization of circulating tumor cells in breast cancer: challenges and promises for individualized cancer treatment," Cancer Metastasis Rev., 31(3-4):663-671, doi: 10.1007/s10555-012-9366-8, Dec. 2012.

Lin et al., "Portable filter-based microdevice for detection and characterization of circulating tumor cells," Clin Cancer Res., 16(20):5011-5018, doi: 10.1158/1078-0432.CCR-10-1105, Oct. 2010 (epublished Sep. 2010).

Lorenz et al., "Simultaneous generation of multiple aqueous droplets in a microfluidic device," Anal Chim Acta, 630(2):124-130, doi: 10.1016/j.aca.2008.10.009, Dec. 2008 (epublished Oct. 2008).

Lucci et al., "Circulating tumour cells in non-metastatic breast cancer: a prospective study," Lancet Oncol., 13(7):688-695, doi: 10.1016/SI470-2045(12)70209-7, Jul. 2012 (epublished Jun. 2012).

Maheswaran et al., "Detection of mutations in EGFR in circulating lung-cancer cells," N Engl J Med., 359(4):366-377, doi: 10.1056/NEJMoa0800668, Jul. 2008.

Martin et al., "DNA labeling in living cells," Cytometry Part A, 67A(1):45-52, 2005.

(56) References Cited

OTHER PUBLICATIONS

Mccafferty et al., "Phage antibodies: filamentous phage displaying antibody variable domains," Nature, 348(6301):552-554, Dec. 1990.
Mocellin et al., "Circulating tumor cells: the 'leukemic phase' of solid cancers," Trends Mol Med., 12(3):130-139, Mar. 2006 (epublished Feb. 2006).
Mostert et al., "Circulating tumor cells (CTCs): detection methods and their clinical relevance in breast cancer," Cancer Treat Rev., 35(5):463-474, doi: 10.1016/j.ctrv.2009.03.004, Aug. 2009 (epublished May 2009).
Nagrath et al., "Isolation of rare circulating tumour cells in cancer patients by microchip technology," Nature, 450(7173):1235-1239, Dec. 2007.
Office Action dated Jan. 29, 2014 for U.S. Appl. No. 13/257,571.
Office Action dated Apr. 26, 2016 for CA Application No. 2,758,382.
Office Action dated Jun. 4, 2015 for U.S. Appl. No. 13/257,571.
Office Action dated Jul. 12, 2016 for U.S. Appl. No. 13/257,571.
Office Action dated Aug. 3, 2016 for JP Application No. 2015-83992.
Office Action dated Sep. 11, 2014 for U.S. Appl. No. 13/257,571.
Office Action dated Nov. 24, 2015 for JP Application No. 2015-83992.
Office Action dated Dec. 9, 2015 for U.S. Appl. No. 13/257,571.
Oudejans et al., "Circulating trophoblast in maternal blood," Prenat Diagn., 23(2):111-116, Review, Feb. 2003.
Pantel et al., "Cancer micrometastases," Nature Reviews Clinical Oncology, 6(6):339-351, 2009.
Paterlini-Brechot et al., "Circulating tumor cells (CTC) detection: clinical impact and future directions," Cancer Lett., 253(2):180-204, Aug. 2007 (epublished Feb. 2007).
Patriarca et al., "Epithelial cell adhesion molecule expression (CD326) in cancer: a short review," Cancer Treat Rev., 38(1):68-75, doi: 10.1016/j.ctrv.2011.04.002, Feb. 2012 (epublished May 2011).
Payne et al., "Measurements of EGFR expression on circulating tumor cells are reproducible over time in metastatic breast cancer patients," Pharmacogenomics, 10(1):51-57, doi: 10.2217/14622416. 10.1.51, Jan. 2009I.
Pinzani et al., "Isolation by size of epithelial tumor cells in peripheral blood of patients with breast cancer: correlation with real-time reverse transcriptase-polymerase chain reaction results and feasibility of molecular analysis by laser microdissection," Hum Pathol., 37(6):711-718, Jun. 2006.
Ponti et al., "Isolation and in vitro propagation of tumorigenic breast cancer cells with stem/progenitor cell properties," Cancer Res., 65(13):5506-5511, Jul. 2005.
Punnoose et al., "Molecular biomarker analyses using circulating tumor cells," PLoS One, 5(9):e12517, doi: 10.1371/journal.pone. 0012517, Sep. 2010.
Reya et al., "Stem cells, cancer, and cancer stem cells," Nature, 414(6859):105-111, Nov. 2001.
Riethdorf et al., "Detection and HER2 expression of circulating tumor cells: prospective monitoring in breast cancer patients treated in the neoadjuvant GeparQuattro trial," Clin Cancer Res., 16(9):2634-2645, doi: 10.1158/1078-0432.CCR-09-2042, May 2010 (epublished Apr. 2010).
Riethdorf et al., "Detection of circulating tumor cells in peripheral blood of patients with metastatic breast cancer: a validation study of the Cell Search system," Clin Cancer Res., 13(3):920-928, Feb. 2007.
Schiro et al., "Continuous-flow single-molecule CE with high detection efficiency," Electrophoresis, 28(14):2430-2438, Jul. 2007.
Schiro et al., "High-throughput fluorescence-activated nanoscale subcellular sorter with single-molecule sensitivity," J Phys Chem B, 116(35):10490-10495, doi: 10.1021/jp3019233, Sep. 2012 (epublished May 2012).
Schiro et al., "Sensitive and high-throughput isolation of rare cells from peripheral blood with ensemble-decision aliquot ranking," Angew Chem Int Ed Engl., 51(19):4618-4622, doi: 10.1002/anie. 201108695, May 2012 (epublished Feb. 2012).
Sheng et al., "Aptamer-enabled efficient isolation of cancer cells from whole blood using a microfluidic device," Anal Chem., 84(9):4199-4206, doi: 10.1021/ac3005633, May 2012 (epublished Apr. 2012).
Shirasaki et al., "On-chip cell sorting system using laser-induced heating of a thermoreversible gelation polymer to control flow," Anal Chem., 78(3):695-701, Feb. 2006.
Sieuwerts et al., "Anti-epithelial cell adhesion molecule antibodies and the detection of circulating normal-like breast tumor cells," J Natl Cancer Inst., 101(1):61-66, doi: 10.1093/jnci/djn419, Jan. 2009 (epublished Dec. 2008).
Singh et al., "MUC1: a target molecule for cancer therapy," Cancer Biol Ther., Apr. 2007, 6(4):481-486.
Steeg, "Tumor metastasis: mechanistic insights and clinical challenges," Nat Med., 12(8):895-904, Aug. 2006.
Stott et al., "Isolation of circulating tumor cells using a microvortex-generating herringbone-chip," Proc Natl Acad Sci USA, 107(43):18392-18397, doi: 10.1073/pnas.1012539107, Oct. 2010.
Sun et al., "Double spiral microchamlel for label-free tumor cell separation and enrichment," Lab Chip, 12(20):3952-3960, Oct. 2012.
Theodoropoulos et al., "Circulating tumor cells with a putative stem cell phenotype in peripheral blood of patients with breast cancer," Cancer Lett., 288(1):99-106, doi: 10.1016/j.canlet.2009.06.027, Feb. 2010 (epublished Jul. 2009).
Vona et al., "Isolation by size of epithelial tumor cells : a new method for the immunomorphological and molecular characterization of circulatingtumor cells," Am J Pathol., 156(1):57-63, Jan. 2000.
Wang et al., "Highly efficient capture of circulating tumor cells by using nanostructured silicon substrates with integrated chaotic micromixers," Angew Chem Int Ed Engl., 50(13):3084-3088, doi: 10.1002/anie.201005853, Mar. 2011.
Xu et al., "A cancer detection platform which measures telomerase activity from live circulating tumor cells captured on a micro filter," Cancer Res., 70(16):6420-6426, doi: 10.1158/0008-5472.CAN-10-0686, Aug. 2010 (epublished Jul. 2010).
Yagublu et al., "Review: Fluorescent protein-based tumor models," In Vivo, 26(4):599-607, Review, Jul.-Aug. 2012.

METHODS, COMPOSITIONS AND SYSTEMS FOR MICROFLUIDIC ASSAYS

CROSS-REFERENCE

This application is a continuation of U.S. application Ser. No. 16/702,176, filed Dec. 3, 2019, which is a continuation of U.S. application Ser. No. 14/903,012, filed Jan. 5, 2016, which is a National Stage Entry of International Application No. PCT/US2014/045094, filed Jul. 1, 2014, which claims the benefit of U.S. Provisional Application Nos. 61/843,252, filed Jul. 5, 2013 and 61/894,788, filed Oct. 23, 2013, each of which applications are incorporated herein by reference in their entirety for all purposes.

STATEMENT AS TO FEDERALLY SPONSORED RESEARCH

This invention was made with government support under CA147831 awarded by the National Institutes of Health. The government has certain rights in the invention.

BACKGROUND

Circulating tumor cells (CTCs) are shed into the bloodstream from the primary tumor and are an important aspect of cancer metastasis. CTCs have been detected in many different types of cancer, such as breast, lung, prostate and pancreatic cancers. The number of CTCs directly correlates with the clinical outcome in metastatic patients, providing valuable prognostic information that can be helpful to manage clinical care.

SUMMARY

Described herein are methods, apparatuses, systems and devices for isolating and analyzing particles and performing assays.

In various aspects, methods are provided for identifying a plurality of markers present on an analyte within a fluid, wherein the method comprises: (a) detecting a signal from a first tag using a source of radiation, wherein the first tag is attached to a first structure that binds to a first marker on the analyte; (b) partitioning the analyte based on the presence of the first tag; (c) reducing the intensity of the signal of the first tag; (d) contacting the analyte with a second structure that binds to a second marker, wherein the second structure is attached to a second tag; and (e) detecting the second tag.

In various aspects, methods are provided for detecting a plurality of markers present on an analyte, the method comprising: contacting the analyte with a first tag, wherein the analyte comprises a first marker and the first tag has an affinity for the first marker; detecting a first signal emitted by the first tag, wherein the presence of the first signal indicates the presence of the first marker; partitioning a fluid comprising the analyte based on the presence of the first signal; reducing the intensity of the first signal; contacting the analyte with a second tag, wherein the analyte comprises a second marker and the second tag has an affinity for the second marker; and detecting a second signal emitted by the second tag, wherein the presence of the second signal indicates the presence of the second marker.

In various aspects, methods are provided for isolating cells from a sample comprising a first cell type and a second cell type, the methods comprising: (a) introducing the sample into a microfluidic chip via a set of tubing wherein the microfluidic chip comprises (i) at least one channel fluidly connected to the set of tubing; (ii) a detector configured to detect signals of cells within the at least one channel; and (iii) at least one chamber fluidly connected to the at least one channel; (b) flowing a portion of the sample past the detector; (c) using the detector to detect the presence or absence of the first cell type within the portion of the sample; (d) if the first cell type is detected within the portion of the sample, directing an aliquot of the sample into the chamber, wherein the aliquot comprises the first cell type; and (e) repeating steps (b), (c), and (d), thereby isolating multiple aliquots in the chamber such that the chamber comprises greater than 80% of a total number of first cell types within the sample and less than 5% of a total number of second cell types within the sample.

In various aspects, methods are provided for isolating cells from a sample, the methods comprising: (a) introducing the sample into a microfluidic chip, wherein the sample comprises a first cell type and a second cell type, and wherein the microfluidic chip comprises: a channel; a detector configured to detect a signal emitted within the channel; a chamber in fluidic communication with the channel; (b) flowing a portion of the sample through the channel, wherein the portion comprises a plurality of the first cell type, a plurality of the second cell type, or a combination thereof; (c) detecting the presence or absence of the first cell type within the portion using the detector; (d) directing the portion into the chamber if the first cell type is present within the portion; and (e) repeating (b), (c), and (d) a sufficient number of times such that the chamber comprises more than 80% of the total number of the first cell type present within the sample and less than 5% of the total number of the second cell type present within the sample.

In various aspects, apparatuses are provided for partitioning cells expressing a specific biomarker profile from a sample derived from a fluid, wherein: the apparatuses comprise a set of tubing connected to a microfluidic chip that has at least one channel and a chamber; and the apparatuses are capable of isolating the cells in the chamber, wherein, after isolation, the chamber comprises greater than 80% of the total population of cells in the sample expressing the specific biomarker profile and wherein, after isolation, the chamber comprises less than 5% of the total population of cells in the sample expressing a different biomarker profile.

In various aspects, methods are provided for identifying a plurality of markers present on an analyte, wherein the methods comprise: (a) partitioning a plurality of analytes by flowing the analytes over a substrate comprising a plurality of micro-cavities or micro-patches, wherein the majority of micro-cavities or micro-patches are capable of containing not more than one analyte and wherein the micro-cavities or micro-patches are located in a microfluidic device; (b) in the micro-cavities or micro-patches, contacting each analyte with a first structure that is capable of binding to a first marker, wherein the first structure is connected to a first tag; (c) detecting a signal from the first tag; (d) reducing the level of the signal of the first tag; (e) contacting the analyte with a second structure that binds to a second marker, wherein the second structure is connected to a second tag; and (f) detecting the second tag.

In various aspects, methods are provided for detecting a plurality of markers present on an analyte, the methods comprising: isolating an analyte in a micro-cavity or in a micro-patch by flowing a fluid over a substrate comprising the micro-cavity or micro-patch, wherein the fluid comprises the analyte; contacting the analyte with a first tag, wherein the analyte comprises a first marker, and wherein the first tag has an affinity for the first marker; detecting a first signal emitted by the first tag, wherein the presence of the first signal indicates the presence of the first marker; reducing the intensity of the first signal; contacting the analyte with a second tag, wherein the analyte comprises a second marker, and wherein the second tag has an affinity for the second marker; and detecting a second signal emitted by the second tag, wherein the presence of the second signal indicates the presence of the second marker.

In various aspects, systems are provided for detecting a particle in a fluid sample, the systems comprising: a microfluidic chip comprising an input channel, a first output channel, a second output channel, and a directional flow channel; a valve, wherein the valve is separable from the microfluidic chip, and wherein: the valve regulates the flow of a first fluid in the directional flow channel; and the flow of the first fluid in the directional flow channel directs the flow of a second fluid from the input channel to the first output channel, the second output channel, or a combination thereof; a detector configured to detect a signal emitted from a portion of the second fluid in the input channel; and a processor configured to: assign a value to the portion based on the signal; and operate the valve. In some aspects, the valve is an electro-actuated valve.

In various aspects, systems are provided for detecting a particle in a fluid sample, the system comprising: (a) a microfluidic chip comprising at least one sample input channel, at least one directional flow channel, and at least two output channels, wherein the at least one directional flow channel intersects the sample input channel; (b) an electro-actuated valve that is located on a device that is not part of the microfluidic chip, wherein the electro-actuated valve controls the flow of a fluid by controlling an input channel that intersects at least one directional flow channel or at least one of the at least two output channels; (c) at least one detector capable of detecting one or more analytes in an aliquot of the fluid sample; and (d) a processor capable of assigning a value to the aliquot based on the presence, absence, identity, composition, or quantity of analytes in the aliquot, wherein the processor is in communication with the detector and the electro-actuated valve.

In various aspects, methods are provided for isolating an aliquot of a fluid sample within a microfluidic chip, wherein the aliquot comprises a rare particle, the methods comprising the steps of: (a) detecting the presence or absence of the rare particle in the aliquot; (b) assigning a value to the aliquot based on the presence or absence of the rare particle; and (c) directing the flow of the aliquot based on the assigned value by opening an electro-actuated valve, wherein the electro-actuated valve is located on a device that is external to the microfluidic chip. In some aspects, the microfluidic chip comprises a sample input channel, at least two output channels, and at least one directional flow channel, and wherein the electro-actuated valve controls the flow of fluid within the directional flow channel.

In various aspects, devices are provided for detecting a rare particle in a fluid sample, the devices comprising: an input channel; a first output channel; a second output channel; a detector configured to detect the presence or absence of a particle in a portion of the fluid sample; a mechanism for directing the flow of the portion from the input channel to the first output channel, the second output channel, or a combination thereof based on the presence or absence of the particle; and a filter in fluidic communication with the first output channel.

In various aspects, devices are provided for detecting a rare particle in a fluid sample, the devices comprising: (a) at least one sample input channel; (b) at least two output channels, wherein at least one of the two output channels is in fluidic communication with an array of apertures; (c) at least one detector capable of detecting one or more rare particles in an aliquot of the fluid sample; and (d) a mechanism for sorting the one or more rare particles by directing the flow of aliquots containing the one or more rare particles through a first output channel.

In various aspects, integrated systems are provided for performing an assay, the systems comprising: a fluid sample comprising a particle, wherein the particle comprises a marker; an input channel; a first output channel; a second output channel; a first detector configured to detect the presence or absence of the particle in a portion of the fluid sample, the portion disposed within the input channel; a mechanism for directing the flow of the portion from the input channel to the first output channel based on the presence or absence of the particle; a micro-cavity in fluidic communication with the first output channel and configured to trap the particle; and a second detector configured to detect the presence or absence of the marker in the micro-cavity.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE DISCLOSURE

Figure 1:
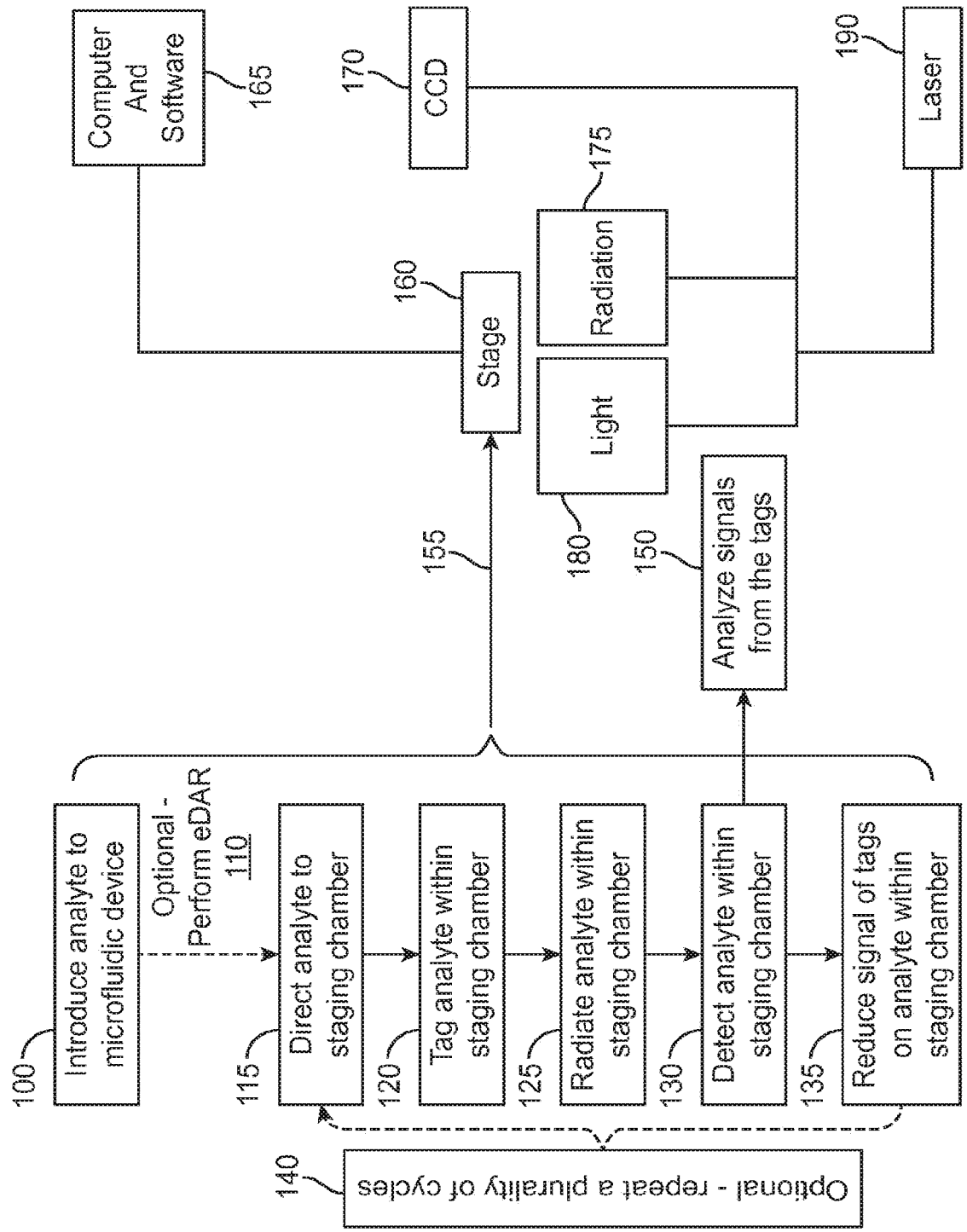
FIG. 1 is an overview of immunostaining and photobleaching using a fluidic microfluidic chip according to an aspect of the present disclosure.

This disclosure provides methods, systems and devices for detecting, separating and analyzing particles (e.g., cells) in a fluid sample (e.g., blood), often with the use of a microfluidic apparatus. The particles can be rare particles (e.g., rare cells). Many of the microfluidic apparatuses provided herein can be used to perform Ensemble Decision Aliquot Ranking (eDAR) on a fluid sample, which permits analysis of the fluid sample after the fluid sample is divided into aliquots.

In some aspects, an eDAR apparatus can be used to (i) detect the presence or absence of a rare particle (e.g., rare cell) in an aliquot of the fluid sample, (ii) rank the aliquot according to the presence or absence of a rare particle, for example by assigning a term such as non-zero or null to the aliquot; and (iii) direct the flow or collection of the aliquot based on the assigned ranking using a scheme such as a hydrodynamic switching scheme. The aliquots can be a portion of the total volume of a fluid sample to be analyzed. In some aspects, an aliquot occupies a three-dimensional space and the particles within the aliquot can be distributed randomly.

In some aspects, this disclosure provides apparatuses and methods for performing eDAR on a fluid sample with a very high efficiency, sensitivity and/or recovery rate. For example, the eDAR apparatus provided herein can recover greater than 95% of a particular rare cell type from a fluid sample (e.g., blood, whole blood, urine, etc.). The eDAR apparatus can function with a less than 10%, less than 5%, or even 0% false positive rate. The false positive rate can be over a number of samples, such as greater than 10 samples, or greater than 15 samples. The speed of the eDAR apparatus can also be very fast. For example, an entire sample can be processed in less than 25 minutes, less than 20 minutes, etc.

Often, the eDAR apparatus provided herein comprises a microfluidic chip containing (a) channels; (b) chambers; (c) filters; (d) detectors, and/or (e) valves. The microfluidic chip can be part of a larger system that also includes (a) vessels for holding buffers; (b) off-chip valves (e.g., solenoid valves); (c) light sources and detectors; (d) tubing; (e) sample ports; (f) digital processors and/or other features. The filters and microslits or micro-apertures (e.g., array of microslits) can be used to further purify a sample. Herein, the terms "microslit" and "micro aperture" are used interchangeably, and microslits or micro apertures can also include an array of posts where the inter-post spacing is used for carrying out filtration. The inter-post spacing can be uniform or variable. In some aspects, a sample is introduced to an eDAR apparatus, which then performs active sorting of the cells by a hydrodynamic switching scheme. The hydrodynamic switching scheme can include channels with a particular geometry, as described further herein.

In some aspects, this disclosure provides methods and apparatuses for capturing more than one type of analyte (e.g., rare cell), or more than one subpopulation of analytes (e.g., rare cells) in a population of analytes (e.g., rare cells) within a sample. A sample can be labeled with a plurality of detection reagents so that a plurality of analytes (e.g., rare cells) are detected. For example, the sample can be a mixed sample and contain a mixed population of rare cells. The mixed population of rare cells can comprise an epithelial cell and a mesenchymal cell, amongst other cell types. Within the plurality of detection reagents, one detection reagent can bind to an epithelial marker on the epithelial cell, while a different reagent binds to a mesenchymal marker on the mesenchymal cell.

The mixed sample can be introduced into the microfluidic chip apparatus at an input channel Side channels on the apparatus can be used to control the hydrodynamic switching of the flow of the mixed sample. The flow of the fluid can be controlled by two solenoids so that the plurality of analytes are separated into two different regions of the microfluidic chip. In some aspects, the analytes are further purified on the microfluidic chip, such as by passing the fluid through a filter or an array of microslits. The analytes can be collected at the filter or on the array of microslits.

This disclosure further provides a method for a staining and washing system that can be coupled with eDAR, or that can be used with other microfluidic devices. The method of the staining and washing system can be in-line. The in-line staining and washing methods provides for an automated process of isolating individual analytes (e.g., cells) and detecting biomarkers. The method can also reduce the amount of detection reagents (e.g., antibodies) needed to detect different markers on an analyte. The method can further minimize the dead volume of the system. Additionally, the apparatus can include a mechanism to avoid introduction of air bubbles into the apparatus.

eDAR can be coupled with downstream methods of characterization and analysis. The methods can include cellular and molecular analysis of rare cells. In some aspects, immunostaining can be used to determine expression of certain biomarkers on rare cells. A semi-automated method and system for immunostaining is described herein.

This disclosure further provides a system, method and apparatus for using single-analyte arrays with a fluidic sample. A single-analyte array can comprise a plurality of wells or micro-wells configured so that not more than one analyte in a fluid sample will occupy a particular well. In some aspects, the micro-wells can be micro-cavities. A single-analyte array can also comprise a plurality of patches or micro-patches configured so that not more than one analyte in a fluid sample will occupy a particular patch. A fluidic sample comprising analytes can be introduced into the array and the analytes (e.g., cells) and can be partitioned so that at least 80% of the micro-wells or micro-patches of the device contain no more than one analyte. In some aspects, the single-analyte array can be used with a microfluidic system. In some aspects, the micro-fluidic system can be an eDAR device.

The single-analyte array, in some aspects, involves a method comprising the steps of; containment or physical trapping of single cells as the cells are transported in a liquid phase, and following the flow path of this phase, transiting to a physically defined position, and residing in the defined position due to the ensuing flow based forces or surface adhesive forces. In another case, the cells are trapped sequentially as the fluidic flow path is serial with respect of inlet to outlet. In another case, multiple fluid flow paths and commensurate multiple single cells are trapped/sequestered in a parallel manner, due to the numerous flow paths that can simultaneously be experienced by the cells between the inlet and outlet.

The methods, systems, apparatuses and devices described in the present disclosure can be used in a wide variety of applications in biology and pathology for the separation, concentration, and/or isolation of analytes (e.g., rare cells). For example, some applications can include, but are not limited to, the capture of rare cells (e.g., cancer cells, cancer stem cells, malaria infected erythrocytes, stem cells, fetal cells, immune cells, infected cells) from fluids (e.g., body fluids) for diagnosis and prognosis of disease; isolation of single-celled parasites (e.g., giardia, cryptosporidium) for water quality monitoring; isolation of infected cells (e.g., lymphocytes, leukocytes) for monitoring disease progression (e.g., HIV, AIDS, cancer); fetal cells in maternal blood for screening (e.g., disease, genetic abnormalities); stem cells for use in therapeutic applications; prion-infected cells for prion-related (e.g., mad cow) disease screening; and others.

In a particular aspect, the rare particle is a rare cell. Rare cells can be nucleated or non-nucleated. Rare cells include, but are not limited to, cells expressing a malignant phenotype; fetal cells, such as fetal cells in maternal peripheral blood; tumor cells, such as tumor cells which have been shed from tumor into blood or other bodily fluids; cells infected with a virus, such as cells infected by HIV, cells transfected with a gene of interest; and aberrant subtypes of T-cells or B-cells present in the peripheral blood of subjects afflicted with autoreactive disorders.

As used herein, an "ensemble-decision" refers to a decision made based on the detection of the presence or absence of a characteristic in an ensemble, or a group, of particles. A group can comprise at least 3 particles, analytes and/or cells. In some aspects, an ensemble-decision will be made based on the presence or absence of a single distinct particle in an aliquot of a fluid sample containing a plurality of particles. Importantly, ensemble-decisions made based on the presence or absence of a single particle will be applied to the entire aliquot (i.e., to all of the particles present in the aliquot).

As used herein, an "aliquot" refers to a portion of the total volume of a fluid sample to be analyzed. An aliquot can contain at least one particle, analyte or cell. An aliquot can contain a group of particles, analytes or cells. An aliquot occupies a three-dimensional space and the particles within distribute randomly without organization. An aliquot has a finite depth, and particles can distribute along the depth with no discernible layers. In the context of the present application, an aliquot is analyzed in its entirety without subdivision.

As used herein, the phrase "partitioning a fluid" refers to separating or otherwise redirecting a portion or aliquot of a fluid from the total volume of a fluid sample.

In certain aspects, an aliquot can consist of a fraction of a larger fluid sample, for example, about ½ of a fluid sample, or about ⅓, ¼, ⅕, ⅙, 1/7, ⅛, 1/9, 1/10, or less of a fluid sample. In certain aspects, an aliquot can consist of, for example, about 10% of a fluid sample, or about 9%, 8%, 7%, 6%, 5%, 4%, 3%, 2%, 1%, 0.5%, 0.1%, 0.05%, 0.01%, 0.001%, or less of a fluid sample. As such, a fluid that is to be examined or processed by an eDAR methodology provided herein can be divided, for example, into at least about 2 aliquots, or at least about 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 130, 140, 150, 175, 200, 225, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, 3,000, 3,500, 4,000, 4,500, 5,000, 6,000, 7,000, 8,000, 9,000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1 million, 2 million, 3 million, 4 million, 5 million, 6 million, 7 million, 8 million, 9 million, 10 million, or more aliquots. One of skill in the art would understand that the number of aliquots into which a fluid sample would be partitioned into will depend upon the number of rare particles expected in the fluid and the total volume of the fluid sample.

In certain aspects, an aliquot can comprise a fraction of a larger fluid sample, for example, ½ of a fluid sample, or ⅓, ¼, ⅕, ⅙, 1/7, ⅛, 1/9, 1/10, or less of a fluid sample. In certain aspects, an aliquot can comprise, for example, 10% of a fluid sample, or 9%, 8%, 7%, 6%, 5%, 4%, 3%, 2%, 1%, 0.5%, 0.1%, 0.05%, 0.01%, 0.001%, or less of a fluid sample. As such, a fluid that is to be examined or processed by an eDAR methodology provided herein can be divided, for example, into at least 2 aliquots, or at least 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 130, 140, 150, 175, 200, 225, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, 3,000, 3,500, 4,000, 4,500, 5,000, 6,000, 7,000, 8,000, 9,000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1 million, 2 million, 3 million, 4 million, 5 million, 6 million, 7 million, 8 million, 9 million, 10 million, or more aliquots. One of skill in the art would understand that the number of aliquots into which a fluid sample would be partitioned into will depend upon the number of rare particles expected in the fluid and the total volume of the fluid sample.

In certain aspects, an aliquot can have a volume, for example, of between about 0.1 nL and about 10 mL, or between about 1 nL and about 1 mL, or between about 1 nL and about 100 µL, or between about 1 nL and about 10 µL, or between about 1 nL and about 1 µL, or between about 1 nL and about 100 nL, or between about 0.1 nL and about 10 nL.

In certain aspects, an aliquot can have a volume, for example, of between 0.1 nL and 10 mL, or between 1 nL and 1 mL, or between 1 nL and 100 µL, or between 1 nL and 10 µL, or between 1 nL and 1 µL, or between 1 nL and 100 nL, or between 0.1 nL and 10 nL.

As used herein, the term "ranking" refers to assessing a quantitative property, qualitative property, or importance of an aliquot by categorization. In one aspect, an aliquot can be ranked as either null (for example, when a rare particle is not detected in the aliquot) or nonzero (for example, when at least one rare particle is detected in an aliquot). In one aspect, the ranking can be binary. In other aspects, an aliquot can be ranked according to additional categories, for example, which correlate with the concentration of the rare particle in the aliquot, the identity of the rare particle in the aliquot, the identities of a plurality of different rare particles in the aliquot, and the like. In this fashion, any number of categories can be assigned based on ranges of concentration, for example, between about 1 and 10, between about 11 and 20, between about 1 and 50, between about 51 and 100, between about 1 and 100, between about 101 and 201, etc. In some aspects, the number of categories can be assigned based on ranges of concentration, for example, between 1 and 10, between 11 and 20, between 1 and 50, between 51 and 100, between 1 and 100, between 101 and 201, etc. These rankings can be assigned an arbitrary number corresponding to one of a number of predetermined quantitative or qualitative categories (e.g., 0, 1, 2, 3, 4, 5, etc.), or a number corresponding to an actual value for the number or approximate number or rare particles in the aliquot.

As used herein, the term "microfluidic chip" is used interchangeably with the terms chip, fluidic chip, microchip or fluidic microchip.

As used herein, a "computer" refers to at least a digital processor. The digital processor can be, but is not limited to, a field programmable gate array (FGPA), application specific integrated circuit (ASIC) or real-time (RT) processor.

Devices, Apparatuses and Methods for Performing Assays

The methods described in the present disclosure can be used for the isolation and detection of an analyte from a fluid sample. In some aspects, the method can include detection of molecules on the analyte using a first tag or a first set of tags, reduction of the signal emitted by the tags and detection of another set of molecules on the analyte using a second tag or second set of tags. In some aspects, the method can be performed using analytes separated from a sample. In some aspects, the method can be combined with a microfluidic device. The microfluidic device can be used to isolate analytes from a sample. In some aspects, the method, referred to as immunostaining and bleaching, can be performed on the microfluidic device used to isolate analytes from a sample.

A concept diagram illustrating an exemplary case of the immunostaining and photobleaching method is shown in FIG. 1. The method of immunostaining and photobleaching can be performed on the microfluidic device 100 along with a detection scheme 155. The microfluidic device 100 can be placed on a stage 160 of a microscope above or under a source of light 180 and a source of radiation 175. The analyte can be introduced to the microfluidic device 100 and eDAR can be performed 110 to isolate the analyte from the fluid sample. The isolated analyte can be directed to the staging chamber 115 where the analyte can remain for the duration of the immunostaining and photobleaching method. The analyte can be contacted with one or more tags 120. A source of radiation 175 can radiate the one or more tags on the analyte 125 and the signal emitted by the one or more tags can be detected 130. The source of radiation 175 can originate from a laser, or light emitting diode (LED), or a lamp 190. The signal emitted by the tag can be reduced 135 using a source of light 180. During the reduction of the signal 135, a digital processor (e.g., computer) and software 165 and a charge-coupled device (CCD) 170 can be used to detect 130 the duration of the signal emitted by the tag. In some aspects, the exposure time of the tagged analyte to the source of illumination can persist until the signal emitted by the tag is eliminated. Steps 120, 125, 130 and 135 comprise one cycle of immunostaining and photobleaching. The cycles 140 of immunostaining and photobleaching can be repeated until multiple cycles are complete. The final round of photobleaching 135 may or may not be performed during the final cycle. After detection of the analyte 130, the final cycle can proceed to analyze the signals emitted by the tags 150.

Figure 2:
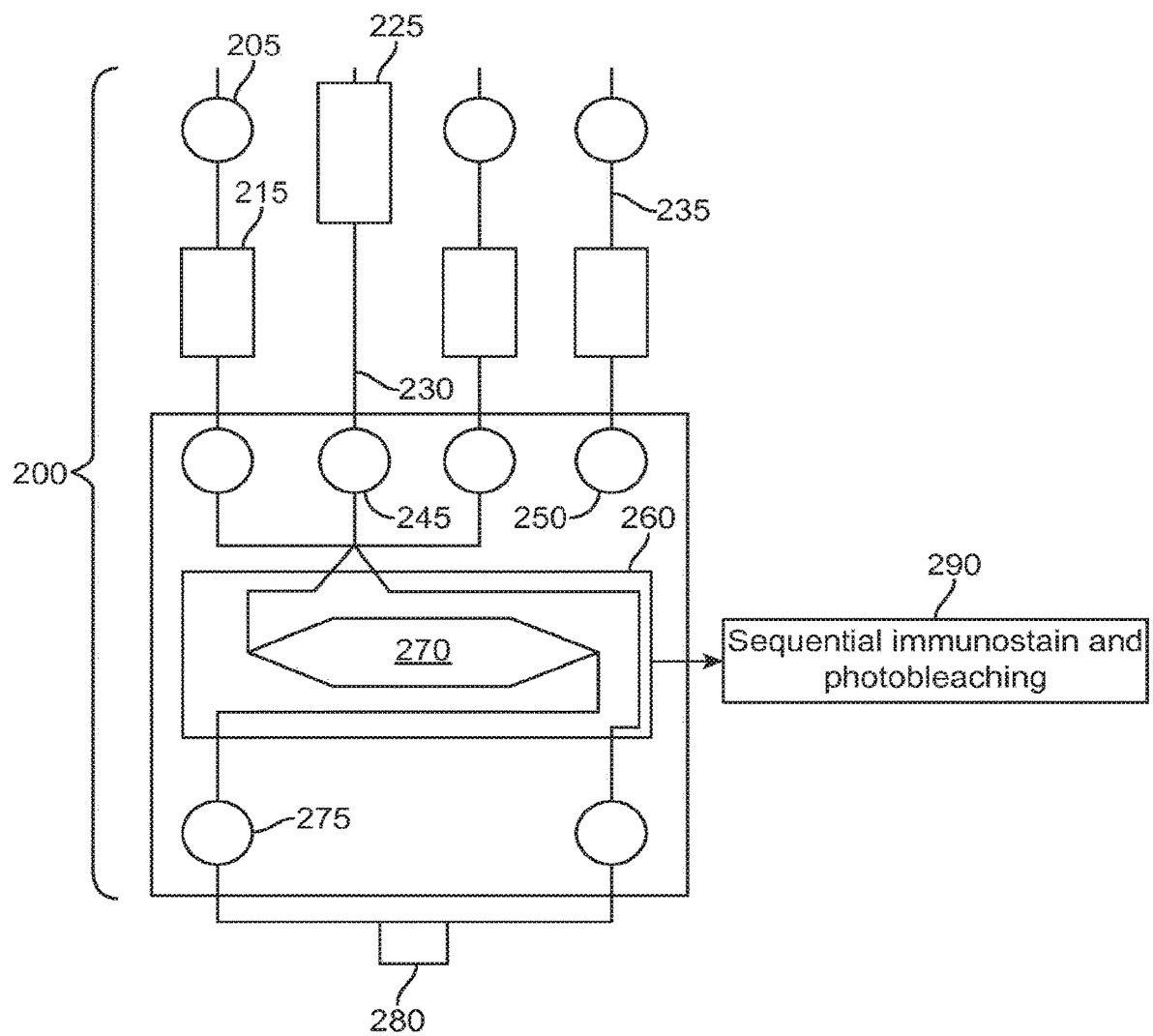
FIG. 2 is an overview of immunostaining and photobleaching using the eDAR apparatus according to an aspect of the present disclosure.

A concept diagram illustrating an exemplary case of the eDAR apparatus 200 that can be used in combination with the immunostaining and photobleaching method 290 is shown in FIG. 2. The fluid sample reservoir 225 and channel 230 can connect to the fluid sample inlet 245. The buffer reservoir 215 can connect to a source of pressurized gas 205 through a line 235. The buffer inlet 250 can be connected to the fluid sample inlet 245. The filtration area 270 can be connected to the buffer inlet 250, the fluid sample inlet 245, the outlet 275 and the waste chamber 280. A fluid sample can enter the eDAR apparatus 200 and an analyte or a plurality of analytes can be trapped on the filtration stage 270. The filtration stage can contain a plurality of chambers where each chamber can contain a single analyte. The immunostaining and photobleaching method 290 can be performed on a section of the microfluidic chip 260 which can contain the filtration stage 270.

This disclosure provides a method for sequential immunostaining and photobleaching that can be performed using a single-analyte array. The single-analyte array allows for sequestration, trapping, manipulation, and detection of single-analytes (e.g., cells). Often, the cells are trapped by forces generated from fluid flow, gravity, surface adhesive forces, chemical forces, or optical forces. In some aspects, the single-analyte array wells are functionalized with an element that can bind (e.g., covalently, ionically, etc.) the trapped cell. Trapped cells can be contacted with a chemical agent. The chemical agent can be a label used to detect exterior molecules, or penetrate the cell membrane and label intracellular molecules. Labeled cells can be imaged and further analyzed.

Figure 3:
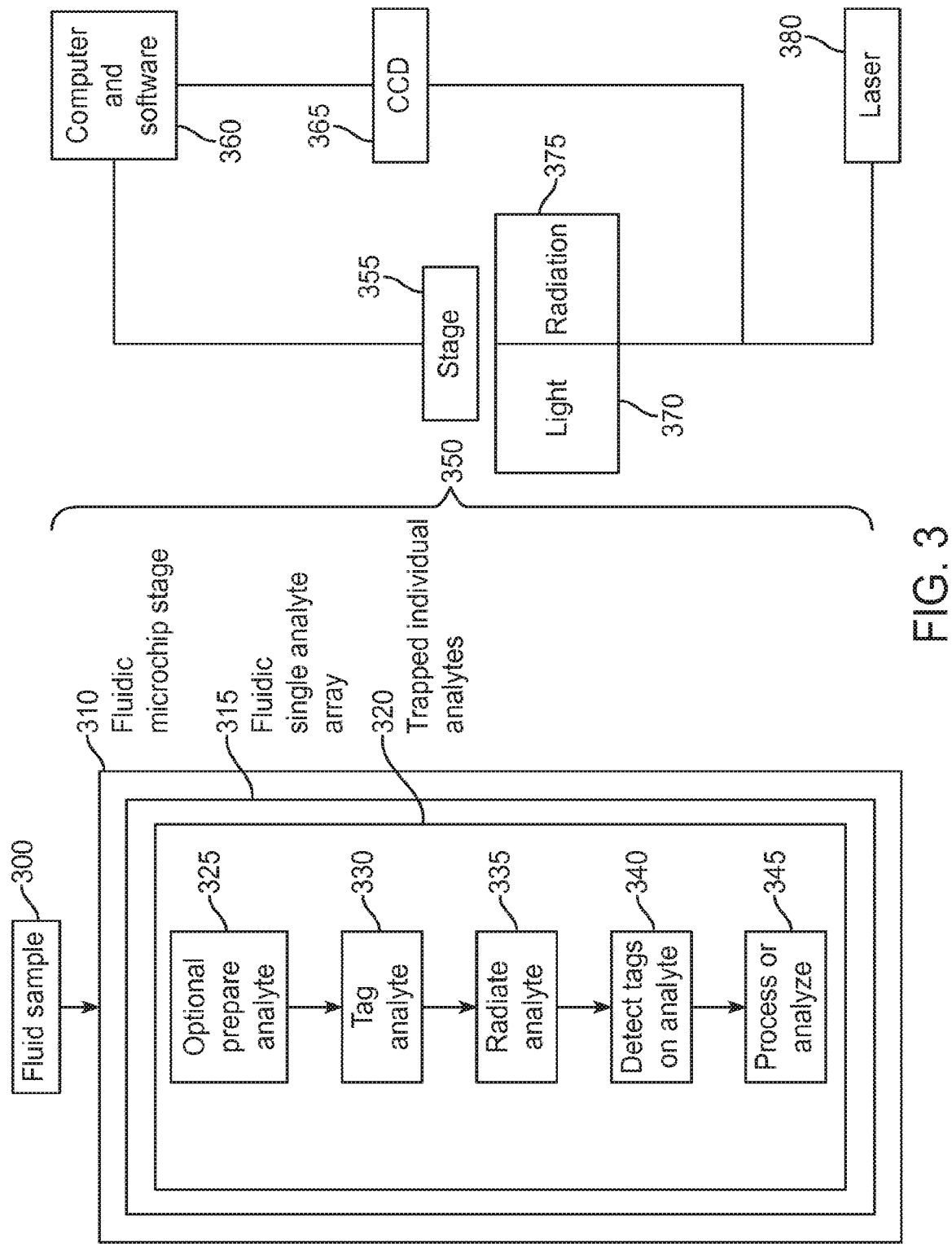
FIG. 3 is an overview of immunostaining and photobleaching using a single-analyte array according to an aspect of the present disclosure.

A concept diagram illustrating an exemplary case of the single-analyte array in combination with an immunostaining method is shown in FIG. 3. The fluidic single-analyte array 315 can be part of a microfluidic chip or structure and placed on a microfluidic stage 310. The method of immunostaining can be performed on the fluidic single-analyte array 315 along with a detection scheme 350. The microfluidic chip stage 310 can be placed on a stage 355 of a microscope above or under a source of light 370 and a source of radiation 375. The analytes in a fluid sample can be introduced to the fluidic single-analyte array 300. The isolated analytes can be directed to an area of the fluidic single-analyte array 320 where the trapped single-analytes can remain for the duration of the immunostaining method. The analytes can be prepared 325 using a variety of methods which can include, but are not limited to; permeabilization and/or fixation. The analyte can be contacted with one or more tags 330. A source of radiation 375 can radiate 335 the one or more tags on the analyte and the signal emitted by the one or more tags can be detected 340. The source of radiation 375 can originate from a laser 380. The analytes can undergo further processing and analysis 345. A digital processor (e.g., computer) and software 360, and a charge-coupled device (CCD) 365 can be used to detect the signal emitted by the tag.

For sequential immunostaining and photobleaching, the signal emitted by the tag can be reduced using a source of light 370. During the reduction of the signal, a computer and software 360, and a charge-coupled device (CCD) 365 can be used to detect the intensity of the signal emitted by the tag. The exposure time of the tagged analytes to the source of illumination can persist until the signal emitted by the tag is eliminated. Steps 330, 335, 340 and 345 comprise one cycle of immunostaining and photobleaching. The cycles can be repeated until multiple cycles are complete.

The eDAR apparatus can be used for the identification and isolation of analytes (e.g., rare cells). eDAR can process a sample in aliquots and can collect rare cells in a channel or a chamber by an active sorting step controlled by a hydrodynamic switching scheme. An "all-in-one microfluidic chip," referred to herein as microfluidic chip, with channels and chambers can be used for sorting rare cells. The microfluidic chip can be composed, in part, of a functional area, a microfabricated filter. eDAR can be used to rapidly (e.g., less than or equal to 12.5 minutes per 1 mL) analyze a fluid containing a mixed population of analytes (e.g., whole blood at greater than or equal to one milliliter) with a high recovery ratio (e.g, greater than or equal to 90%) and a low false positive rate (e.g., close to zero).

The general structure of the microfluidic chip and an example configuration of eDAR is depicted in FIG. 7A. The bottom left channel can be used to collect sorted aliquots and can be used to transfer them to the subsequent purification (e.g., purification chamber) area (e.g., 20,000 microslits). The area marked with a dashed box is further depicted in FIG. 7B-D. An example flow condition when no positive aliquot was ranked is shown in FIG. 7B. The blood flow can be switched to the collection channel, and the sorted aliquot can be confirmed by the second window in FIG. 7C. FIG. 7D shows that the blood flow can be switched back after sorting the aliquot.

The apparatus can have several flow rates. The flow rates can refer to the rate in which a fluid flows through the eDAR apparatus and any components attached to the apparatus. In some aspects, exemplary flow rates can be less than about 5 µL/min, 10 µL/min, 20 µL/min, 25 µL/min, 30 µL/min, 35 µL/min, 40 µL/min, 41 µL/min, 42 µL/min, 43 L/min, 44 µL/min, 45 µL/min, 46 µL/min, 47 µL/min, 48 µL/min, 49 µL/min, 50 µL/min, 51 µL/min, 52 µL/min, 53 µL/min, 54 µL/min, 55 µL/min, 56 µL/min, 57 µL/min, 58 µL/min, 59 µL/min, 60 µL/min, 61 µL/min, 62 µL/min, 63 µL/min, 64 µL/min, 65 µL/min, 66 µL/min, 67 µL/min, 68 µL/min, 69 µL/min, 70 µL/min, 71 µL/min, 72 µL/min, 73 µL/min, 74 µL/min, 75 µL/min, 76 µL/min, 77 µL/min, 78 µL/min, 79 µL/min, 80 µL/min, 81 µL/min, 82 µL/min, 83 µL/min, 84 µL/min, 85 µL/min, 86 µL/min, 87 µL/min, 88 µL/min, 89 µL/min, 90 µL/min, 91 µL/min, 92 µL/min, 93 µL/min, 94 µL/min, 95 µL/min, 96 µL/min, 97 µL/min, 98 µL/min, 99 µL/min, 100 µL/min, 105 µL/min, 110 µL/min, 115 µL/min, 120 µL/min, 125 µL/min, 130 µL/min, 140 µL/min, 150 µL/min, 160 µL/min, 170 µL/min, 180 µL/min, 190 µL/min, 200 µL/min, 225 µL/min, 250 µL/min, 275 µL/min, 300 µL/min, 350 µL/min, 400 µL/min, 450 µL/min, 500 µL/min, 600 µL/min, 700 µL/min, 800 µL/min, 900 µL/min or 1000 µL/min.

In some aspects, the flow rate can be within the range of about 5 µL/min-30 µL/min, 15 µL/min-50 µL/min, 25 µL/min-75 µL/min, 40 µL/min-80 µL/min, 50 µL/min-90 µL/min, 60 µL/min-100 µL/min, 800 µL/min-160 µL/min, 90 µL/min-180 µL/min, 100 µL/min-200 µL/min, 150 µL/min-300 µL/min, 200 µL/min-400 µL/min, 300 µL/min-500 µL/min, 400 µL/min-600 µL/min, 500 µL/min-700 µL/min, 600 µL/min-800 µL/min, 700 µL/min-900 µL/min or 800 µL/min-1000 µL/min.

In some aspects, exemplary flow rates can be less than 5 µL/min, 10 µL/min, 20 µL/min, 25 µL/min, 30 µL/min, 35 µL/min, 40 µL/min, 41 µL/min, 42 µL/min, 43 L/min, 44 µL/min, 45 µL/min, 46 µL/min, 47 µL/min, 48 µL/min, 49 µL/min, 50 µL/min, 51 µL/min, 52 µL/min, 53 µL/min, 54 µL/min, 55 µL/min, 56 µL/min, 57 µL/min, 58 µL/min, 59 µL/min, 60 µL/min, 61 µL/min, 62 µL/min, 63 µL/min, 64 µL/min, 65 µL/min, 66 µL/min, 67 µL/min, 68 µL/min, 69 µL/min, 70 µL/min, 71 µL/min, 72 µL/min, 73 µL/min, 74 µL/min, 75 µL/min, 76 µL/min, 77 µL/min, 78 µL/min, 79 µL/min, 80 µL/min, 81 µL/min, 82 µL/min, 83 µL/min, 84 µL/min, 85 µL/min, 86 µL/min, 87 µL/min, 88 µL/min, 89 µL/min, 90 µL/min, 91 µL/min, 92 µL/min, 93 µL/min, 94 µL/min, 95 µL/min, 96 µL/min, 97 µL/min, 98 µL/min, 99 µL/min, 100 µL/min, 105 µL/min, 110 µL/min, 115 µL/min, 120 µL/min, 125 µL/min, 130 µL/min, 140 µL/min, 150 µL/min, 160 µL/min, 170 µL/min, 180 µL/min, 190 µL/min, 200 µL/min, 225 µL/min, 250 µL/min, 275 µL/min, 300 µL/min, 350 µL/min, 400 µL/min, 450 µL/min, 500 µL/min, 600 µL/min, 700 µL/min, 800 µL/min, 900 µL/min or 1000 µL/min.

In some aspects, the flow rate can be within the range of 5 µL/min-30 µL/min, 15 µL/min-50 µL/min, 25 µL/min-75 µL/min, 40 µL/min-80 µL/min, 50 µL/min-90 µL/min, 60 µL/min-100 µL/min, 800 µL/min-160 µL/min, 90 µL/min-180 µL/min, 100 µL/min-200 µL/min, 150 µL/min-300 µL/min, 200 µL/min-400 µL/min, 300 µL/min-500 µL/min, 400 µL/min-600 µL/min, 500 µL/min-700 µL/min, 600 µL/min-800 µL/min, 700 µL/min-900 µL/min or 800 µL/min-1000 µL/min.

The apparatus can have several sorting efficiencies. The sorting efficiency can refer to the recovery of analytes of interest. In some aspects, an exemplary sorting efficiency can be greater than about 5%, 10%, 20%, 25%, 30%, 35%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. In some aspects, the sorting efficiency can be within the range of about 5%-30%, 15%-50%, 25%-75%, 40%-80%, 50%-90% or 60%-100%.

In some aspects, an exemplary sorting efficiency can be greater than 5%, 10%, 20%, 25%, 30%, 35%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. In some aspects, the sorting efficiency can be within the range of 5%-30%, 15%-50%, 25%-75%, 40%-80%, 50%-90% or 60%-100%.

The eDAR apparatus can have several recovery ratios. The recovery ratio can refer to the recovery of analytes of interest. In some aspects, the recovery ratio can be greater than about 5%, 10%, 20%, 25%, 30%, 35%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. In some aspects, the recovery ratio can be within the range of about 5%-30%, 15%-50%, 25%-75%, 40%-80%, 50%-90% or 60%-100%.

In some aspects, the recovery ratio can be greater than 5%, 10%, 20%, 25%, 30%, 35%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%.

In some aspects, the recovery ratio can be within the range of 5%-30%, 15%-50%, 25%-75%, 40%-80%, 50%-90% or 60%-100%.

In some aspects an eDAR apparatus or method is used to separate a first cell type from a second cell type. In some aspects, an isolated sample comprises greater than 5%, 10%, 20%, 25%, 30%, 35%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% of a total number of the first cell type. In some aspects, an isolated sample comprises less than than 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45, 50%, 60%, 70%, 80%, or 90% of a total number of the second cell type.

The eDAR apparatus can include a microscope equipped with sources of radiation (e.g., lasers) for excitation and a mode of detection, sources of light (e.g., photobleaching), a timer, tubing, a waste-collection device, a camera for imaging tagged analytes (e.g., cells), pumps to control the flow of fluid in and out of the microfluidic chip, a digital processor to control the active sorting step and a digital processor (e.g., computer system) for processing images. The digital processor can be a computer.

In some aspects, the eDAR platform can include an apparatus for the capture of more than one analyte (e.g., rare cell). The "dual-capture" eDAR can separate multiple rare cells from a mixed sample. The mixed sample (e.g., fluid sample) can be labeled with a detection reagent and entered into the top of the "dual-capture" apparatus at a main channel. Two side channels can be used to control the hydrodynamic switching of the flow of the mixed sample. In some aspects, the flow can be controlled using two solenoids. Two subpopulations of rare cells can be separated and trapped on two different filtration areas on the same microfluidic chip.

In various aspects, apparatuses are provided for partitioning cells expressing a specific biomarker profile from a sample derived from a fluid, wherein: the apparatuses comprise a set of tubing connected to a microfluidic chip that has at least one channel and a chamber; and the apparatuses are capable of isolating the cells in the chamber, wherein, after isolation, the chamber comprises greater than 80% of the total population of cells in the sample expressing the specific biomarker profile and wherein, after isolation, the chamber comprises less than 5% of the total population of cells in the sample expressing a different biomarker profile.

In some aspects, the isolation of the cells expressing a specific biomarker profile occurs in less than 20 minutes. In some aspects, the specific biomarker profile is present on less than 5% of the cells in the sample of fluid. In certain aspects, the fluid is blood. In further aspects, the fluid is fractionated whole blood. In still further aspects, the fluid is the nucleated cell fraction of whole blood.

In various aspects, systems are provided for detecting a particle in a fluid sample, the systems comprising: a microfluidic chip comprising an input channel, a first output channel, a second output channel, and a directional flow channel; a valve, wherein the valve is separable from the microfluidic chip, and wherein: the valve regulates the flow of a first fluid in the directional flow channel; and the flow of the first fluid in the directional flow channel directs the flow of a second fluid from the input channel to the first output channel, the second output channel, or a combination thereof; a detector configured to detect a signal emitted from a portion of the second fluid in the input channel; and a processor configured to: assign a value to the portion based on the signal; and operate the valve. In some aspects, the valve is an electro-actuated valve.

In various aspects, systems are provided for detecting a particle in a fluid sample, the system comprising: (a) a microfluidic chip comprising at least one sample input channel, at least one directional flow channel, and at least two output channels, wherein the at least one directional flow channel intersects the sample input channel; (b) an electro-actuated valve that is located on a device that is not part of the microfluidic chip, wherein the electro-actuated valve controls the flow of a fluid by controlling an input channel that intersects at least one directional flow channel or at least one of the at least two output channels; (c) at least one detector capable of detecting one or more analytes in an aliquot of the fluid sample; and (d) a processor capable of assigning a value to the aliquot based on the presence, absence, identity, composition, or quantity of analytes in the aliquot, wherein the processor is in communication with the detector and the electro-actuated valve.

In some aspects, the electro-actuated valve is a solenoid valve. In certain aspects, the electro-actuated valve controls the flow of the fluid in at least one directional flow channel. In further aspects, the electro-actuated valve is normally closed and wherein the electro-actuated valve opens after receiving a signal from the processor. In still further aspects, the electro-actuated valve is normally open and wherein the electro-actuated valve closes after receiving a signal from the processor.

In some aspects, at least one directional flow channel comprises at least two ports and wherein the electro-actuated valve controls the flow of fluid through one of the ports. In certain aspects, the electro-actuated valve directly controls the flow of a fluid in at least one directional flow channel. In some aspects, the electro-actuated valve directly controls the flow of a fluid in a channel that feeds into at least one directional flow channel. In certain aspects, the electro-actuated valve directly controls the flow of a fluid in only one directional flow channel. In further aspects, the electro-actuated valve directly controls the flow of a fluid in an output channel. In still further aspects, the electro-actuated valve directly controls the flow of a fluid in a channel that feeds into an output channel. In some aspects, the electro-actuated valve is a piezo-electric valve.

In some aspects, a directional flow channel intersects an output channels at a junction. In certain aspects, the detector is located on at least one channel that is not an output channel. In some aspects, the device comprises a confirmatory laser. In certain aspects, the confirmatory laser is located on at least one channel that is not an input channel. In further aspects, the system comprises a second detector. In still further aspects, at least one channel is in fluidic communication with a filter.

In various aspects, devices are provided for detecting a rare particle in a fluid sample, the devices comprising: an input channel; a first output channel; a second output channel; a detector configured to detect the presence or absence of a particle in a portion of the fluid sample; a mechanism for directing the flow of the portion from the input channel to the first output channel, the second output channel, or a combination thereof based on the presence or absence of the particle; and a filter in fluidic communication with the first output channel. In some aspects, the filter comprises an array of apertures. In certain aspects, a smallest dimension of each aperture in the array is smaller than a smallest dimension of the particle.

In various aspects, devices are provided for detecting a rare particle in a fluid sample, the devices comprising: (a) at least one sample input channel; (b) at least two output channels, wherein at least one of the two output channels is in fluidic communication with an array of apertures; (c) at least one detector capable of detecting one or more rare particles in an aliquot of the fluid sample; and (d) a mechanism for sorting the one or more rare particles by directing the flow of aliquots containing the one or more rare particles through a first output channel.

In some aspects, the device comprises a first output channel and a second output channel. In certain aspects, the mechanism directs the flow of the aliquots into the second output channel if the aliquot does not contain a rare particle. In certain aspects, the mechanism for sorting comprises an electrode, a magnetic element, an acoustic element, or an electro-actuated element.

In some aspects, the array of apertures is disposed between an input channel and an output channel. In certain aspects, the array of apertures is in the same plane as an input channel and an output channels. In further aspects, the array of apertures is disposed within the first output channel. In still further aspects, the array of apertures is disposed in a chamber in fluidic communication with the first output channel. In some aspects, the array of apertures is configured so that the rare particles cannot pass through the apertures but at least one other particle is capable of passing through the apertures. In certain aspects, the array of apertures is configured so that the rare particles are capable of passing through the apertures but at least one other particle cannot pass through the apertures. In further aspects, the array of apertures comprises greater than 1000 apertures.

In certain aspects, the detector is selected from the group consisting of a camera, an electron multiplier, a charge-coupled device (CCD) image sensor, a photomultiplier tube (PMT), an avalanche photodiode (APD), a single-photon avalanche diode (SPAD), a silicon photomultiplier (SiPM), and a complementary metal oxide semiconductor (CMOS) image sensor.

In various aspects, integrated systems are provided for performing an assay, the systems comprising: a fluid sample comprising a particle, wherein the particle comprises a marker; an input channel; a first output channel; a second output channel; a first detector configured to detect the presence or absence of the particle in a portion of the fluid sample, the portion disposed within the input channel; a mechanism for directing the flow of the portion from the input channel to the first output channel based on the presence or absence of the particle; a micro-cavity in fluidic communication with the first output channel and configured to trap the particle; and a second detector configured to detect the presence or absence of the marker in the micro-cavity.

Microfluidic Chip Design and Fabrication

The microfluidic chip can be fabricated to provide for an efficient active sorting scheme and subsequent purification (e.g., purification chamber) scheme. The microfluidic chip can be composed of two layers on a silicon master and can be fabricated with one-step replica molding into polydimethylsiloxane (PDMS). The microfluidic chip can be finished with bonding to a glass substrate.

Figure 5:
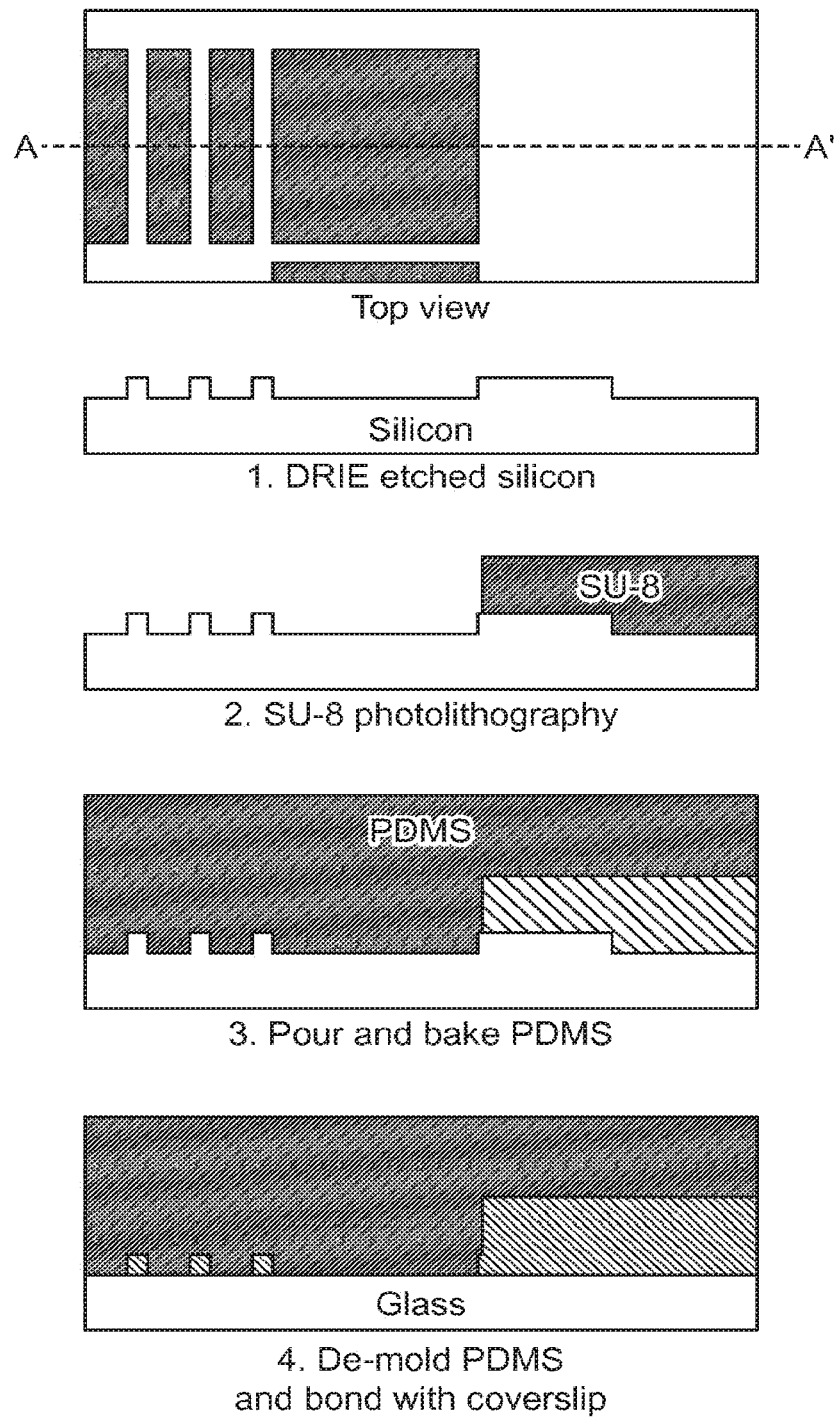
FIG. 5 illustrates an example of the process flow for microfabrication of the eDAR microfluidic chip according to an aspect of the present disclosure.

In some aspects, the silicon master can be fabricated using two photolithography processes (FIG. 5). The features can be designed using standard software (e.g., AutoCAD, Autodesk, San Rafael, CA), and can be written on a chrome mask. In these cases, positive resist lithography and deep reactive ion etching (DRIE) can be used to form the first layer (FIG. 5). The first layer can be the micro-filter feature. In some aspects, the positive photo resist (e.g., AZ 1512) is achieved by a process that can include a DRIE process. The DRIE process can achieve a depth (e.g., 4.5-5 µm) suitable for various features.

In some aspects, the second layer of the eDAR microfluidic chip features can be fabricated using a negative photoresist (e.g., SU-8-3050 from MicroChem, Newton, MA), and the height of the feature can be controlled (e.g., 50 µm). The master can be silanized using, for example, tridecafluoro-1,1,2,2-tetrahydrooctyl-1-trichlorosilane (Sigma-Aldrich, St. Louis, MO). The silanized master and silicon wafer can be coated with uncured PDMS and baked (e.g, for 2 hours at 70° C.). In some aspects, the piece of PDMS with the desired micro-features can be peeled off the silicon master, and then bonded with a piece of cover glass using the standard process of plasma oxidation to complete the fabrication of the eDAR microfluidic chip.

The microfluidic chip can contain specialized regions including, a staining region, a photobleaching region, an imaging region, and additional regions. In some aspects, the regions can be the same region used for at least one purpose. In other cases, the regions can be different regions use for one purpose. In other cases, the regions can be different regions use for at least one purpose. Each region can be used for more than one purpose. In some aspects, the eDAR microfluidic chip includes an integrated filtration area fabricated by standard lithography methods. In some aspects, the microfluidic chip can have two integrated functional areas, the eDAR sorting area and a slit-structure based filtration unit.

Channels in the Microfluidic Chip

The disclosure provided herein describes an apparatus for detecting an analyte (e.g., rare particle) in a fluid sample, the apparatus comprises: (a) at least a first input channel; (b) at least two exit channels; (c) at least one detector capable of detecting one or more rare particles in an aliquot of the biological fluid; (d) a mechanism for directing the flow of the aliquot; and (e) a ranking device capable of assigning a value to the aliquot based on the presence, absence, identity, composition, or quantity of the rare particles in the aliquot, wherein the digital processor (e.g, computer) is in communication with the detector and the mechanism for directing the flow of the aliquot.

In some aspects, the apparatus provided herein can comprise a flow channel enclosed by walls and/or microfabricated on a substrate, with design features to minimize inadvertent damage to analytes (e.g., rare cells). Reducing inadvertent damage of rare cells can reduce the rate of false-negatives that cause erroneous patient diagnosis or prognosis. The flow channel can further comprise channels with hydrodynamically designed apertures to exclude biological cells with minimal stress or damage. The flow channel is as described in US Patent Application Nos. 2007/0037172 and 2008/0248499. Such channels, referred to in the aforementioned patent applications as channels with one-dimensional ("1-D") apertures, reduce the hydrodynamic pressure experienced by the cells during the cell exclusion process and therefore reduce the likelihood of cell lysis Channels with 1-D apertures can be strategically arranged in an array according to "effusive filtration" configuration as described in US Patent No. 2008/0318324 to further re-direct, partition, dampen, or disperse the flow, consequently reducing the force of impact experienced by the cells at the moment of exclusion. The walls that enclose the flow channel can be fabricated using a UV-curing process in accordance with the procedures described in PCTPCT/US2009/02426, from a biocompatible substrate material that is a medical-device grade polymer, so that the eDAR apparatus can be in compliance with regulations governing medical device manufacturing.

The main channel in the sorting area, which can be used to introduce fluid into the sorting junction, can have a particular height (e.g., 50 µm) and a particular width (e.g., 150 µm). In most cases, the other channels (e.g., four) can have a particular height (e.g, 50 µm) and a particular width (e.g, 200 µm) The slit-structure based filters in the filtration unit can have a particular height (e.g, 5 µm) and a particular width (e.g., 5 µm) The microfluidic chip can contain up to and can include 50,000 slits in the slit structure.

In some aspects, the eDAR apparatus can further comprise channels for channeling said aliquots based on said ranking. The channels can be treated with anticoagulant compounds, compounds that preferentially bind to the analytes (e.g., rare bioparticles), compounds that prevent agglomeration of rare bioparticles or their combinations.

In some aspects, the eDAR apparatus provided herein can comprise a plurality of flow channels, including one or more input flow channels (e.g., channels that bring an aliquot to a detection volume) and one or more output channels (e.g., channels that take an aliquot away from a detection volume. In some aspects, the eDAR apparatus as provided herein can comprise a combination of at least about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, or more input channels and at least about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, or more output channels. In some aspects, the eDAR apparatus as provided herein can comprise a combination of at least 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, or more input channels and at least 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, or more output channels. In some aspects, an apparatus can comprise multiple flow channels connecting to the main channel to inject additional fluid to alter the local velocity.

In some aspects, a fluid is delivered from a channel that is part of a microfluidic chip to a chamber that is in fluidic communication with the channel but is external to the microfluidic chip. In some aspects, the chamber is a vial. In other aspects, the chamber is a single well or a well in a well plate. In further aspects, the chamber is a microcentrifuge tube. In further aspects, the chamber is a microcentrifuge tube, wherein the microcentrifuge tube is an Eppendorf tube. Any suitable structure can be used for the vial and one of ordinary skill in the art could readily identify suitable chambers for use with the present disclosure.

In some aspects, a fluid is delivered from a channel to a chamber that is in fluidic communication with the channel via a tube or other suitable structure for transporting a fluid. The tube can comprise a material constructed from a biocompatible polymer. In other aspects, the chamber can be in fluidic communication with the channel via a capillary tube, such as a fused silica capillary tube, such as is used e.g., for performing capillary electrophoresis. Other types of tubing suitable for bringing a channel into fluidic communication with a chamber will be readily apparent to one of ordinary skill in the art.

As used herein, the term "in fluidic communication with" (and variations thereof) refers to the existence of a fluid path between components. Being in fluidic communication neither implies nor excludes the existence of any intermediate structures or components. Two components can be in fluidic communication even if in some instances the path between them is blocked and/or fluid is not flowing between them. Thus, intermittent fluid flow is contemplated in certain aspects where there is fluidic communication.

In some aspects, an apparatus provided herein can comprise a flow channel or chamber enclosed by walls fabricated from materials including, but not limited to, polymeric materials (polydimethylsiloxane (PDMS), polyurethanemethacrylate (PUMA), polymethylmethacrylate (PMMA), polyethylene, polyester (PET), polytetrafluoroethylene (PTFE), polycarbonate, parylene, polyvinyl chloride, fluoroethylpropylene, lexan, polystyrene, cyclic olefin copolymers, polyurethane, polyestercarbonate, polypropylene, polybutylene, polyacrylate, polycaprolactone, polyketone, polyphthalamide, cellulose acetate, polyacrylonitrile, polysulfone, epoxy polymers, thermoplastics, fluoropolymer, and polyvinylidene fluoride, polyamide, polyimide), inorganic materials (glass, quartz, silicon, GaAs, silicon nitride), fused silica, ceramic, glass (organic), metals and/or other materials and combinations thereof.

In some aspects, wall materials can be fabricated of porous membranes, woven or non-woven fibers (such as cloth or mesh) of wool, metal (e.g., stainless steel or Monel), glass, paper, or synthetic (e.g., nylon, polypropylene, polycarbonate, parylene, and various polyesters), sintered stainless steel and other metals, and porous inorganic materials such as alumina, silica or carbon.

In some aspects, the apparatus provided herein can comprise a flow channel or chamber that has been pre-treated with a chemical or biological molecule. For example, a channel or chamber can be treated with an anticoagulant compound to prevent or reduce the association of an analyte (e.g., rare particle or cell) in the fluid sample, a compound that preferentially binds to an analyte (e.g., rare particle or cell), or a compound that prevents or reduces the agglomeration or aggregation of a analyte (e.g., rare particle or cell) in the fluid sample.

In some aspects, the channel or chamber surfaces can be treated with anticoagulant compounds, compounds that preferentially bind to circulating tumor cells, or compounds that prevent the sticking of cells.

In some aspects, a channel or chamber surface can be modified chemically to enhance wetting or to assist in the adsorption of select cells, particles, or molecules. Surface-modification chemicals can include but not limited to silanes such as trimethylchlorosilane (TMCS), hexamethyldisilazane (HMDS), (Tridecafluoro-1,1,2,2-tetrahydrooctyl)trichlorosilane, chlorodimethyloctylsilane, Octadecyltrichlorosilane (OTS) or γ-methyacryloxypropyltrimethyoxy-silane; polymers such as acrylic acid, acrylamide, dimethylacrylamide (DMA), 2-hydroxyethyl acrylate, polyvinylalcohol (PVA), poly(vinylpyrrolidone (PVP), poly(ethylene imine) (PEI), Polyethylene glycol (PEG), epoxy poly(dimethylacrylamide (EPDMA), or PEG-monomethoxyl acrylate; surfactants such as Pluronic surfactants, Poly(ethylene glycol)-based (PEG) surfactants, sodium dodecylsulfate (SDS) dodecyltrimethylammonium chloride (DTAC), cetyltriethylammonium bromide (CTAB), or Polybrene (PB); cellulose derivatives such as hydroxypropylcellulose (HPC), or hydroxypropylmethylcellulose (HPMC); amines such as ethylamine, diethylamine, triethylamine, or triethanolamine, fluorine-containing compounds such as those containing polytetrafluoroethylene (PTFE) or Teflon.

Filtration

The eDAR apparatus provided herein can further comprise a filter element. In some aspects, the filter element can be in the form of micro-posts, micro-barriers, micro-impactors, micro-sieves, channels with apertures smaller than bioparticles, channels with apertures such that a bioparticle can be prevented from entering an aperture but fluid can be allowed to continue to flow around the bioparticle through the aperture ("1-D channels"), microbeads, porous membranes, protrusions from the walls, adhesive coating, woven or non-woven fibers (such as cloth or mesh) of wool, metal (e.g., stainless steel or Monel), glass, paper, or synthetic (e.g., nylon, polypropylene, polycarbonate, parylene, and polyester), sintered stainless steel or other metals, or porous inorganic materials such as alumina, silica.

In some aspects, an array of apertures in the filter element is configured so that a particle of interest, such as a rare particle or cell, cannot pass through the apertures of the filter element, while at least one other particle is capable of passing through the apertures of the filter element. In other aspects, an array of apertures in the filter element is configured so that a particle of interest, such as a rare particle or cell, is capable of passing through the apertures of the filter element, while at least one other particle is incapable of passing through the apertures of the filter element.

Figure 10:
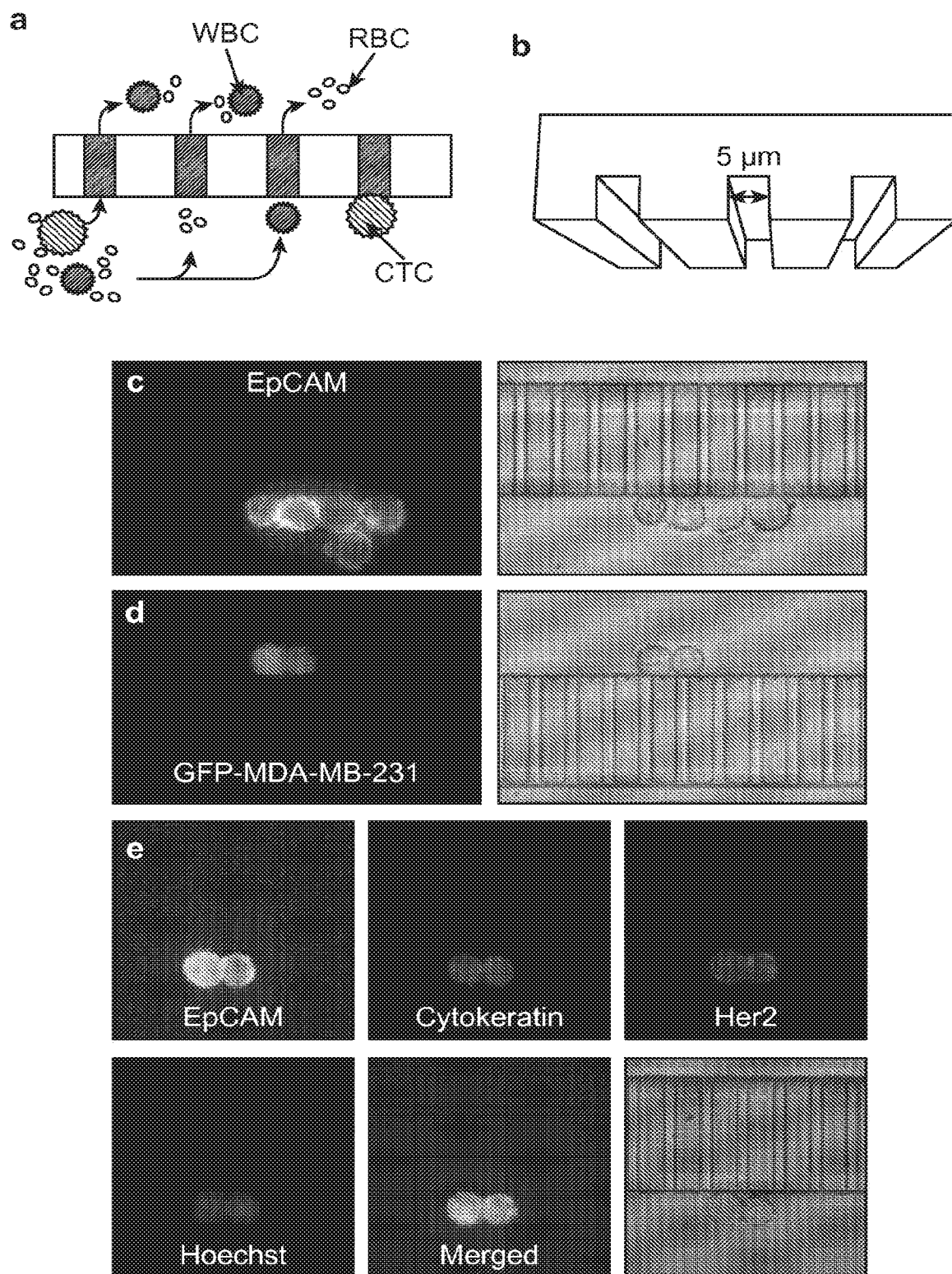
FIG. 10 shows the microslits and multicolor fluorescence imaging of captured CTCs according to an aspect of the present disclosure.

In some aspects, the eDAR microfluidic chip can be fabricated with microslits (FIG. 10a). The microslits can be used to capture rare cells without retaining any additional non-specific particles (e.g., red blood cells, RBCs). The size of the microslits can vary. In some aspects, the height of the microslits can be less than or equal to about 0.1 µm, 0.5 µm, 1 µm, 5 µm, 10 µm, 15 µm, 20 µm, 25 µm, 30 µm, 35 µm, 40 µm, 50 µm, 75 µm or 100 µm tall. In some aspects, the height of the microslits can be in the range of about 0.1-5 µm, 1-10 µm, 5-15 µm, 10-30 µm, 15-40 µm, 20-50 µm, 30-75 µm and 50-100 µm tall. In some aspects, the width of the microslits can be less than or equal to about 0.1 µm, 0.5 µm, 1 µm, 5 µm, 10 µm, 15 µm, 20 µm, 25 µm, 30 µm, 35 µm, 40 µm, 50 µm, 75 µm or 100 µm tall. In some aspects, the width of the microslits can be in the range of about 0.1-5 µm, 1-10 µm, 5-15 µm, 10-30 µm, 15-40 µm, 20-50 µm, 30-75 µm and 50-100 µm tall. For example, the microslits can have a height of 5 µm and width of 5 µm (FIG. 10b).

In some aspects, the height of the microslits can be less than or equal to 0.1 µm, 0.5 µm, 1 µm, 5 µm, 10 µm, 15 µm, 20 µm, 25 µm, 30 µm, 35 µm, 40 µm, 50 µm, 75 µm or 100 µm tall. In some aspects, the height of the microslits can be in the range of 0.1-5 µm, 1-10 µm, 5-15 µm, 10-30 µm, 15-40 µm, 20-50 µm, 30-75 µm and 50-100 µm tall. In some aspects, the width of the microslits can be less than or equal to 0.1 µm, 0.5 µm, 1 µm, 5 µm, 10 µm, 15 µm, 20 µm, 25 µm, 30 µm, 35 µm, 40 µm, 50 µm, 75 µm or 100 µm tall. In some aspects, the width of the microslits can be in the range of 0.1-5 µm, 1-10 µm, 5-15 µm, 10-30 µm, 15-40 µm, 20-50 µm, 30-75 µm and 50-100 µm tall.

In some aspects, microfluidic chips can be prepared with 100, 200, 300, 400, 500, 600, 700, 800, 900, 1000, 5000, 20,000, 30,000, 40,000, or 50,000 apertures or microslits. In other aspects, microfluidic chips can be prepared with greater than 100, greater than 200, greater than 300, greater than 400, greater than 500, greater than 600, greater than 700, greater than 800, greater than 900, greater than 1000, greater than 5000, greater than 20,000, greater than 30,000, greater than 40,000, or greater than 50,000 apertures or microslits. In some aspects, pressures can be lower for microfluidic chips with more microslits. For example, the eDAR microfluidic chip with 20,000 slits required a pressure of less than 4 psi on the two side-buffer channels to balance the hydrodynamic switching process. In some aspects, the lower pressure across the microfilter can minimize the stress upon and deformation of the isolated rare cell.

Microslits can be used as a source of filtration. In some aspects, the microslits can be fabricated from any material that allows for sorting and does not cause aberrations during imaging (e.g., PDMS) and bonded with a piece of coverslip for use with imaging systems (FIGS. 10c and 10D). In some aspects, the microslits can be microfilters.

In some aspects, use of the microslits for filtration purposes can improve imaging accuracy and enumeration of trapped cells. In some aspects, the microslits can increase the speed and efficiency of a second round of labeling on trapped rare cells. For example, two cancer cells labeled with anti-EpCAM-PE can be trapped on the microslit (FIG. 10e). The cells can be fixed, permeabilzed, and labeled with anti-Cytokeratin-Alexa488, anti-CD45-Alexa700, anti-Her2-Alexa647 and Hoechst.

Hydrodynamic Sorting

Two key factors that contribute to the features and performance of the eDAR platform are, (1) an efficient and active sorting scheme and a (2) subsequent efficient purification (e.g., purification chamber) scheme. The analytical performance of the microfluidic chip and hydrodynamic switching mechanisms can be optimized for a particular recovery efficiency (e.g., 95%), a particular false positive rate (e.g., 0) and a particular throughput (e.g., 4.8 mL of whole blood per hour).

In some aspects, the mechanism for directing the flow directs the flow of an aliquot containing a rare particle into one of a plurality of exit channels depending on the identity, composition, or quantity of the rare particle. The mechanism for directing the flow of the aliquot can either be into a first exit channel, if the aliquot contains a rare particle, or a second exit channel, if the aliquot does not contain a rare particle.

In some aspects, the mechanism for directing the flow of the aliquot can comprise an electrode, a magnetic element, an acoustic element, an electro-actuated element, an electric field, a piezo-electric valve, or a magnetic field. In other cases, the mechanism for directing the flow of the aliquot can comprise one or more electro-actuated valves or pistons, wherein the valves or pistons control the flow of a liquid in at least a first directional flow channel that intersects with the first input channel and the two exit channels at a first junction.

In some aspects, the apparatus provided herein can comprise one or more electrodes for tracking and/or manipulating the trajectory or flow of a particle, aliquot, or fluid sample. In some aspects, the apparatus provided herein can comprise one or more electrodes for tracking and/or manipulating the trajectory or flow of an ensemble, or a group, of particles or aliquots. In this case, the electrode can enhance the separation of an aliquot based on phenomena such dielectrophoresis or electrowetting.

In other cases, the apparatuses provided herein can further comprise a magnetic element for the separation of a rare particle (e.g., cell) bound to or bound by a magnetic particle. In other cases, the apparatuses provided herein can further comprise a magnetic element for the separation of an ensemble or group of rare particles (e.g., cells) bound to or bound by at least one magnetic particle. In some aspects, the magnetic element can enhance the separation of an aliquot, particle, or cell based on the magnetic susceptibility of the cells or the micro-magnetic or nano-magnetic particles attached to a particle or cell. In some aspects, the magnetic element can enhance the separation of an ensemble or a group of particles, or cells based on the magnetic susceptibility of the cells or the micro-magnetic or nano-magnetic particles attached to at least one particle or cell.

The eDAR apparatus can have a second line-confocal detection window located on the collection side to monitor the efficiency of the hydrodynamic switching in real time. In some aspects, the eDAR apparatus can be paired with confocal imaging.

Figure 4:
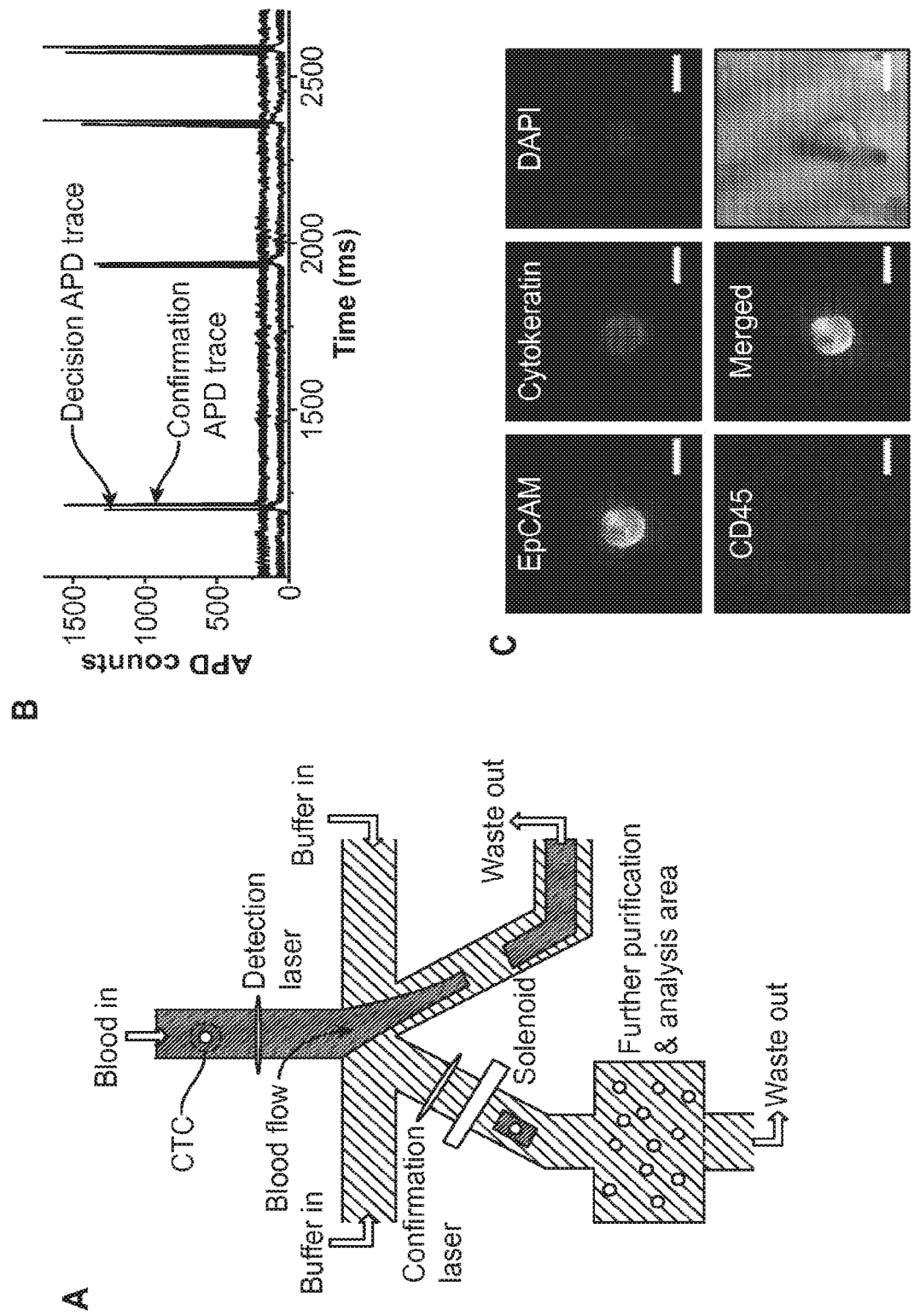
FIG. 4 is an overview of eDAR according to an aspect of the present disclosure.

In some aspects, the hydrodynamic switch can be controlled by a solenoid and the pressure drop in the two side buffer lines. A solenoid can be located in the rare cell collection channel. In some aspects, this solenoid is in the closed position on the left and the "negative" aliquots flow into the waste channel on the right (FIG. 4A). When the solenoid is opened, a pressure drop between the two side channels that contain buffer switches the blood flow from the waste channel to the collection side. This switch can occur in less than 10 milliseconds (e.g., 2-3 ms) to collect rare particles (e.g., cells).

Figure 6:
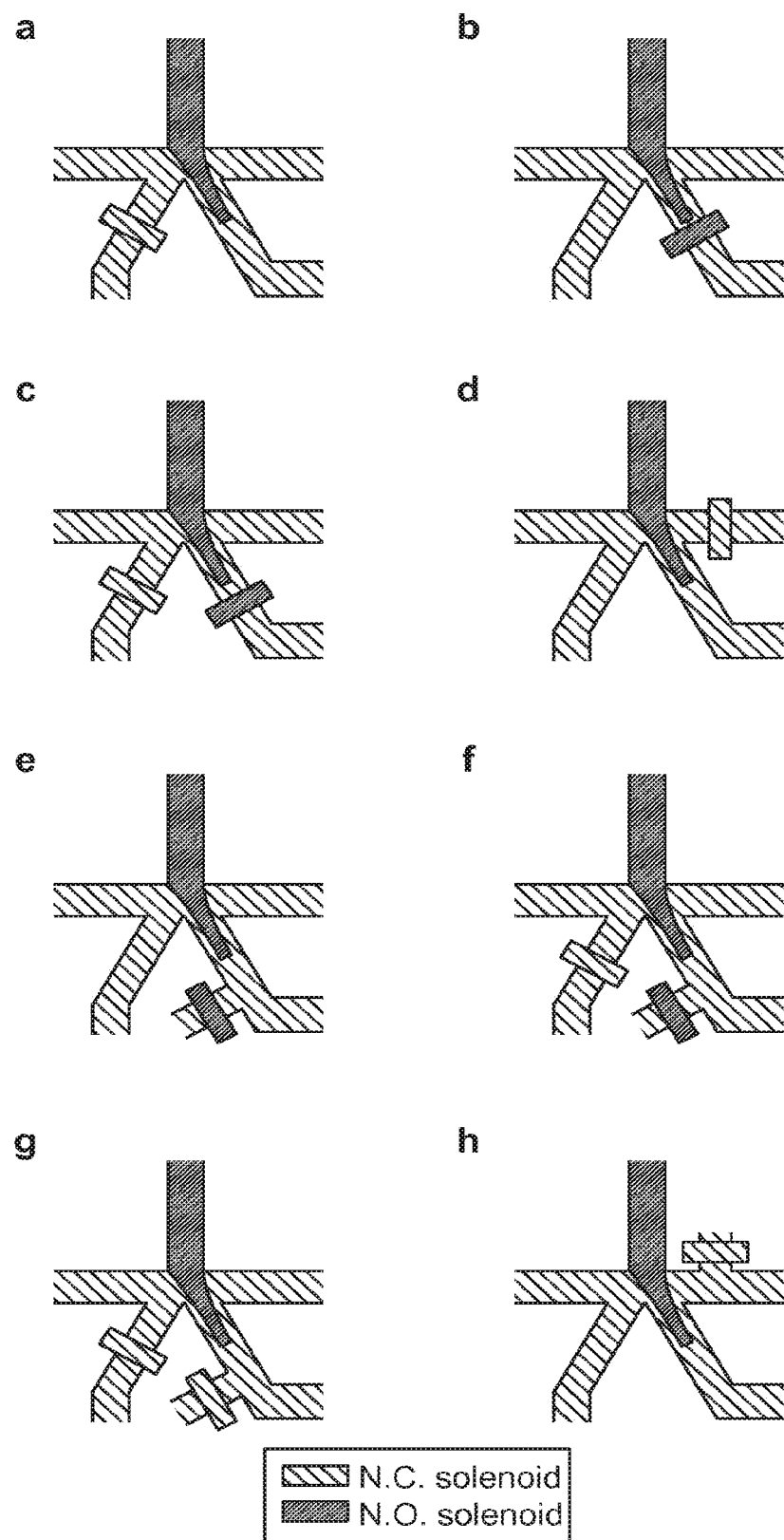
FIG. 6 illustrates eight exemplary hydrodynamic sorting schemes.

In some aspects, various hydrodynamic sorting schemes can be used. The disclosure provides for eight different hydrodynamic sorting schemes (FIG. 6). The fluid sample (e.g., blood) can be injected from the main channel, shown as the dark black flow. Buffer (light grey color in the microfluidic chip) can flow in the two side channels, rare cells can be collected to the bottom left channel, and the waste can be directed to the bottom right channel. The rectangular blocks represent the solenoid (see "solenoids"). The solenoid can be set to be normally open (N.O.) or normally closed (N.C.), as indicated by a dark grey or light grey block, respectively (FIG. 6).

Channels of the microfluidic chip may intersect at junctions. In some aspects, one channel intersects with a different channel at a junction. In some aspects, one channel intersects with more than one different channels at a junction. In some aspects, one channel intersects with 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 different channels at a junction. In some aspects, more than one channel intersects with a different channel at a junction. In some aspects, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 different channels intersect with one different channel at a junction.

Channels of the microfluidic chip may not intersect at junctions. In some aspects, one channel intersects with a different channel at a location on the microfluidic chip that is not a junction. In some aspects, one channel intersects with more than one different channels at a location on the microfluidic chip that is not a junction. In some aspects, one channel intersects with 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 different channels at a location on the microfluidic chip that is not a junction. In some aspects, more than one channel intersects with a different channel at a location on the microfluidic chip that is not a junction. In some aspects, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 different channels intersect with one different channel at a location on the microfluidic chip that is not a junction.

Solenoids and Regulation of Flow

The eDAR apparatus includes solenoids to control flow of fluid and hydrodynamic sorting schemes. In some aspects, solenoids can be pistons. For example, solenoid pistons are subcomponents of electro-actuated solenoid valves. In some aspects, the electro-actuated solenoid valves can be piezoelectric valves. In some aspects, solenoid pistons can be embedded in the apparatus by molding. In some aspects, solenoids can be valves. For example, the embedded solenoid pistons may be replaced by solenoid valves in fluidic communication via tubings.

In some aspects, the eDAR apparatus can contain one solenoid. In other cases, the eDAR apparatus can contain more than one solenoid. For example, the eDAR apparatus can contain greater than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50 solenoids. In some aspects, at least one solenoid can be open. For example, an open solenoid can be used to allow flow to pass from one part of the microfluidic device to a different part of the microfluidic device. In some aspects, greater than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50 solenoids can be open. In some aspects, one part can be the sample entry point. In some aspects, one part can be the waste channel. In some aspects, one part can be a sorting chamber. In some aspects, at least one solenoid can be normally open (N.O.) In some aspects, greater than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50 solenoids can be normally open.

In some aspects, solenoids can be closed. For example, a closed solenoid can be used to prevent flow from passing from one part of the microfluidic device to a different part of the microfluidic device. In some aspects, at least one solenoid can be closed. In some aspects, greater than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50 solenoids can be closed. In some aspects, one part can be the sample entry point. In some aspects, one part can be the waste channel. In some aspects, one part can be a sorting chamber. In some aspects, at least one solenoid can be normally closed (N.C.) In some aspects, greater than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50 solenoids can be normally closed.

In some aspects, solenoids can be switched from open to closed. For example, closing an open solenoid can be used to prevent flow from passing from one part of the microfluidic device to a different part of the microfluidic device. In some aspects, at least one solenoid can be switched from open to closed. In some aspects, greater than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50 solenoids can be switched from open to closed. In some aspects, one part can be the sample entry point. In some aspects, one part can be the waste channel. In some aspects, one part can be a sorting chamber.

In some aspects, solenoids can be switched from closed to open. For example, opening a closed solenoid can be used to allow fluid to pass from one part of the microfluidic device to a different part of the microfluidic device. In some aspects, at least one solenoid can be switched from closed to open. In some aspects, greater than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50 solenoids can be switched from closed to open. In some aspects, one part can be the sample entry point. In some aspects, one part can be the waste channel. In some aspects, one part can be a sorting chamber.

In some aspects, the structure of the fluidic microfluidic chip and the corresponding scheme of the hydrodynamic sorting that can be used for eDAR are shown in FIG. 6. The position of the solenoid can be marked when there are outlets or inlets on a single channel. For example in FIG. 6F, the position of the second solenoid can be "center waste," meaning that it is on the center outlet of the waste collection channel. In every scheme, except that shown in FIG. 6G, when the "positive" events can be detected, the DC voltage applied on the solenoids can be changed to trigger the sorting, and after a certain period of time can be returned to the normal state. In some aspects, 4 individual steps can be used to control the sorting (e.g., scheme shown in FIG. 6G). Both solenoids can be closed and the fluid can flow to the waste channel. The sorting can be triggered which could open the solenoid on the collection side to perform the switch-over step. The other solenoid can be opened to perform the switchback step after the cell is collected. Both solenoids can be closed at the same time after the fluid flow was completely switched back to revert to the normal state. A summary of the fluidic configuration and performance of eight different hydrodynamic sorting schemes described herein is depicted in Table 1 (below). In some aspects, two solenoids can be used (e.g., schemes shown in FIGS. 6C, 6E, and 6G).

TABLE 1

Summary of the fluidic configuration and performance of 8 sorting schemes.

| Scheme | Position | Normal state | Left pressure (psi) | Right pressure (psi) | Switch over time (ms) | Switch back time (ms) |
|---|---|---|---|---|---|---|
| a | Collection | Closed | Low | High | ~2-3 | ~15-25 |
| b | Waste | Open | High | Low | ~15-20 | ~2-3 |
| c | Collection | Closed | Low | High | ~4-5 | ~10 |
|   | Waste | Open | | | | |
| d | Right Buffer | Close | Low | High | ~3 | ~40 |
| e | Waste | Open | High | Low | ~25 | ~2 |
| f | Collection Center Waste | Closed Open | Low | High | ~25 | ~5-6 |
| g | Collection Center Waste | Closed Closed | Low | High | ~2-3 | ~2-3 |
| h | Center Right Buffer | Closed | Low | High | ~2-3 | ~2-3 |

In some aspects, an off-chip solenoid can be used. The off-chip solenoid can be closed for most of the method. To open the off-chip solenoid, voltage (e.g., 5V DC voltage) can be applied. The off-chip solenoid can open rapidly (e.g., less than or equal to three milliseconds). Where an off-chip solenoid is used, the preparation of the microfluidic chip can be modified and solenoids can be connected with microchannels. In some aspects, an on-chip solenoid can be used. The on-chip solenoid can be closed for most of the method. To open the on-chip solenoid, voltage (e.g., 5V DC voltage) can be applied. The on-chip solenoid can open rapidly (e.g., less than or equal to three milliseconds). Where an on-chip solenoid is used, the preparation of the microfluidic chip can be modified and solenoids can be connected with microchannels.

For example, in this scheme, an off-chip solenoid is used. The labeled fluid sample can be injected into the top channel of the microfluidic chip using a syringe pump (FIG. 7a). Two side channels, where buffer flows through, can be used to control the active sorting step. Two ports are located on the right-side channel, and both are connected to a pressurized buffer source. The off-chip solenoid can be connected to the port near the sorting junction to control the hydrodynamic switch. The switching process using an off-chip solenoid can be stable and can maintain stability through $10^5$ on-off cycles.

In some aspects, an in-line solenoid can be placed on the buffer line to prevent the fluid sample from contacting the solenoid. This can eliminate the possibility of sample decay and cross-contamination. There can be a constant flow of buffer in the rare cell collection channel during use of the eDAR apparatus and method. The on-chip solenoid can improve the efficiency of the subsequent purification (e.g., purification chamber) step and can prevent the formation of aggregates of cells.

In some aspects, the flow of fluid in the eDAR apparatus can be regulated with one of the following either upstream or downstream of the detection volume: a solenoid, a valve, a bubble, an electric field, a magnetic field, an optical field, a pneumatic pressure source, a solid particle, a membrane, an immiscible droplet, a gravitational differential, or a coating to alter surface tension of the channel. The flow can be stopped, decelerated, or accelerated as the cells traverse through the detection volume.

In some aspects, continuous flow of the fluid sample through a flow channel can be maintained during detection. In some aspects, the individual aliquots may not be physically separated, but rather can be defined by an optical detection step and/or a sorting step.

For example, the flow can be directed into the channel that can be used to collect the waste (FIG. 7b). There can be two channels after the sorting junction. The left channel can collect positive aliquots, deliver them to the filtration and collection area for further purification (e.g., purification chamber); the right channel collects waste (e.g., the negative aliquots). In this case, no voltage is applied the solenoid when aliquots are ranked as "negative" and remains closed (FIG. 7b). The change in flow pattern can occur after an initial pressure drop between the No. 1 and 3 buffer sources (FIG. 7a). A positive event can be detected by the first detection window. In this case, a DC voltage (e.g., 5V) can be applied to the solenoid to open the buffer flow from the buffer reservoir (e.g., No. 2). The decreased flow resistance of the buffer channel on the right side can generate a higher flow rate. The fluid flow can be pushed from the right side to the left to collect the positive aliquot (FIG. 7c). The aliquot can be collected and confirmed by the second detection window. In some aspects, the solenoid can be closed to switch the fluid flow back to the waste collection channel (FIG. 7d). The time required for the switch-over and back can be less than 20 milliseconds, in an exemplary case the time is or between 2-3 milliseconds (Table 1 and FIG. 8; frame rate=1,918 frames per second). In some aspects, the conditions used can be repeated for more than $10^5$ on-off cycles.

In some aspects, the flow can be delivered by, for example, methods and devices that induce hydrodynamic fluidic pressure, which includes but is not limited to those that operate on the basis of mechanical principles (e.g., external syringe pumps, pneumatic membrane pumps, vibrating membrane pumps, vacuum devices, centrifugal forces, and capillary action); electrical or magnetic principles (e.g., electroosmotic flow, electrokinetic pumps piezoelectric/ultrasonic pumps, ferrofluidic plugs, electrohydrodynamic pumps, and magnetohydrodynamic pumps); thermodynamic principles (e.g., gas bubble generation/phase-change-induced volume expansion); surface-wetting principles (e.g., electrowetting, chemically, thermally, and radioactively induced surface-tension gradient).

In yet other cases, the fluid can be delivered or channeled by a fluid drive force provided by gravity feed, surface tension (like capillary action), electrostatic forces (electrokinetic flow), centrifugal flow (substrate disposed on a compact disc and rotated), magnetic forces (oscillating ions causes flow), magnetohydrodynamic forces and a vacuum or pressure differential.

In some aspects, fluid flow control devices, such as those enumerated with regard to methods and devices for inducing hydrodynamic fluid pressure or fluid drive force, can be coupled to an input port or an output port of the present subject matter. In some aspects, multiple ports are provided at either or both of the inlet and outlet and one or more ports are coupled to a fluid flow control device.

Transit Time

The analyte (e.g., rare cell or circulating tumor cell (CTC)) can flow from the first detection window to the second detection window. The time that can elapse between recording of the decision APD peak in the first window and detection of the confirmation signal can be the transit time for sorting an analyte. In some aspects, the transit time can vary. In some aspects, the liner flow rate can affect the transit time. In some aspects, the laminar flow of the microchannel can affect the transit time. In some aspects, the volumetric flow rate can be set to 40 µL/min (FIG. 9b). In some aspects, the volumetric flow rates can be about 1 µL/min, 2 µL/min, 3 µL/min, 4 µL/min, 5 µL/min, 6 µL/min, 7 µL/min, 8 µL/min, 9 µL/min, 10 µL/min, 11 µL/min, 12 µL/min, 13 µL/min, 14 µL/min, 15 µL/min, 16 µL/min, 17 µL/min, 18 µL/min, 19 µL/min, 20 µL/min, 21 µL/min, 22 µL/min, 23 µL/min, 24 µL/min, 25 µL/min, 30 µL/min, 35 µL/min, 40 µL/min, 45 µL/min, 50 µL/min, 55 µL/min, 60 µL/min, 65 µL/min, 70 µL/min, 75 µL/min, 80 µL/min, 85 µL/min, 90 µL/min, 95 µL/min, 100 µL/min, or 200 µL/min.

In some aspects, the flow rate can be within the range of about 1 µL/min-5 µL/min, 3 µL/min-10 µL/min, 5 µL/min-15 µL/min, 10 µL/min-20 µL/min, 15 µL/min-30 µL/min, 20 µL/min-40 µL/min, 30 µL/min-50 µL/min, 40 µL/min-60 µL/min, 50 µL/min-70 µL/min, 60 µL/min-80 µL/min, 70 µL/min-90 µL/min, 80 µL/min-100 µL/min, 90 µL/min-100 µL/min or 90 µL/min-200 µL/min. In other cases, the volumetric flow rate can be set to 80 µL/min (FIG. 9b).

In some aspects, the volumetric flow rates can be 1 µL/min, 2 µL/min, 3 µL/min, 4 µL/min, 5 µL/min, 6 µL/min, 7 µL/min, 8 µL/min, 9 µL/min, 10 µL/min, 11 µL/min, 12 µL/min, 13 µL/min, 14 µL/min, 15 µL/min, 16 µL/min, 17 µL/min, 18 µL/min, 19 µL/min, 20 µL/min, 21 µL/min, 22 µL/min, 23 µL/min, 24 µL/min, 25 µL/min, 30 µL/min, 35 µL/min, 40 µL/min, 45 µL/min, 50 µL/min, 55 µL/min, 60 µL/min, 65 µL/min, 70 µL/min, 75 µL/min, 80 µL/min, 85 µL/min, 90 µL/min, 95 µL/min, 100 µL/min, or 200 µL/min.

In some aspects, the flow rate can be within the range of 1 µL/min-5 µL/min, 3 µL/min-10 µL/min, 5 µL/min-15 µL/min, 10 µL/min-20 µL/min, 15 µL/min-30 µL/min, 20 µL/min-40 µL/min, 30 µL/min-50 µL/min, 40 µL/min-60 µL/min, 50 µL/min-70 µL/min, 60 µL/min-80 µL/min, 70 µL/min-90 µL/min, 80 µL/min-100 µL/min, 90 µL/min-100 µL/min or 90 µL/min-200 µL/min. A higher flow rate can be used to achieve a lower transit time (FIG. 9c).

Detection

The disclosure provides an apparatus for eDAR using a microfluidic chip that can be equipped with a detection system. In some aspects, the detection system can include a line-confocal detection scheme. In the line-confocal detection scheme, two laser sources (e.g., 488 and 633 nm) form detection windows (e.g., two) using a series of dichroic mirrors, cylindrical lens and beam splitters. The first detection window can have two laser beams simultaneously overlapping and can be used detect the fluorescence signals from the labeled rare cells (e.g., CTCs). The second detection window can be used to confirm the identity of the rare cells, or lack of rare cells, in the sorted aliquots. The second detection window can further be used to monitor the sorting efficiency.

In some aspects, two rare particles can be detected simultaneously. Each rare particle can be contacted with a unique detection reagent and each detection reagent can be detected by one of two detection devices. Furthermore, wherein the detection reagents comprise fluorescent moieties, two interrogation devices (e.g., two lasers) producing radiation at different wavelengths corresponding to excitation wavelengths of the different fluorescent moieties can be used. The respective fluorescent radiation can be detected by two different detection devices. In some aspects, the detection reagents can be differentiable by fluorescence at different wavelengths.

In some aspects, the two or more rare particles can be detected in series. For example, the method can comprise detecting a first rare particle at a first location of an eDAR apparatus and detecting a second rare cell at a second location of an eDAR apparatus. In this case, the aliquot in which the first and second particle reside can be channeled to a new location after the first detection step, after the second detection step, or after both detection steps.

In certain aspects, the detection event can occur at a regular frequency. The frequency may relate to the size of the detection volume and the flow rate of the fluid sample. The detection volume of a particular apparatus can be within the range of, and including the limits of, 0.1-100 μL (e.g., 10 μL) and the fluid sample can flow through the apparatus at a rate within the range of, and including the limits of, 1-1000 μL/second (e.g., 100 μL/second), a different aliquot can be detected within the range of, and including the limits of, once every 0.001-1 second (e.g., 0.1 seconds), or at a rate within the range of, and including the limits of, 1-100 Hz (e.g., 10 Hz).

In some aspects, the geometry of the apparatus and the volume of the fluid to be processed can affect the rate. For example, aliquots can traverse through the detection volume at a rate within the range of, and including the limits of, 0.1 kHz and 100 MHz. In some aspects, the aliquots traverse through the detection volume at a rate within the range of, and including the limits of, 10 Hz and 10 MHz or about 10 MHz. In some aspects, the aliquots may traverse through the detection volume at a frequency within the range of, and including the limits of, 0.1 kHz and 100 MHz or about 100 MHz, or within the range of, and including the limits of 1 kHz or about 1 kHz and 10 MHz or about 10 MHz, or frequency within the range of, and including the limits of about 1 kHz and 5 MHz or about 5 MHz, or frequency within the range of, and including the limits of 1 kHz or about 1 kHz and 1 MHz or about 1 MHz. In some aspects, the frequency by which the aliquots traverse through the detection volume can be at least about 0.1 kHz, or at least about 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 60, 70, 80, 90, 100, 125, 150, 200, 250, 300, 400, 500, 600, 700, 800, or 900 kHz, or at least about 1 MHz, or at least about 2, 3, 4, 5, 6, 7, 8, 9, 10, 15, 20, 25, 30, 35, 40, 45, 50, 60, 70, 80, 90, or 100 MHz. In some aspects, the frequency by which the aliquots traverse through the detection volume can be at least 0.1 kHz, or at least 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 60, 70, 80, 90, 100, 125, 150, 200, 250, 300, 400, 500, 600, 700, 800, or 900 kHz, or at least 1 MHz, or at least 2, 3, 4, 5, 6, 7, 8, 9, 10, 15, 20, 25, 30, 35, 40, 45, 50, 60, 70, 80, 90, or 100 MHz.

In some aspects, detection of a characteristic from an ensemble of analytes (e.g., cells) in an aliquot of a fluid sample can be simultaneous or cumulative over time. For example, detection of a characteristic can be simultaneous from a large aliquot containing an ensemble of analytes. During simultaneous mode, the particles can be carried by a flow of variable velocity. In other cases, particles can be carried by a steady flow as they traverse through the detection volume.

In various aspects, the eDAR apparatuses and methods allow a signal to be detected simultaneously from a plurality of analytes (e.g., a plurality of cells). In some aspects, an aliquot is ranked based on a signal detected simultaneously from a plurality of analytes present within the aliquot.

In other cases, the methods herein provide for detection of a characteristic from an ensemble of cells can emanate over time ("cumulative") from a small detection volume which is on the order of a single cell, but with multiple cells traversing through the detection volume with the aid of flow. Cumulative mode of eDAR is distinct from time-lapse overlay of consecutive signals or frames emanating from a single bioparticle; timelapse overlay of a single bioparticle does not constitute an ensemble of bioparticles. In both simultaneous and cumulative, a decision is rendered only after a characteristic from an ensemble of cells has been detected.

In some aspects, the detector is selected from the group consisting of a camera, an electron multiplier, a charge-coupled device (CCD) image sensor, a photomultiplier tube (PMT), an avalanche photodiode (APD), a single-photon avalanche diode (SPAD), a silicon photomultiplier (SiPM), and a complementary metal oxide semiconductor (CMOS) image sensor. In some aspects, the eDAR apparatus provided herein can comprise a photo, electro, acoustical or magnetic detector to track the motion of select cells or to enumerate select particles or cells present in an aliquot.

In some aspects, an apparatus or method provided herein can incorporate fluorescence (single or multi-color) microscopy imaging in various configurations, which include but are not limited to bright-field, epi, confocal, trans, DIC (differential interference contrast), dark-field, Hoffman, or phase-contrast.

In some aspects, the apparatuses provided herein can comprise a plurality of detection devices, for example, at least 2, 3, 4, 5, 6, 7, 8, 9, 10, or more detection devices. Multiple detection devices may be useful for performing the methods of the present disclosure, for example, wherein more than one rare particle or cell is present in a fluid sample, more than one cell marker is being used to differentiate different cell types, or multiple detection reagents are being detected simultaneously. In some aspects, the detection devices can include a confirmatory laser. For example, the confirmatory laser can be used to interrogate the sorted aliquot. In some aspects, the sorted aliquot detected by the confirmatory laser can be a positive aliquot and retained after sorting. In some aspects, the sorted aliquot detected by the confirmatory laser can be a negative aliquot and can be discarded after sorting. For example, the confirmatory laser can be used as a second detection method to control the accuracy of the eDAR sorting scheme.

Sources of Radiation and Devices

The disclosure provides an apparatus for eDAR that can include a detection device or an imaging device and a ranking device (e.g., a computer). In some aspects, a laser (or more than one laser) can serve as an interrogation device. An inverted microscope with photodiodes, photomultipliers, or cameras can be used as a detection device. A mask can be placed in a path between the channel and the detection devices.

In some aspects, the interrogation device (e.g., a 488 nm solid-state diode pumped laser and a 633 nm HeNe laser) can be directed into an inverted microscope. The two laser beams can be shaped using cylindrical optics or diffractive optics to form a collimated elliptical beam with an aspect ratio of 10 to 1 prior to entering the microscope objective. Using a combination of half-waveplate and polarizing beam splitter, the intensity of each beam can be adjusted, while mirrors independently steer the light to create a spatially co-localized excitation region. The fluorescence from bioparticles can be split into three wavelength bands by two dichroic mirrors before passing through the bandpass filters and refocused onto the three single-photon avalanche diodes (SPADs). One SPAD can collect fluorescence in the wavelength range of 560-610 nm, a second SPAD cab collect fluorescence in the range of 645-700 nm, and a third SPAD can collect in the range of 500-540 nm. The SPAD outputs are directed to a digital processor (e.g., computer) with a counter/timer board and analyzed with several algorithms.

In some aspects, a digital processor accepts a signal from the detection device and through an algorithm to rank the aliquot. The digital processor can direct the aliquot into the appropriate channel based on the value of the ranking (e.g., the presence, absence, quantity, identity, or composition of rare particles in the fluid sample). eDAR can consist of one, two, three, four, five or six detection devices and one, two, three, four, five or six interrogation devices, or multitudes of detection devices and interrogation devices.

Dual Capture eDAR

This disclosure further provides an apparatus for a "dual-capture" version of eDAR. The dual-capture apparatus can separate two different subpopulations of rare cells from the same sample of mixed fluid. This can be performed on a single microfluidic chip simultaneously. The two subpopulations can further be trapped separately on two different regions on the microfluidic chip.

Figure 11:
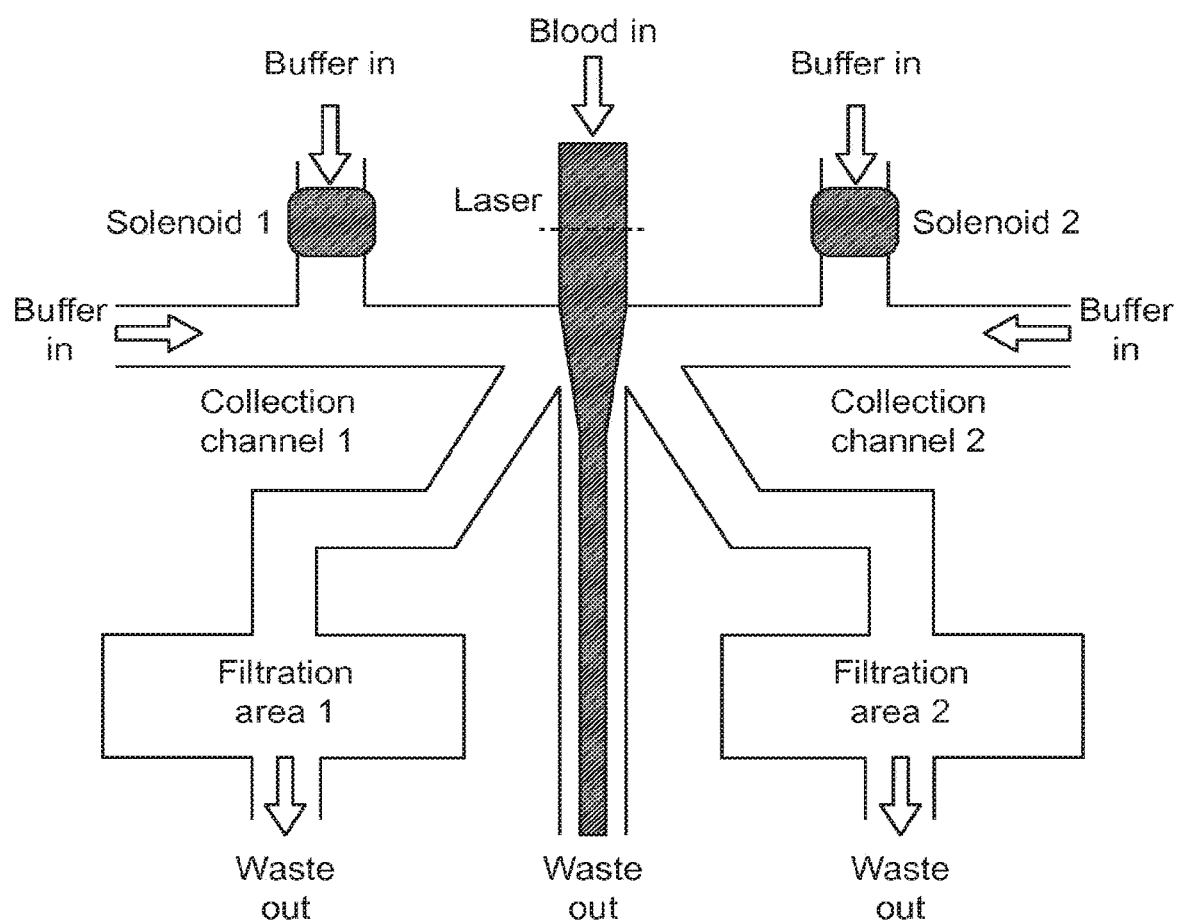
FIG. 11 depicts the general structure of the "dual-capture" eDAR according to an aspect of the present disclosure.

A general structure of the dual capture version of the microfluidic eDAR device is depicted in FIG. 11. Samples can be labeled with at least two unique antibodies that are conjugated to unique fluorescent tags. For example, the sample (e.g, blood) can be labeled with a first tag conjugated with a unique fluorophore that binds to a marker (e.g., epithelial, anti-EpCAM-PE) on an analyte within the sample and a second tag conjugated with a unique fluorophore that binds to a marker (e.g., mesenchymal, anti-EGFR or anti-vimentin) on an analyte within the sample where each fluorophore can have a different wavelength of emission (e.g., FITC). The labeled blood sample can be injected into the microfluidic chip. The rare cells which express EpCAM can be detected using the line-confocal scheme (described before) and the peak can be detected in the yellow channel. A sorting event can be triggered to collect that particular aliquot into a collection channel (e.g., collection channel #1). In some aspects, the aliquot can be ranked as positive to a mesenchymal markers then the rare cell can be sorted in to a different collection channel (e.g., collection channel #2). The two subpopulations of rare cells can be separately trapped and enriched on the dual-capture eDAR microfluidic chip.

The dual-capture eDAR apparatus can use a fluidic switching scheme (FIG. 11). The labeled sample can be introduced into the main channel on the top. Buffer can flow in the two side channels to control the hydrodynamic switching of the blood flow using two solenoids. In some aspects, the filtration area of the dual-capture eDAR can be built using microslits (described before). Two subpopulations of CTCs can be separated and trapped on two different filtration areas on the same microfluidic chip.

Figure 12:
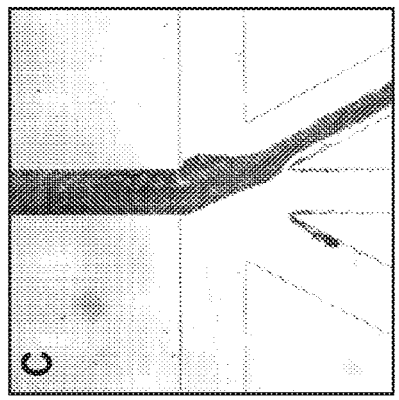
FIG. 12 shows bright field images of the three status of the blood flow.
Figure 12:
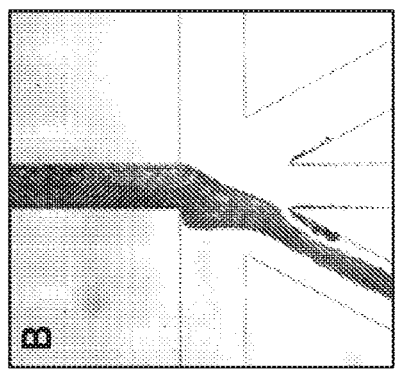
Figure 12:
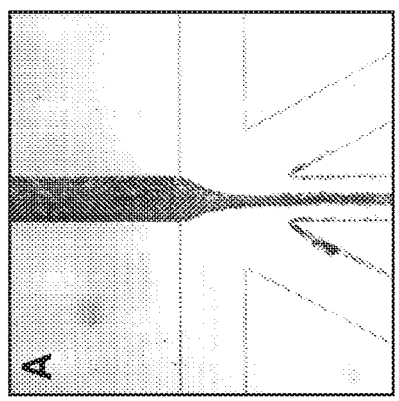

The dual-capture eDAR apparatus can include solenoids. In some aspects, both of the solenoids can be closed when aliquots are ranked as negative (FIG. 12). The sample can flow to the bottom center channel to collect as waste if the pressure is balanced in both channels. In other cases, when the aliquots are ranked positive with respect to only one of the two markers (e.g., epithelial) then solenoid #2 can be opened for the sample to flow into the collection channel on the left (FIG. 12B). After the aliquot is collected, solenoid #2 can be closed again and the flow of the sample is returned to the center channel. In some aspects, the aliquots can be ranked as positive to only one marker (e.g., epithelial) and solenoid #1 can be opened to allow flow of the sample to the right channel (FIG. 12C). In some aspects, the response time for the two types of sorting events in the dual-capture eDAR apparatus is quick (e.g., less than or equal to 3 milliseconds).

Immunostaining and Bleaching in a Microfluidic Chip

This disclosure provides a scheme for a sequential immunostaining and bleaching method using a microfluidic device. The method can use the eDAR apparatus cited in PCT WO 2010/120818, the apparatus provided herein, or other apparatuses known in the art. In some aspects, this scheme can be coupled with eDAR. In some aspects, the scheme can be coupled with an in-line staining and washing system to minimize the dead volume; decrease the amount of antibodies used; avoid introducing air bubbles; and automate the process of isolating, staining and bleaching rare cells.

eDAR can be used to capture analytes (e.g., rare cells). The rare cells can be enriched to a small area (e.g., chamber) on the microfluidic chip. The small area can be used to rapidly image the labeled cell and minimize the amount of reagents (e.g., antibodies, buffers, etc) used. The microfluidic chip can be designed with an open, accessible structure. The open structure can allow for further manipulation of single cells (e.g., picking up a cell of interest or delivering certain reagents to a cell).

In some aspects, a virtual aliquot can be acquired by a combination of the laser detection beam, the volumetric flow rate, and the sorting speed. Based on these factors, the labeled sample can be virtually divided up into aliquots (e.g, 500,000 per 1 mL of sample at 2 nL per aliquot). In some aspects, the line-confocal detection method can detect fluorescence emission from each cell. The virtual aliquots can be ranked according to the labeling scheme. If labeled, the aliquot is "positive" and if unlabeled, the aliquot is "negative." In some aspects, negative aliquots can be discarded (FIG. 4A).

In some aspects, following the aliquot ranking, an automatic feedback mechanism can trigger a hydrodynamic switch of the flow. The switch can collect and transfer the "positive" aliquots to an area of the microfluidic chip for further purification (e.g., purification chamber) and analysis. In some aspects, the sorted aliquots can be transferred to an area of the microfluidic chip where rare cells (e.g., circulating tumor cells) can be trapped and the blood cells can be discarded (FIG. 4A). In some aspects, the trapped cells can be imaged and labeled with one or several tags (e.g., labeled antibodies) that recognize biomarkers.

The labeling and imaging of analytes (e.g., rare cells) can occur on the microfluidic chip (e.g., eDAR apparatus). In some aspects, two ports on the microfluidic chip can be placed in the open position to perform the perfusion labeling and washing steps (FIG. 13A). The remaining three ports can remain closed. A peristaltic pump can deliver washing buffer (e.g., Isoton (Beckman Coulter Inc., Chino, CA)) and labeling reagents to the microfluidic chip. A pressurized buffer source can be coupled to the pump and microfluidic chip using a six-way valve. In some aspects, the other three ports on the valve can be closed to prevent leak and/or contamination.

Figure 13:
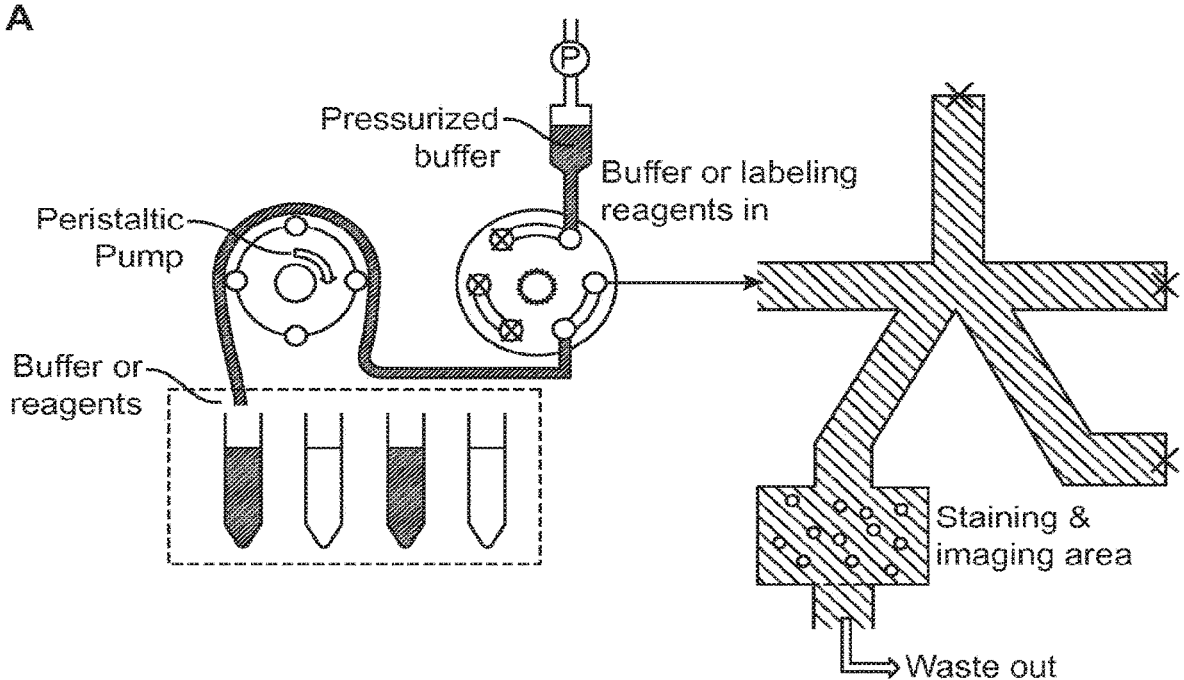
FIG. 13 provides a general scheme and procedure of the sequential immunostaining and photobleaching tests according to an aspect of the present disclosure.
Figure 13:
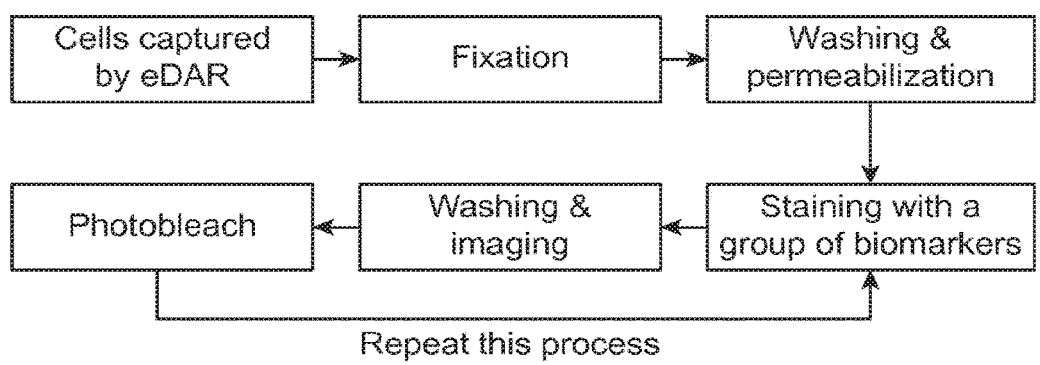

This method provides for staining of markers on isolated analytes (e.g., rare cells) (FIG. 13B). The method can be performed using antibodies (e.g., less than or equal to 10 nanograms) and an incubation step (e.g., less than or equal to 30 minutes). To perform the method of immunostaining and photobleaching, the six-way valve can be turned open towards the pressurized buffer for stable control of the hydrodynamic switching. The valve can be turned towards the peristaltic-pump to inject specific amounts of a reagent in to the microfluidic chip. A peristaltic pump can be used to deliver the labeling reagents and washing buffer (FIG. 13). The cross bars indicate the corresponding ports can be closed. In some aspects, the valve can prevent air bubbles from entering the microfluidic chip system.

In some aspects, the method can be used to perform intracellular marker staining. In this method, the captured cells can be fixed and permeabilized using a permeabilization agent, such as a detergent (e.g., Triton, surfynol 465 surfactant, etc.) on the microfluidic chip prior to immunostaining. The method further describes multiple rounds of immunostaining the individual cells, washing of the stained cells, imaging of the markers in the cells and photobleaching of the markers that are bound to the individual cells. The steps can be repeated sequentially for multiple rounds.

In some aspects, isolated cells can be fixed. Fixation can be performed using perfusion (e.g., manual or automatic) or diffusion (e.g, manual or automatic) methods. In some aspects, fixation can be performed on the microfluidic chip or off the microfluidic chip after the sample has been removed from the microfluidic chip. In some aspects, samples or isolated particles may not be fixed. In this case, samples may include living particles (e.g., mammalian cells, bacterial cells, fungal cells, yeast cells, etc.). Samples may include a structure that may be damaged by fixation.

In some aspects, isolated particles can be permeabilized. Permeabilization can be performed using perfusion (e.g., manual or automatic) or diffusion (e.g, manual or automatic). In some aspects, permeabilization can be performed on the microfluidic chip or off the microfluidic chip after the sample has been removed from the microfluidic chip. In some aspects, samples or isolated particles may not be permeabilized. In this case, samples may include markers (e.g., extracellular, cell-associated, etc.,). Samples may include a structure that may be damaged by permabilization.

Analytes that have been contacted with a tag can be photobleached. The process of photobleaching can reduce the signal emitted from the tag that is in contact with the analyte. In some aspects, a device that can be used for In some aspects, analytes can be contacted with a tag and the tag can be bleached chemically. In some aspects, the tag can generate a signal that is readable by a detector. For example, the signal can be emitted by fluorophores. In some aspects, the signal can be chemically quenched or bleached using chemicals including, but not limited to, oxidizing reagents, halogen ions, reducing agents, or any other appropriate fluorescence quencher. In some aspects, the reducing agent is dithiothreitol. In other cases, the tag that can recognize the biomarkers, such as the antibodies, can be chemically dissociated from the binding sites with a high efficiency, using appropriate reagents. In some aspects, the destaining reagent can be a Tris-based buffer with 2% SDS, 20 mM di-thiothreitol (DTT) and 60 mM Tris pH 6.8.

Figure 14:
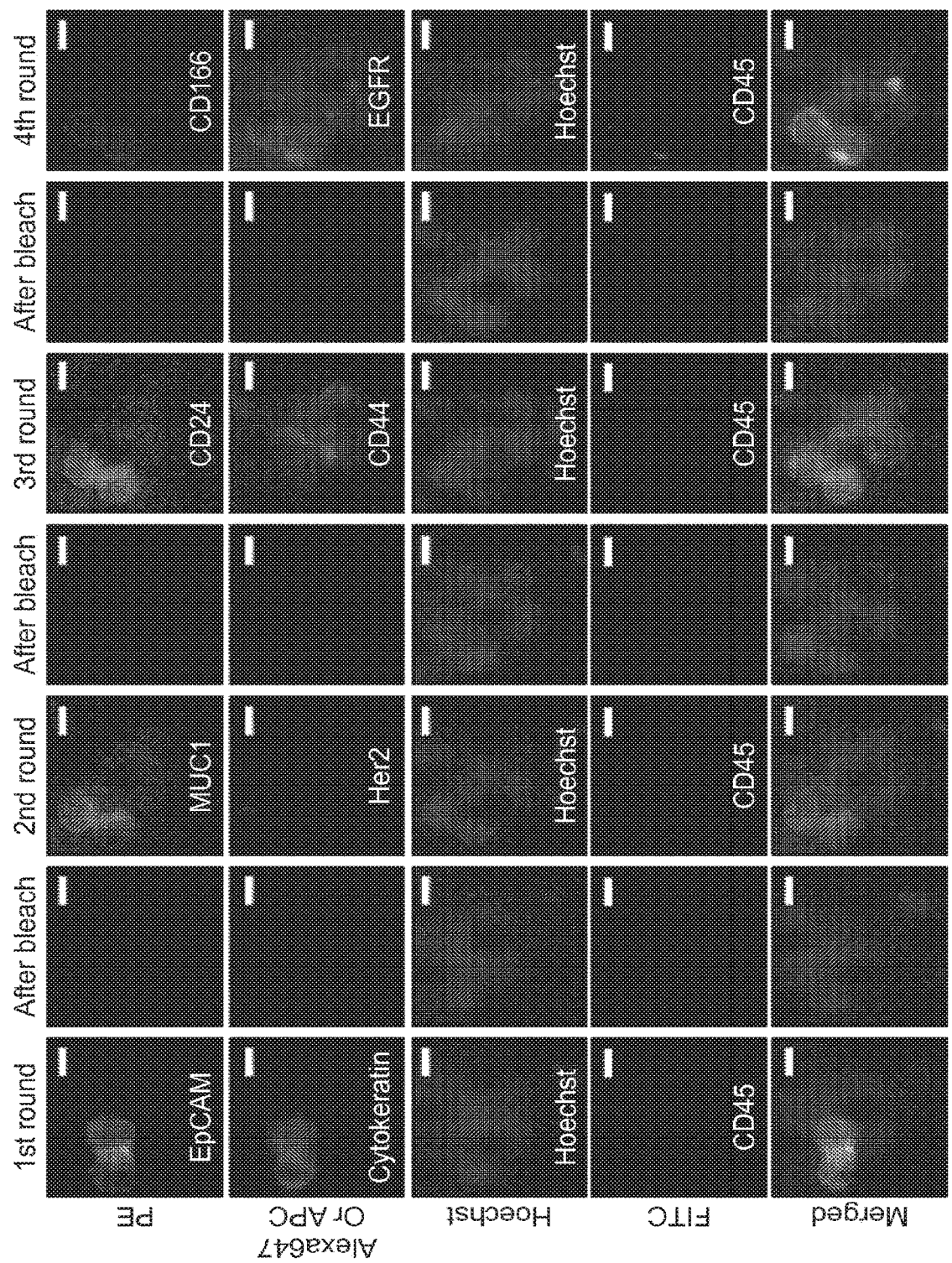
FIG. 14 shows sequential immunostaining and photobleaching results for six cancer cells trapped on an eDAR microfluidic chip according to an aspect of the present disclosure.
Figure 15:
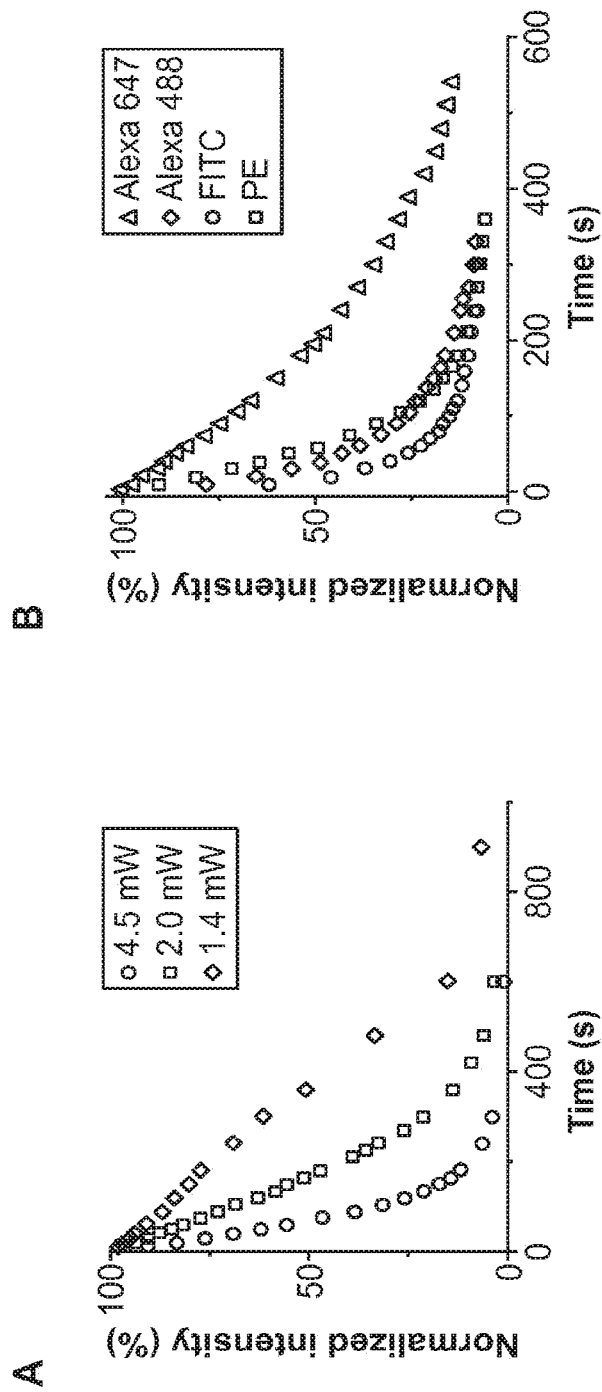
FIG. 15 depicts an example of photobleaching curves for the MCF-7 cells labeled with anti-EpCAM-PE that are exposed to different powers of the light source according to an aspect of the present disclosure.

The method can include photobleaching after each imaging step. The parameters used can deliver a highly efficient and rapid throughput photobleaching process (FIG. 14 and Table 2). Photobleaching curves for cells (e.g., MCF-7) labeled with a tag directed to a biomarker (e.g., anti-EpCAM-PE) can be generated after exposure of labeled cells to different powers of the photobleaching light source (FIG. 15A). Additional curves can be generated using multiple conjugates (e.g., Alexa 647, Alexa488, FITC, PE) to the same antibody (FIG. 15B).

The steps of labeling and photobleaching can be repeated multiple times to study several groups of biomarkers. For example, two biomarkers of interest can be combined with a positive control marker (e.g., nuclear stain) and a negative control marker (e.g., CD45) to create a group. One group can be studied in each round, followed by photobleaching before a second round of immunostaining occurs. In some aspects, the method of sequential immunostaining and photobleaching can be used to determine the expression of different protein markers on an analyte. For example, an analyte (e.g., rare cell, cancer cell, etc.) trapped on the microfluidic chip is EpCAM, cytokeratin and Hoescht positive but CD45 negative (Table 2, below).

TABLE 2

Shows experimental details of four rounds of immunostaining and photobleaching.

| Yellow channel | Anti-EpCAM-PE Lot# 515776 (1:50 dilution, Biolegend, San Diego, CA) | MUC1-PE Lot# B160021 (1:50 dilution, Biolegend, San Diego, CA) | Anti-CD24 PE Lot# B159732 (1:50 dilution, Biolegend, San Diego, CA) | Anti-CD166 PE Lot# B139297 (1:10 dilution, Biolegend, San Diego, CA) |
|---|---|---|---|---|
| Red Channel | (PAN) Cytokeratin-AlexaFluro647 Lot# 4528S-14 (1:10 dilution, CellSignalling, Danvers, MA) | HER2-AlexaFluro647 Lot# B110523 (1:50 dilution, Biolegend, San Diego, CA) | Anti-CD44-AlexaFluro647 Lot# B124953 (1:66 dilution, Biolegend, San Diego, CA) | EGFR-APC Lot# B161059 (1:40 dilution, Biolegend, San Diego, CA) |
| Blue Channel | Hoechst Lot# 1249542 (1:500 dilution, Life technologies, Carlsbad, CA) | Hoechst Lot# 1249542 (1:500 dilution, Life technologies, Carlsbad, CA) | Hoechst Lot# 1249542 (1:500 dilution, Life technologies, Carlsbad, CA) | Hoechst Lot# 1249542 (1:500 dilution, Life technologies, Carlsbad, CA) |
| Green Channel | Anti-CD45-FITC Lot# B116314 (1:66 dilution, Biolegend, San Diego, CA) | Anti-CD45-FITC Lot# B116314 (1:66 dilution, Biolegend, San Diego, CA) | Anti-CD45-FITC Lot# B116314 (1:66 dilution, Biolegend, San Diego, CA) | Anti-CD45-FITC Lot# B116314 (1:66 dilution, Biolegend, San Diego, CA) | photobleaching can include, a laser, a light emitting diode, a voltaic arc lamp, an incandescent lamp, a fluorescent lamp, an ultraviolet lamp or a halogen lamp. In some aspects, the voltaic arc lamp can be selected from, but is not limited to, the following types of arc lamps, neon, argon, xenon, krypton, sodium, metal halide, mercury or carbon.

In some aspects, only one first tag that is directed to a biomarker can be used in the first round of immunostaining. In this case, the first tag can be photobleached. A different second tag that is directed to a different biomarker can be used in a next round of immunostaining. The different second tag can be photobleached.

In some aspects, only one first tag that is directed to a biomarker can be used in the first round of immunostaining. In this case, the first tag can be photobleached. The same second tag that is directed to a different biomarker can be used in a next round of immunostaining. The second same tag can be photobleached.

In some aspects, only one first tag that is directed to a biomarker can be used in the first round of immunostaining. In this case, the first tag can be photobleached. A different second tag that is directed to a different biomarker can be used in a next round of immunostaining. The second different tag can be photobleached.

In some aspects, only one first tag that is directed to a biomarker can be used in the first round of immunostaining. In this case, the first tag can be photobleached. A different second tag that is directed to a same biomarker can be used in a next round of immunostaining. The second different tag can be photobleached.

In some aspects, a plurality of tags comprise a first set where each are directed to a unique biomarker can be used in the first round of immunostaining. In this case, the first set of a plurality of tags are photobleached. A different second set of a plurality of tags that are directed to a different set of unique biomarkers can be used in a next round of immunostaining. The second set of different tags can be photobleached. In some aspects, some of the tags used in the first set can also be used in the second set. In some aspects, some of the biomarkers targeted by the tags in the first set can also be targeted by the tags in the second set. In some aspects, the second set of biomarkers can be identical to the first set of biomarkers. In some aspects, the second set of tags can be identical to the first set of tags. In some aspects, the second set of tags can contain overlapping tags with the first set of tags. In some aspects, the second set of biomarkers can contain overlapping biomarkers to the first set of biomarkers.

In another case, six (e.g., multiple) individual cells (e.g., cancer cells) can be trapped on a microfluidic chip (FIG. 14). The eight biomarkers can include two control biomarkers (e.g., one positive control and one negative control) and four biomarkers (e.g., EpCAM/Cytokeratin, MUC1/Her2, CD44/CD24 and CD166/EGFR) can be observed per round. In some aspects, the positive control biomarker (e.g., Hoechst nuclear stain) may not be photobleached. The negative control biomarker (e.g., CD45) can be photobleached and a new tag can be included with each round of immunostaining. The four biomarkers per round can include both controls and two additional markers. Each round can include immunostaining, imaging and photobleaching (Table 2).

An in-line immunostaining and photobleaching system can be coupled with the method of immunostaining and photobleaching for the labeling and fluorescence imaging of analytes (e.g., rare cells). The in-line system can increase the speed and efficiency of the immunostaining and photobleaching method when multiple rounds are used. The system can include, labeling rare cells (e.g., CTCs) with a group of antibodies conjugated to different fluorophores followed by photobleaching. After photobleaching, the rare cells can be re-labeled with different fluorescent antibodies against additional biomarkers.

In some aspects, rare cells isolated using the eDAR microfluidic chip apparatus can be washed using buffers. The buffers can be any buffer suitable for the application. Isolated cells can remain on the microfluidic chip and the main, side and waste channels can be closed by turning off the in-line valves.

The method provides for detection of a signal emitted by a tag, or signals emitted by several tags, using a device. In some aspects, the device can be microscope. The microscope (e.g., confocal, inverted etc.) can be equipped with light sources and detectors for fluorescence. In other cases, the device can be one of several devices known to those of skill in the art for detection of signals emitted by tags.

In some aspects, detection can occur in conjunction with photobleaching, after photobleaching is complete, or before photobleaching begins. Detection can be used to determine the end point of emission of detectable signal from the tag. In some aspects, detection can occur in conjunction with immunostaining. Detection can also occur after the wash step, before the wash step, during the wash step or in the absence of a wash step. In some aspects, detection can also occur after the permeabilization step, before the permeabilization step, during the permeabilization step or in the absence of a permeabilization step. In some aspects, detection can also occur after the fixation step, before the fixation step, during the fixation step or in the absence of a fixation step.

The method includes imaging of signals emitted by the tags. Devices used for imaging have been described above, are included in PCT WO20120/120818 or are known to those of skill in the art. For example, fluorescent images can be collected before and after the photobleaching step. Images can include data from all emission channels. In some aspects, the emission channels can include, yellow (555 to 605 nm), blue (435 to 485 nm), green (510 to 540 nm) and red (665 to 695 nm). In some aspects, isolated analytes can be imaged using bright-field or Nomarski microscopy.

Figure 16:
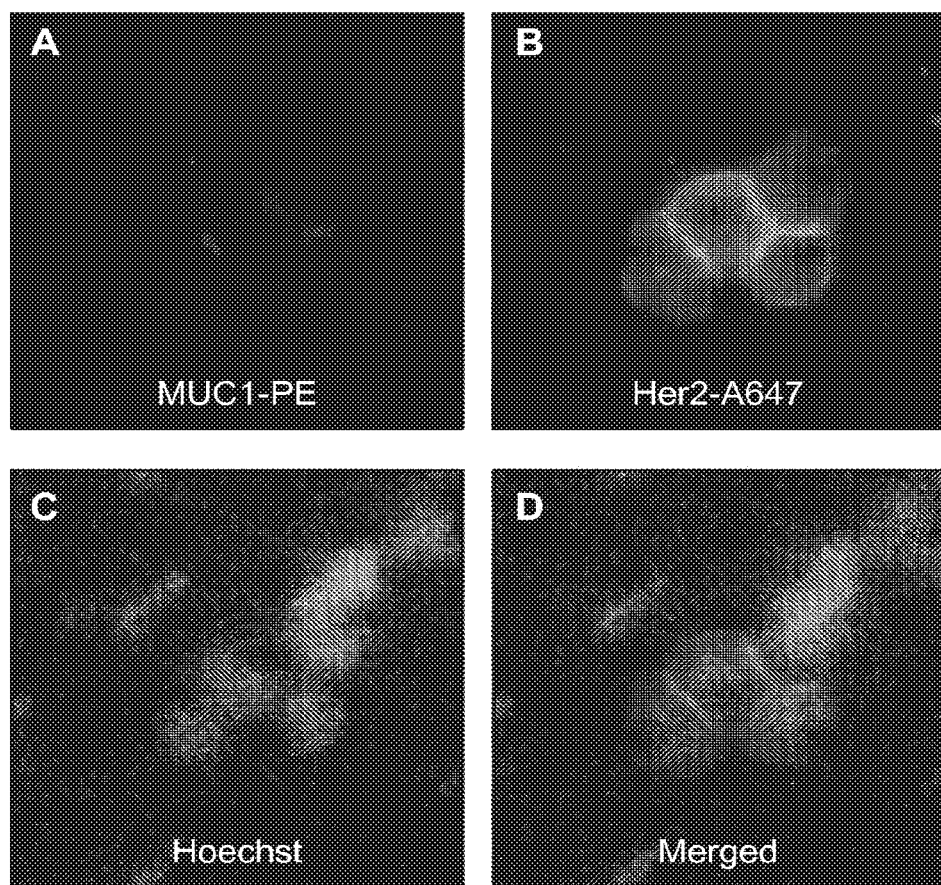
FIG. 16 shows fluorescence images of the four cancer cells captured on eDAR with Her2$^+$/MUC1$^-$ character according to an aspect of the present disclosure.

In some aspects, images can be analyzed for expression of multiple biomarkers. Individual cells (e.g., four) captured by eDAR and contacted with tags to detect biomarkers (e.g., Her2 and MUC1) and a positive control biomarker (e.g., Hoechst) can be imaged using fluorescence (FIG. 16). A digital processor (e.g., computer) and software can be used to merge multiple images into a single multi-color image (FIG. 16D).

The method further provides for the collection of analytes (e.g., particles). The particles (e.g., rare cells) collected may have been subject to immunostaining and photobleaching. In some aspects, the trapped rare cells can be subject to additional rounds of immunostaining and photobleaching off the microfluidic chip. In some aspects, the rare cells can be collected for further processing. Collection can involve placement of the rare cells into a reservoir (e.g., tube, plate, array, etc.). Rare cells can be fixed after collection. In some aspects, the rare cells can be living cells and maintained in cell culture.

In some aspects, the methods provided herein can further be coupled to an assay protocol following isolation of the analytes. Non-limiting examples of assays that can be coupled to the methods provided herein include nucleic-acid based methods such as RNA extraction (with or without amplification), cDNA synthesis (reverse transcription), gene microarrays, DNA extraction, Polymerase Chain Reactions (PCR) (single, nested, quantitative real-time, or linker-adapter), or DNA-methylation analysis; cytometric methods such as fluorescence in situ hybridization (FISH), laser capture microdissection, flow cytometry, fluorescence activated cell sorting (FACS), cell culturing, or comparative genomic hybridization (CGH) studies; chemical assay methods such as electrophoresis, Southern blot analysis or enzyme-linked immunosorbent assay (ELISA); assays to determine the microRNA and siRNA contents; assays to determine the DNA/RNA content; assays to determine lipid contents; assays to determine carbohydrate contents; assays to determine metabolite contents; assays to determine protein contents; and functional cell assays (e.g., apoptotic assays, cell migration assays, cell proliferation assays, cell differentiation assays, etc.), and the like.

Types of Labels

The method of immunostaining and photobleaching can include the use of tags, or labels, to identify biomarkers located on trapped analytes (e.g., particles). In some aspects, tags can be detected using the eDAR apparatus described herein, or other apparatuses configured for detection of tags known to those of skill in the art. In some aspects, tags can be photobleached using the components of the apparatus described herein or using a photobleaching device known to those of skill in the art. In some aspects, the tags can be photobleached using an apparatus that may cause damage to the particle. In other cases, tags cannot be photobleached.

In some aspects, tags can be used as labels for immunostaining. Tags can be detectable by spectroscopic, photochemical, biochemical, immunochemical, chemical, or other physical means. For example, useful tags can include, without limitation radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin (PE), etc.), auto-quenched fluorescent compounds that are activated by tumor-associated proteases, enzymes (e.g., luciferase, horse-radish peroxidase, alkaline phosphatase, etc.), nanoparticles, biotin, digoxigenin, and the like. In some aspects, the tags can emit in a spectrum detectable as a color in an image. The colors can include red, blue, yellow, green, purple, orange and the like.

In some aspects, the tags can be perfused to selectively label or accentuate the isolated cells. Examples of such reagents include, without limitation, fluorescent, immuno-fluorescent, dye-conjugated molecules (such as antibodies, fab fragments, aptamers, polymers, ligands, agonists, antagonists, or combinations thereof) magnetic, electroactive, bioactive, or photoactive compounds. An example is to use a stain that reacts with cytokeratins, which are integral components of the cytoskeleton in epithelial cancerous cells. Other dye examples include fluorescein isothiocyanate (FITC)-conjugated mouse anti-human epithelial antibody (HEA) and phycoerythrin (PE)-conjugated anti-CD45. Other examples of dye-conjugated antibodies include but are not limited to the pan-cytokeratin antibody A45B/B3, AE1/AE3, or CAM5.2 (pan-cytokeratin antibodies that recognize Cytokeratin 8 (CK8), Cytokeratin 18 (CK18), or Cytokeratin 19 (CK19) and ones against: breast cancer antigen NY-BR-1 (also known as B726P, ANKRD30A, Ankyrin repeat domain 30A); B305D isoform A or C (B305D-A ro B305D-C; also known as antigen B305D); Hermes antigen (also known as Antigen CD44, PGP1); E-cadherin (also known as Uvo-morulin, Cadherin-1, CDH1); Carcino-embryonic antigen (CEA; also known as CEACAMS or Carcino-embryonic antigen-related cell adhesion molecule 5); β-Human chorionic gonadotophin (β-HCG; also known as CGB, Chronic gonadotrophin, β polypeptide); Cathepsin-D (also known as CTSD); Neuropeptide Y receptor Y3 (also known as NPY3R; Lipopolysaccharide-associated protein3, LAP3, Fusion; Chemokine (CXC motif, receptor 4); CXCR4); Oncogene ERBB1 (also known as c-erbB-1, Epidermal growth factor receptor, EGFR); Her-2 Neu (also known as c-erbB-2 or ERBB2); GABA receptor A, pi (π) polypeptide (also known as GABARAP, GABA-A receptor, pi (n) polypeptide (GABA A(a), γ-Aminobutyric acid type A receptor pi (π) subunit), or GABRP); ppGalNac-T(6) (also known as β-1-4-N-acetyl-galactosaminyl-transferase 6, GalNActransferase 6, GalNAcT6, UDP-N-acetyl-d-galactosaminepolypeptide N-acetylgalactosaminyltransferase 6, or GALNT6); CK7 (also known as Cytokeratin 7, Sarcolectin, SCL, Keratin 7, or KRT7); CK8 (also known as Cytokeratin 8, Keratin 8, or KRT8); CK18 (also known as Cytokeratin 18, Keratin 18, or KRT18); CK19 (also known as Cytokeratin 19, Keratin 19, or KRT19); CK20 (also known as Cytokeratin 20, Keratin 20, or KRT20); Mage (also known as Melanoma antigen family A subtytpes or MAGE-A subtypes); Mage3 (also known as Melanoma antigen family A 3, or MAGA3); Hepatocyte growth factor receptor (also known as HGFR, Renal cell carninoma papillary 2, RCCP2, Protooncogene met, or MET); Mucin-1 (also known as MUC1, Carcinoma Antigen 15.3, (CA15.3), Carcinoma Antigen 27.29 (CA 27.29); CD227 antigen, Episialin, Epithelial Membrane Antigen (EMA), Polymorphic Epithelial Mucin (PEM), Peanut-reactive urinary mucin (PUM), Tumor-associated glycoprotein 12 (TAG12)); Gross Cystic Disease Fluid Protein (also known as GCDFP-15, Prolactin-induced protein, PIP); Urokinase receptor (also known as uPR, CD87 antigen, Plasminogen activator receptor urokinase-type, PLAUR); PTHrP (parathyroid hormone-related proteins; also known as PTHLH); BS106 (also known as B511S, small breast epithelial mucin, or SBEM); Prostatein-like Lipophilin B (LPB, LPHB; also known as Antigen BU101, Secretoglobin family 1-D member 2, SCGB1-D2); Mammaglobin 2 (MGB2; also known as Mammaglobin B, MGBB, Lacryglobin (LGB) Lipophilin C (LPC, LPHC), Secretoglobin family 2A member 1, or SCGB2A1); Mammaglobin (MGB; also known as Mammaglobin 1, MGB1, Mammaglobin A, MGBA, Secretoglobin family 2A member 2, or SCGB2A2); Mammary serine protease inhibitor (Maspin, also known as Serine (or cystein) proteinase inhibitor clade B (ovalbumin) member 5, or SERPINBS); Prostate epithelium-specific Ets transcription factor (PDEF; also known as Sterile alpha motif pointed domain-containing ets transcription factor, or SPDEF); Tumor-associated calcium signal transducer 1 (also known as Colorectal carcinoma antigen CO17-1A, Epithelial Glycoprotein 2 (EGP2), Epithelial glycoprotein 40 kDa (EGP40), Epithelial Cell Adhesion Molecule (Ep-CAM), Epithelial-specific antigen (ESA), Gastrointestinal tumor-associated antigen 733-2 (GA733-2), KS1/4 antigen, Membrane component of chromosome 4 surface marker 1 (M4S1), MK-1 antigen, MIC18 antigen, TROP-1 antigen, or TACSTD1); Telomerase reverse transcriptase (also known as Telomerase catalytic subunit, or TERT); Trefoil Factor 1 (also known as Breast Cancer Estrogen-Inducible Sequence, BCEI, Gastrointestinal Trefoil Protein, GTF, pS2 protein, or TFF1); folate; or Trefoil Factor 3 (also known as Intestinal Trefoil Factor, ITF, p1.B; or TH-3), or the like.

Markers/Biomarkers

The method provides for a plurality of biomarkers that can be expressed by, located on or near an analyte (e.g., trapped particle). The plurality of biomarkers that can be detected by the instant disclosure is subject to the number of rounds of immunostaining and photobleaching that can be performed on the trapped particle. Each round of immunostaining can include no tags, 1 tag, 2 tags, 3 tags, 4 tags, 5 tags, 6 tags, 7 tags, 8 tags, 9 tags or 10 tags. The range of tags for each round of immunostaining can include 1-10 tags (e.g., 4).

In some aspects, the presence of a marker, such as a biomarker, is indicated by a signal emitted by a tag, wherein the tag has an affinity for the marker. As used herein, the phrase "has an affinity for" broadly encompasses both direct molecular binding affinity for a marker by a tag, as well as indirect affinity, such as an ability of the tag and the marker to interact via a molecular complex involving one or more other structures. For example, in some aspects, the tag may be a primary antibody with a direct affinity for the marker, whereas in other aspects, the tag may be a secondary antibody with an indirect affinity for the marker.

In some aspects, cells are isolated according a specific marker or biomarker profile, such that a given cell exhibits a unique and/or identifiable marker or biomarker profile. In certain aspects, the marker or biomarker profile is a specific combination of one or more, two or more, three or more, four or more, five or more, six or more, seven or more, eight or more, nine or more, or ten or more markers or biomarkers, which can be used to define and identify a cell or cell type. In some aspects, the marker or biomarker profile can be used to identify a cell as being part of a particular population of cells have a particular set of properties.

In some aspects, biomarkers are extracellular. In other cases, biomarkers can be intracellular, cytoplasmic, intracytoplasmic, cell surface, extranuclear, intranuclear, lysosomal, mitochondrial, endoplasmic reticular and the like. In other cases, biomarkers can be attached to but not in trans to the particle.

In some aspects, biomarkers can be an amino acid, a peptide, a polypeptide, a protein, a denatured protein. In these cases, structures can be native or denatured.

In some aspects, biomarkers can be a nucleic acid, an oligonucleic acid, a ribonucleic acid, a transfer ribonucleic acid, a messenger ribonucleic acid, a micro ribonucleic acid or a deoxyribonucleic acid. In these cases, acids can be single or double stranded.

In other cases, the rare particle can be a cell, protein, protein complex, nucleic acid, nucleoprotein complex, carbohydrate, metabolite, catabolite, and the like. In some aspects, the rare particle is a cell. In some aspects, the cell can be a cancer cell, a circulating tumor cell (CTC), a cancer stem cell, a cancer cell displaying a cancer surface antigen, for example, one selected from the groups consisting of CD44, CD2, CD3, CD10, CD14, CD16, CD24. CD31, CD45, CD64, CD140b, or a combination thereof.

In some aspects the cell is a fetal cell. In some aspects, the fetal cell can be in maternal fluid. The maternal fluid can include whole blood, fractionated blood, serum, plasma, sweat, tears, ear flow, sputum, lymph, bone marrow suspension, lymph, urine, saliva, semen, vaginal flow, feces, transcervical lavage, cerebrospinal fluid, brain fluid, ascites, breast milk, vitreous humor, aqueous humor, sebum, endolympth, peritoneal fluid, pleural fluid, cerumen, epicardial fluid, and secretions of the respiratory, intestinal and genitourinary tracts.

In some aspects, the analyte is a dissociated cell that is not connected to other cells or extracellular matrix, or embedded within a tissue.

In some aspects, cancer stem cells can be distinguished from ordinary cancer cells by perfusing other reagents that selectively bind to biomarkers, which can include but are not limited to CD44, CD2, CD3, CD10, CD14, CD16, CD24. CD31, CD45, CD64, CD140b or CD166.

For example, tags can be designed to detect expression of EGFR and CD166 to demonstrate the mesenchymal characteristics of tumor cells. Other related markers, such as vimentin and cadherin, can be used in this group.

In other cases, biomarkers that indicate the viability of the particle can be used. In these cases, biomarkers which indicate apoptosis, necrosis, mitosis, stage of mitosis, meiosis and the like can be used.

In some aspects, each set of markers can include a nuclear stain (Hoechst) as a positive control biomarker, CD45 conjugated with FITC as a negative control biomarker, and two protein biomarkers conjugated with PE or Alexa 647. In some aspects, the Hoechst stain may not be photobleached. In this case, Hoechst is a positive control. In this case, Hoechst may not be photobleached with a standard light source. In this case, a UV exposure may be used to bleach the stain.

Photobleaching

The method provides for photobleaching after immunostaining. Photobleaching can involve use of light to remove or reduce the intensity of the signal emitted by detectable portion of a tag from an analyte. The tag can be removed by quenching the signal that the tag or label emits. In some aspects, the photobleaching can occur after one round of immunostaining or after sequential rounds of immunostaining.

In some aspects, photobleaching can be performed using a LED or a xenon arc lamp as the light source (Sutter instrument, Novato, CA). Using the xenon arc lamp, each photobleaching step can occur for 1-59 seconds, 1-30 minutes or for 15 minutes.

In some aspects, the maximum power of the LED xenon arc lamp can be locked for safety within a range of 1-20 mW or at 10 mW or at 100 mW or 1 W, depending on the power density (e.g., $W/m^2$) of the light source. Use of protective methods, such as wearing protective goggles or covering the photobleaching area with a black box, can be considered.

Figure 17:
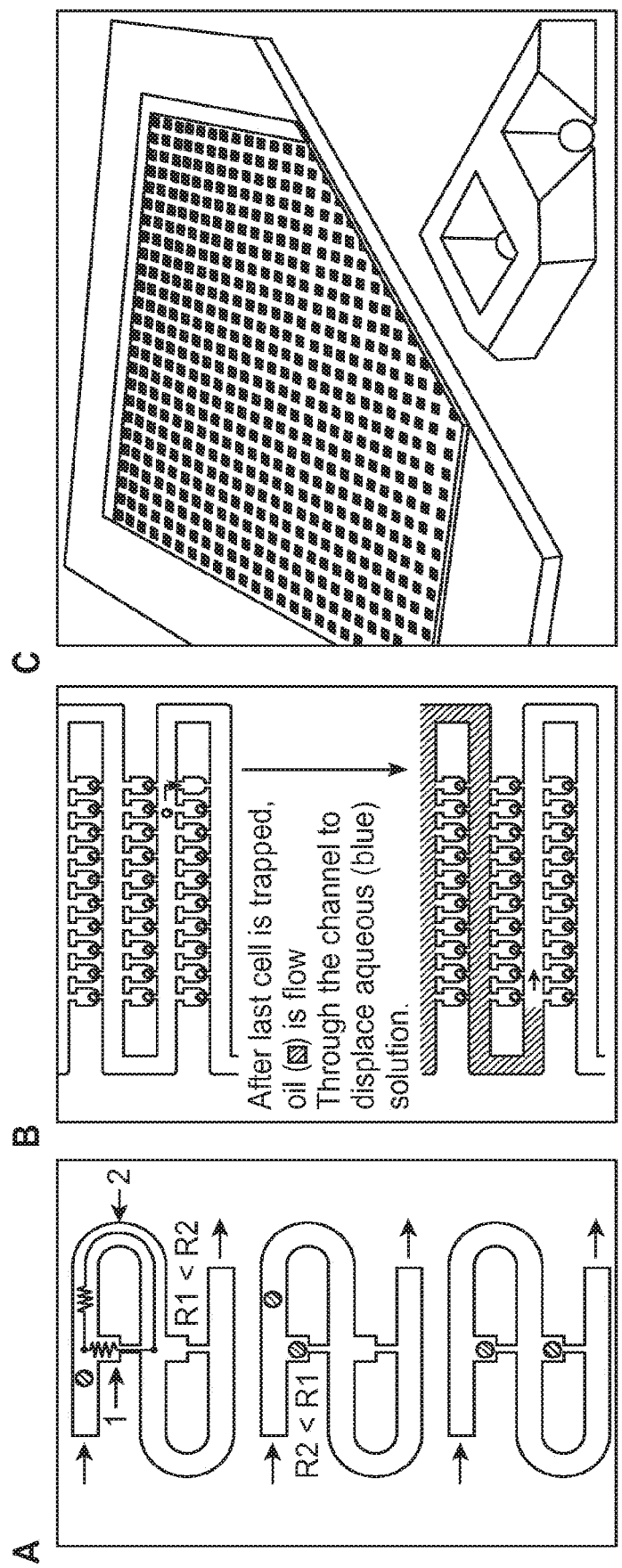
FIG. 17 is a diagram of Single-analyte array according to an aspect of the present disclosure.

In some aspects, the fluorescent emission of a fluorphore (e.g., PE, FITC and Alexa 488) can be bleached. Bleaching the signal (e.g., to less than 10%) can occur in a short amount of time (e.g., in less than 5 min). Use of lasers with longer wavelengths (e.g., 610 to 660 nm) may have a longer duration of time of photobleaching than those of shorter wavelengths (FIG. 17B). In some aspects, when use of multiple lasers at various wavelengths is involved, the bleaching time may be higher than the minimum requirement for one of the lasers (e.g., 15 min) to achieve a high bleaching efficiency with an acceptable throughput.

For example, a curve for photobleaching using different exposure powers using MCF-7 cells labeled with anti-EpCAM-PE, and placed on a No. 2 coverslip is shown in FIG. 15A. Different power settings (e.g., three) can be used to bleach the cells. In some aspects, at a high power (e.g., greater than 2 mW), the exposure time may be reduced (e.g., less than 10 min) to achieve a high (e.g., 95%) bleaching efficiency.

Samples

In the disclosure provided herein, samples can include fluid samples. Fluid samples can originate from a variety of sources. In some aspects, the sources may be humans, mammals, animals, microbes, bacteria, fungus, yeast, viruses, rodents, insects, amphibians and fish.

Fluid samples provided in this disclosure can be liquids that may or may not contain a rare particle of interest. In some aspects, the sample may be an environmental fluid sample, for example from a lake, river, ocean, pond, stream, spring, marsh, reservoir, or the like. In yet other cases, the sample may be a water sample, for example from a desalinization plant, water treatment plant, reservoir, spring, stream, glacial water flow, water tower, or other water source that may be contemplated as a source of potable water.

In some aspects, this disclosure provides analytes, including analytes that are rare particles. A rare particle can be a cell or macromolecule present in a fluid sample at a low level. In certain aspects, a rare particle can be a cell, protein, protein complex, nucleic acid, nucleoprotein complex, carbohydrate, metabolite, catabolite, and the like. In certain aspects, a particle can be considered rare if it is present in a fluid sample at a concentration of less than about 10% of the total particle population in the fluid, or at less than about 9%, 8%, 7%, 6%, 5%, 4%, 3%, 2%, 1%, 0.5%, 0.1%, 0.05%, 0.01%, or less of the total particle population in the fluid. In yet other cases, the rare particle can be present in a fluid sample at less than about 1 part per $10^3$ of the total particle population in the fluid, or at less than about 1 part per $10^4$, $10^5$, $10^6$, $10^7$, $10^8$, $10^9$, $10^{10}$, $10^{11}$, $10^{12}$, or less of the total particle population in the fluid. In certain aspects, a particle can be considered rare if it is present in a fluid sample at a concentration of less than 10% of the total particle population in the fluid, or at less than 9%, 8%, 7%, 6%, 5%, 4%, 3%, 2%, 1%, 0.5%, 0.1%, 0.05%, 0.01%, or less of the total particle population in the fluid. In yet other cases, the rare particle can be present in a fluid sample at less than 1 part per $10^3$ of the total particle population in the fluid, or at less than 1 part per $10^4$, $10^5$, $10^6$, $10^7$, $10^8$, $10^9$, $10^{10}$, $10^{11}$, $10^{12}$, or less of the total particle population in the fluid.

In some aspects, a fluid sample can contain a certain percentage of water and/or other elements. For example, a fluid sample can be blood which contains, amongst other materials, plasma. Generally, plasma is mostly water and can contain proteins, ions, vitamins, enzymes, hormones, and other chemicals in the body.

In some aspects, the fluid samples can be body fluids. Body fluids are often complex suspensions of biological particles in a liquid. For example, a body fluid can be blood. In some aspects, blood can include plasma and/or cells (e.g., red blood cells, white blood cells, circulating rare cells) and platelets. In some aspects, 55% of blood fluid volume can be cells. In some aspects, a blood sample can be concentrated so that at least 30%, at least 40%, at least 50%, at least 60%, at least 70%, at least 80%, or at least 90% of the blood is cells. In some aspects, a blood sample contains blood that has been depleted of one or more cell types. In some aspects, a blood sample contains blood that has been enriched for one or more cell types. In some aspects, a blood sample can be diluted so that at least 30%, at least 40%, at least 50%, at least 60%, at least 70%, at least 80%, or at least 90% of the blood is cells. In some aspects, a blood sample contains a heterogeneous, homogenous or near-homogenous mix of cells.

Body fluids can include, but are not limited to, whole blood, fractionated blood, serum, plasma, sweat, tears, ear flow, sputum, lymph, bone marrow suspension, lymph, urine, saliva, semen, vaginal flow, feces, transcervical lavage, cerebrospinal fluid, brain fluid, ascites, breast milk, vitreous humor, aqueous humor, sebum, endolymph, peritoneal fluid, pleural fluid, cerumen, epicardial fluid, and secretions of the respiratory, intestinal and genitourinary tracts. In some aspects, body fluids can be in contact with various organs (e.g., lung) that contain mixtures of cells and bioparticles.

In some aspects, body fluids can contain rare particles. In some aspects, the rare particle is a rare cell. Rare cells can be nucleated or non-nucleated. Rare cells include, but are not limited to, cells expressing a malignant phenotype; fetal cells, such as fetal cells in maternal peripheral blood, tumor cells, such as tumor cells which have been shed from tumor into blood or other bodily fluids; cells infected with a virus, such as cells infected by HIV, cells transfected with a gene of interest; and aberrant subtypes of T-cells or B-cells present in the peripheral blood of subjects afflicted with autoreactive disorders.

In some aspects, the body fluid can be blood and contain rare cells. The rare cells can be erythrocytes, white blood cells, leukocytes, lymphocytes, B cells, T cells, mast cells, monocytes, macrophages, neutrophils, eosinophils, dendritic cells, stem cells, erythroid cells, cancer cells, tumor cells or cell isolated from any tissue originating from the endoderm, mesoderm, ectoderm or neural crest tissues. Rare cells can be from a primary source or from a secondary source (e.g, a cell line).

The type and amount of cells and bioparticles that are present in a particular body fluid (e.g., blood) can reveal information about the health of the organism. For example, a subject suffering from cancer can have cancerous cells in body fluid. A sample from a subject suffering from an infection can contain an increased number of immune cells (e.g., lymphocytes, neutrophils, B cells, T cells, dendritic cells, etc.) indicative of infection or can contain pathogenic material such as microbial cells or nucleic acids. A sample from a pregnant female can contain fetal cells indicative of the genotype or karyotype of the fetus.

Some cells or bioparticles can be present in a body fluid in rare quantities compared to normal quantities. Such rare cells can include, circulating tumor cells, cancer stem cells, etc. These cells can appear in a body fluid as a result of an event (e.g., cancer) occurring in a region of the body. The cell can originate from the organ containing the body fluid or an organ near the body fluid. For example, the rare breast cancer cell can be present in blood or lymph fluid located near a mammary gland. In some aspects, the cell originates from a more distant organ. For example, a cell that originates from a testicular tumor can be present in a blood sample taken from the arm.

Analysis

The disclosure further provides for methods whereby an analysis can be performed. In some aspects, the analysis can include a source for interrogating an aliquot. In other cases, wherein an aliquot contains an analyte (e.g., rare particle) that can intrinsically exhibit chemiluminescence or bioluminescence, the apparatus may not require a source for interrogating the aliquot.

In some aspects, a ranking device can be selected from a computer, a processor, a controller, a chip with integrated circuits, a circuit board, an electronic element, software, an algorithm, or a combination thereof. In some aspects, the processor can be a digital processor (e.g., FGPA, ASIC, or RT). In some aspects, a computer accepts the signal from the detection device and through an algorithm ranks the aliquot. The ranking device can direct the aliquot into the appropriate channel based on the value of the ranking (e.g., the presence, absence, quantity, identity, or composition of rare particles in the fluid sample).

In some aspects, the information coming from the first detector can be analyzed. The information from the first detector can be analyzed and the result can show that the analyte is positive. In some aspects, the information from the detector can be analyzed and the result can show that the analyte is negative. In some aspects, the ranking device sends the signal, which reads to the positive or the negative analyte, to the hydrodynamic switching element (e.g., solenoid valve) to sort the analytes. In some aspects the positive analyte can be moved to a unique channel of the microfluidic chip. In some aspects, the positive analyte can be moved to a unique chamber of the microfluidic chip. In some aspects, the positive analyte can be moved to the waste chamber of the microfluidic chip. In some aspects the negative analyte can be moved to a unique channel of the microfluidic chip. In some aspects, the negative analyte can be moved to a unique chamber of the microfluidic chip. In some aspects, the negative analyte can be moved to the waste chamber of the microfluidic chip. In some aspects, the positive analyte is partitioned from the negative analyte.

In some aspects, analysis can be performed using the information relayed from a second detector. The second detector can be used to confirm the information obtained using the first detector. In some aspects, the second detector can be located on the microfluidic chip. In some aspects, the second detector may not be located on the microfluidic chip. In some aspects, the second detector obtains a signal from the cells that can be sorted based on the signal detected by the first detector. In some aspects, the second detector receives detects signal from the sorted cells and can send information about the signal to a computer. The computer can be used to determine whether the appropriate cell was sorted.

In some aspects, an analysis of the information acquired during the method of immunostaining can be performed. The method of immunostaining of an analyte occurs in a chamber of the microfluidic chip. At the chamber, a detector can detect one or a plurality of signals from first round of staining. In some aspects, one or the plurality of signals can be photobleached. The detector can monitor the duration and intensity of the signal emitted. In some aspects, the analyte can undergo a second round of staining. The detector can detect signal emitted by the analyte following the second round of staining. In some aspects, one or the plurality of signals can be photobleached. The detector can monitor the duration and intensity of the signal emitted. In some aspects, the cycles of immunostaining and photobleaching can be repeated a plurality of cycles. A computer can be used to, for example, compare the one or more signals of immunostained analytes with first round of immunostaining to ensure that photobleaching occurred.

Single-Analyte Array Devices and Methods

This disclosure provides methods and apparatuses for capturing single analytes from a liquid phase. In some aspects, the analytes can be particles. In other cases, the analytes can be cells. The analytes can be trapped in chambers. In other cases, the analytes can be trapped in wells. In other cases, the analytes can be trapped on patches. In some aspects, the chambers or the wells can be arranged in a linear format. In other cases, the chambers or wells can be arranged in an array format.

The device can be designed in various formats. For example, a two-dimensional (2D) device can be created. In some aspects, the 2D device can have axially linear flow (FIG. 17B). The axial linear flow can be a serial-flow design. In some aspects, a three-dimensional (3D) device can be created. For example, the 3D device can have chambers arranged in a grid (FIG. 17C). There are several alternative designs that can be used for either 2D or 3D strategies if needed.

Figure 18:
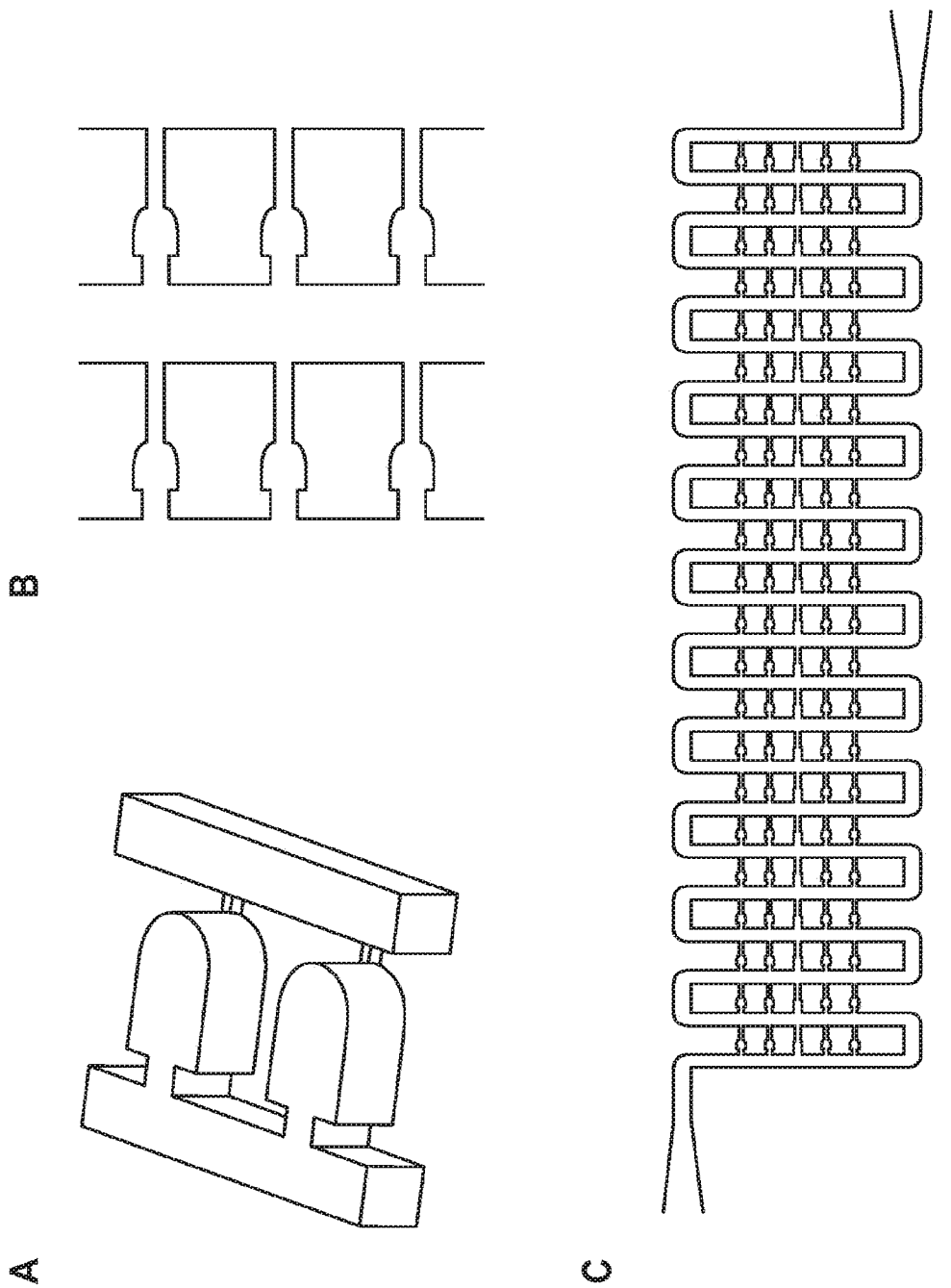
FIG. 18 is a schematic of a device with trapping densities and dimensions according to an aspect of the present disclosure.

The 2D device can have channels and chambers with a variety of potential dimensions. The dimensions can affect the serial-flow resistance trap design. A schematic of a device with potential trapping densities and dimensions is shown in FIG. 18 and the magnified region of the device in the inset. In some aspects, the potential dimensions can include, the width of the main channel, the width of the constriction, the length from the main channel constriction entrance to the main channel constriction exit, the length across the constriction, as well as the heights of the main channel, the constriction, and the constriction chamber.

In some aspects, the serial-flow resistance trap can be paired with a microfluidic device. The device can consists of an inlet, where sample can be introduced (left side), as well as an outlet, where excess liquid phases can be removed (right side). The center of the device can have a high density of flow resistance traps which can be incorporated. FIG. 18B shows a magnified region of FIG. 18C. In some aspects, the flow resistance traps can constitute a functional part of the device.

Figure 19:
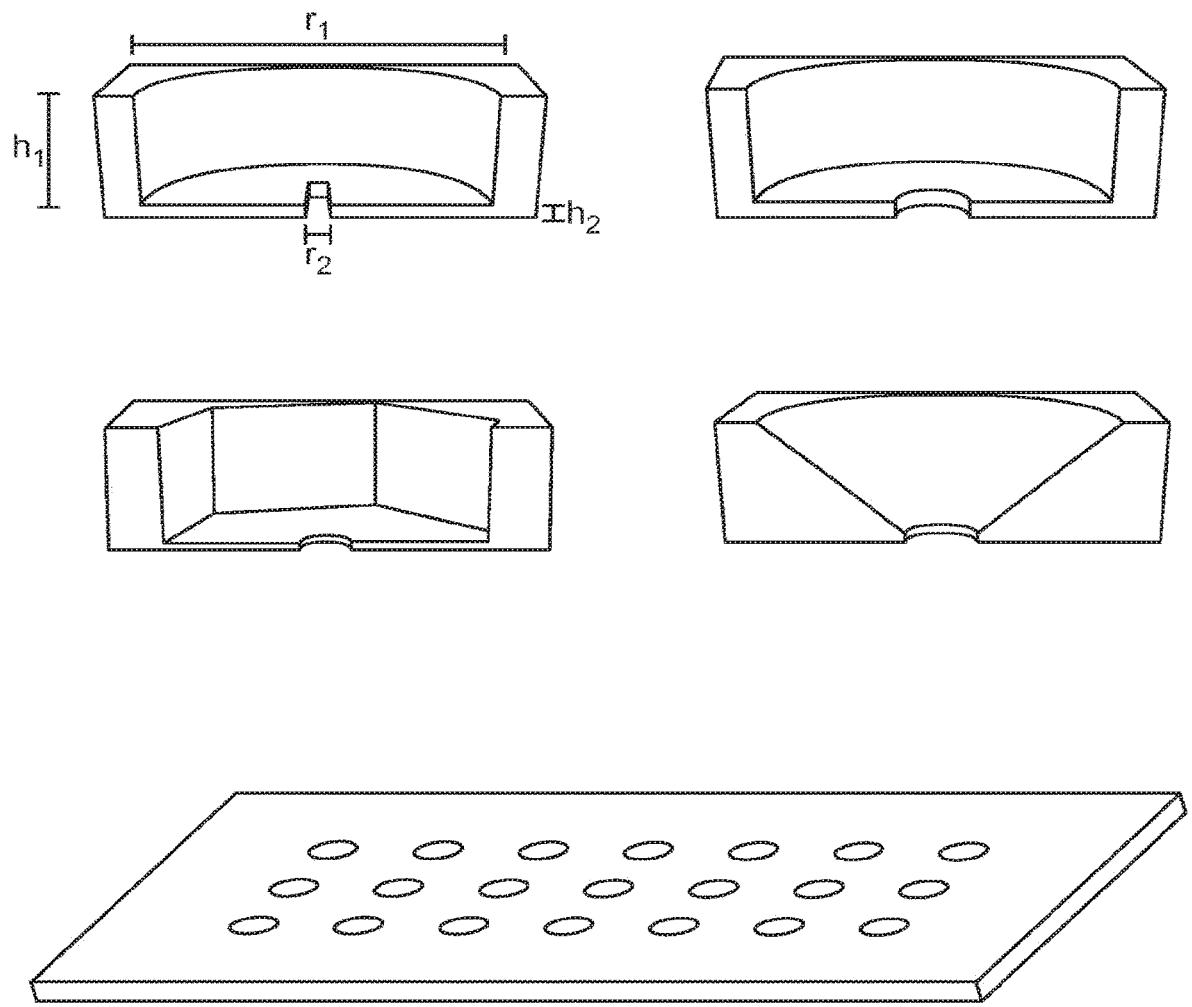
FIG. 19 depicts the parallel flow resistance trap according to an aspect of the present disclosure.

The 3D device can have chambers with a variety of potential dimensions and shapes. The dimensions and shapes can affect the parallel flow resistance trap design. In some aspects, the chambers of the 3D device can be wells. The device can trap single particles/cells from a solution (e.g., such as beads, cells, etc.) and multiple wells can be arranged in parallel to form the device. A cross-sectional side view of a well on the 3D device can illustrate potential shape variations (FIG. 19). In some aspects, the well design can include a helix, ellipse, parabola, hyperbola, polygon, apeirogon, chiliagon, decagon, enneagon, googolgon, hectagon, heptagon, hendecagon, hexagon, megagon, myraigon, octagon, pentagon, quadrilateral, triangle, trapezium, cylinder, hyperplane, plane, platonic solid, dodecahedron, hexahedron, icosahedrons, octahedron, tetrahedron, torus, quadric, done, cylinder, sphere, hyperboloid, paraboloid, polychoron, hecatonicosachoron, hexacosichoron, hexadecachoron, icositetrachoron, pentachoron, tesseract, spherical cone, or dome. In some aspects, the dimensions of the well can be defined by $h_1$=depth of well, $h_2$=depth of constriction, $r_1$=radius of well, and $r_2$=radius of constriction.

In some aspects, the physical material of the device can consist of an optically transparent material, including, but not limited to glass, polymer (e.g., PDMS, mylar, Dymax, polyurethane). In other cases, the physical material of the device can be constructed from multiple layers. In some aspects, the multiple layers can comprise various layers of the aforementioned materials.

Figure 20:
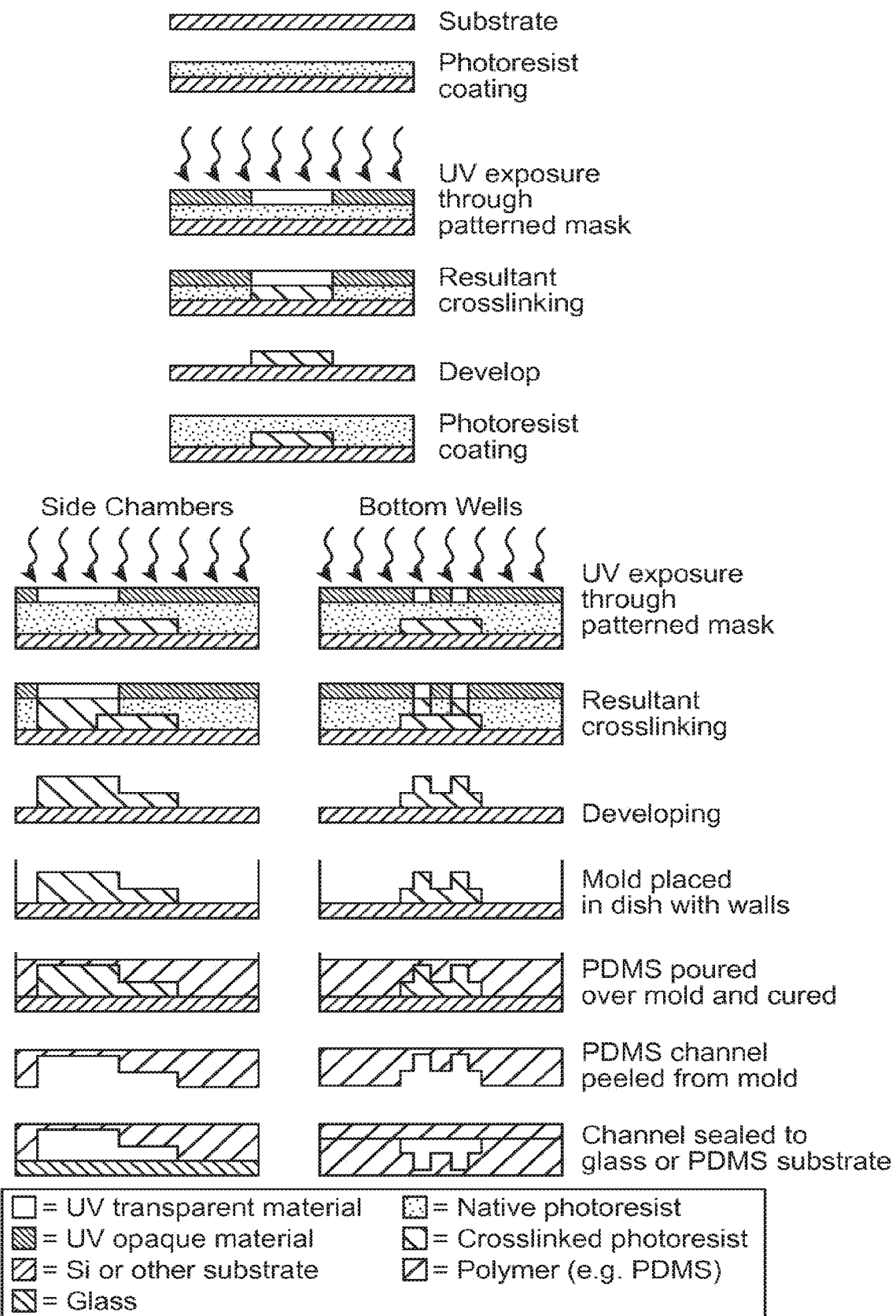
FIG. 20 is a schematic of the procedure used to build some of the devices described in the present disclosure.

The device described in the disclosure can be built using methods described herein. For example, FIG. 20 is a schematic depiction of a method that can be used to build some of the devices. In some aspects, the method can include building the device layer by layer. For the first layer, a solid substrate (e.g., silicon wafer) can be spin-coated with photoresist. The coated substrate can be placed in hard contact with a photolithographic mask imprinted with the desired design depicted in UV-transparent and opaque regions. The mask and substrate can be exposed to UV-light. The UV-light can be used to crosslink photochemicals in the photoresist. The first layer of the fabricated device can be completed by developing the resultant crosslinked pattern, dissolving away the non-crosslinked portion of the photoresist. In some aspects, the second layer can be built using a mold. The mold can be prepared by coating, exposing, and developing another layer of photoresist. In some aspects, the mold can be used for forming channel, chamber, and well structures in a curable (e.g., PDMS) or embossable material. For example, the mold can be placed into a dish. In some aspects, the PDMS can be poured over the mold and cured. The PDMS can be released from the mold, and inlets and outlets can be punched. In some aspects, the patterned PDMS can be sealed to a flat glass or piece of PDMS to enclose the channels and chambers or wells.

Figure 21:
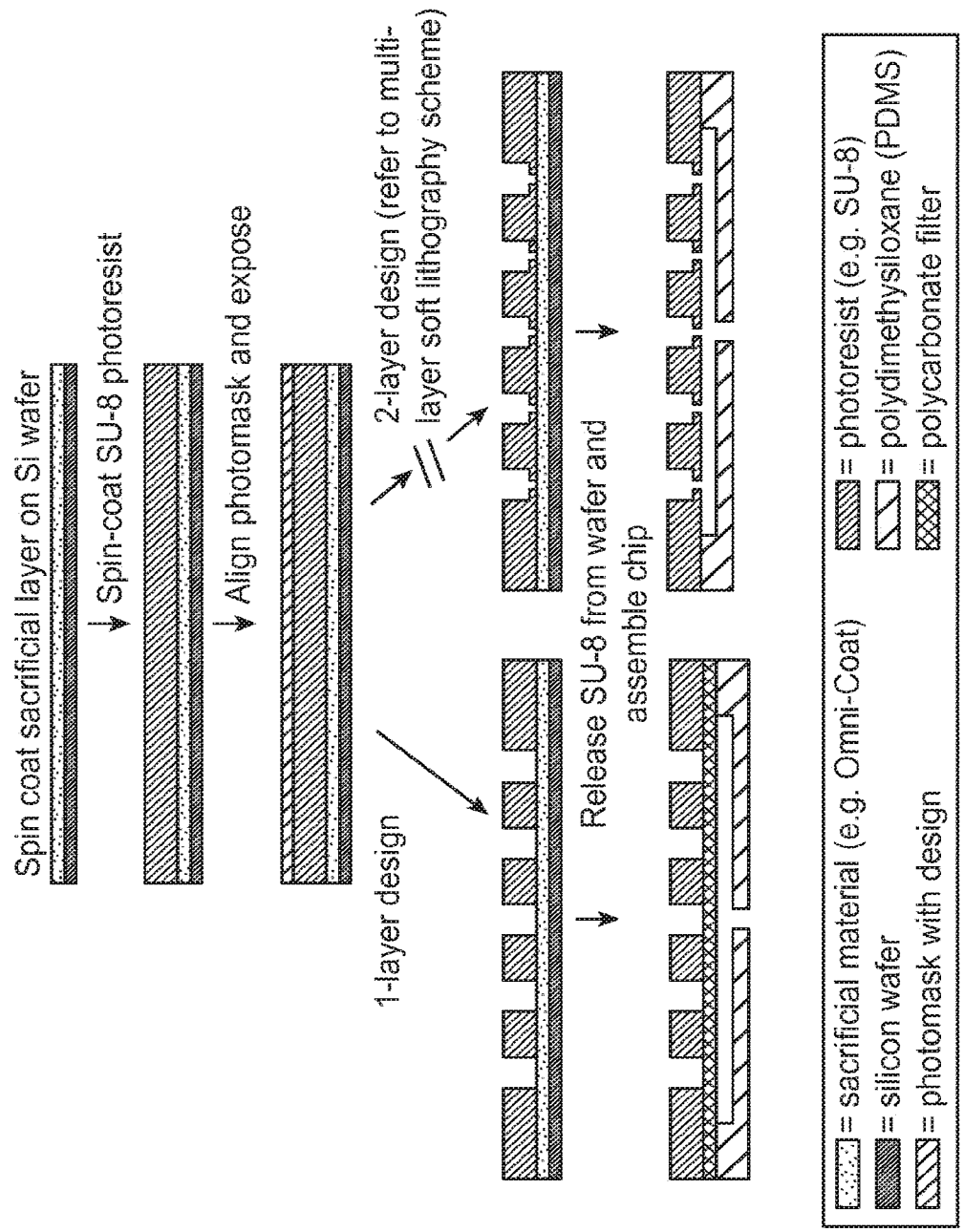
FIG. 21 is an example of a microfabrication method which can be used to produce the parallel flow resistance trap according to an aspect of the present disclosure.

The device described in the disclosure can be built using methods described herein. For example, a microfabrication method can be used to produce the parallel flow resistance trap (FIG. 21). The device can be fabricated in material other than photoresist (e.g., SU-8), which can include, but is not limited to, polymeric material, photoresist, polymethydisoloxane (PDMS), polymethylmethacrylate (PMMA), polymethylurethane (PUMA), etc. In some aspects, the microfabrication method can include, (1) spin coating a sacrificial layer on a silicon (Si) wafer, (2) depositing photoresist (SU-8) on top, (3) aligning a photomask with the microarray pattern and exposing the wafer to UV, (4) processing and removing the uncrosslinked photoresist, if needed, spin coating and processing a second layer of photoresist, and finally (5) releasing the SU-8 layer from the Si wafer and assembling onto (path 1 only) a porous polycarbonate filter and/or (path 1-2) a PDMS mount with a single outlet for inserting tubing.

In some aspects, single cells can be trapped by fluid forces. The fluid forces can hold the cells. In some aspects, the fluid forces can be enhanced by interaction with molecules on the surface of the device. In some aspects, molecules can exhibit specific binding (e.g., aptamers, antibodies, primary amines, succinymidyl esters) or non-specific binding (e.g., polyelectrolytes). In other cases, the fluid forces can be enhanced by optical forces. The optical forces can include but are not limited to, attractive forces (e.g., single beam gradient optical trap, vortex trap), repulsive forces (e.g., scattering), interfacial forces (e.g., Marangoni forces), electrostatic forces (repulsive forces, attractive forces) or by magnetic forces (e.g., exerted by the interaction of applied magnetic fields with inherent magnetically susceptible internal species).

The disclosure provides a device, method, and system that can perform sequestration or trapping, manipulation, and detection of a sample. In some aspects, the samples can consist of analytes being trapped (e.g., held in a fixed position by forces generated from fluid flow, gravity, optical forces, or molecular interactions or formation of covalent bonds) in a microfluidic device.

In some aspects, an analyte is trapped at, immobilized at, held at, or otherwise attached to a micro-cavity, such as a well or compartment in a microfluidic device. In further aspects, the analyte is within the micro-cavity. In some aspects, an analyte is trapped at, immobilized at, held at, or otherwise attached to a micro-patch, such as a patch coated with a substrate in a microfluidic device. In further aspects, the analyte is trapped at, immobilized at, held at, or otherwise attached to a micro-cavity or micro-patch through forces generated from fluid flow and/or gravity. In some aspects an analyte is trapped at, immobilized at, held at, or otherwise attached to a micro-cavity or micro-patch through an adhesive force, a molecular interaction and/or a covalent bond. In some aspects an analyte is trapped at, immobilized at, held at, or otherwise attached to a micro-cavity or micro-patch through a non-covalent bond, including without limitation a van der Waals interaction, an electrostatic interaction, a hydrophobic interaction and/or a non-specific adsorption.

In some aspects, the analytes are single cells. The analytes can be contacted with a tag. In some aspects, the tag can recognize a target on the analyte. The tag can bind to the target. In some aspects, the target can be a molecular component of the analyte. In some aspects the molecular component can be exterior to the analyte. In other cases, the molecular component can be interior to the analyte. The tags can be detected using a variety of detection methods.

The disclosure provides a method for containment or physical trapping of single analytes. In some aspects, the analytes can be cells. The cells can be transported in a liquid phase where the liquid can follow the flow path and can transit to a physically defined position. In some aspects, the cells can remain in the defined position. The flow based forces can be placed upon the cell to trap the cell in the defined position. In another case, the cells can be trapped sequentially as the fluidic flow path is serial with respect of inlet to outlet. In yet another case, multiple fluid flowpaths and their commensurate multiple single cells can be trapped or sequestered in a parallel manner. In some aspects, trapping in a parallel manner can be due to the numerous flow paths that can simultaneously be experienced by the cells between the inlet and outlet.

In a preferred case, the method can provide for each analyte (e.g., cell) in a fluid sample to follow a fluid path and enter a chamber. The analyte can enter the chamber and block the fluid path stopping the flow through the fluid path. In this case, another analyte may not enter the chamber. The remaining cells in the fluid sample can enter the remaining empty chambers until some, or all, of the chambers contain an analyte.

In some aspects, the method by which the serial-flow resistance trap functions to collect, discretize, and readout biologically derived samples is disclosed herein. For example, FIG. 22A shows how samples can serially fill defined locations. This process can occur when the critical dimension (diameter) of the sample is, (1) smaller than the height and width of the main channel, and (2) larger than the height or width of the constriction. In some aspects, differential resistance to flow can direct the sample into the defined region, whereupon the constriction can be occluded and flow can be stopped. Subsequent samples can follow a flow path through the main channel, to the next trapping location, until all traps are filled. For example, FIG. 22B shows how an immiscible liquid phase can be introduced through the sample inlet. The immiscible liquid can serially discretizes the trapped samples. In some aspects, the immiscible liquid may not flow into the sample regions. The lack of fluid flow of the immiscible liquid can be attributed to the occluded restriction. In some aspects, the lack of fluid flow can be attributed to an interfacial barrier created by the differential contact angles of the immiscible phases with the channel material and the dimensions of the trapping region. In some aspects, temporal information regarding each sample can be physically encoded in each location. The varying chemical natures of the discretized samples can be detected (FIG. 22C).

In some aspects, the method by which the parallel flow resistance trap functions to collect, discretize, and readout biologically derived samples is disclosed herein. For example, FIGS. 22A and 22D show how samples can fill the parallel flow resistance trap. In some aspects, sample particles can follow the flow from the top of the device into the wells. Multiple samples can be trapped simultaneously in the parallel flow resistance trap. In some aspects, the speed of sample collection can be faster using the parallel flow resistance trap rather than the serial-flow resistance trap. For example, FIG. 22D shows how an immiscible phase can be replaced above and below the plane of the trapping wells. In some aspects, the immiscible phase above and below the plane of the trapping wells can generate the discretized samples. In some aspects, temporal information regarding each sample can be physically encoded in each location. The varying chemical natures of the discretized samples can be detected (FIG. 22C).

Figure 24:
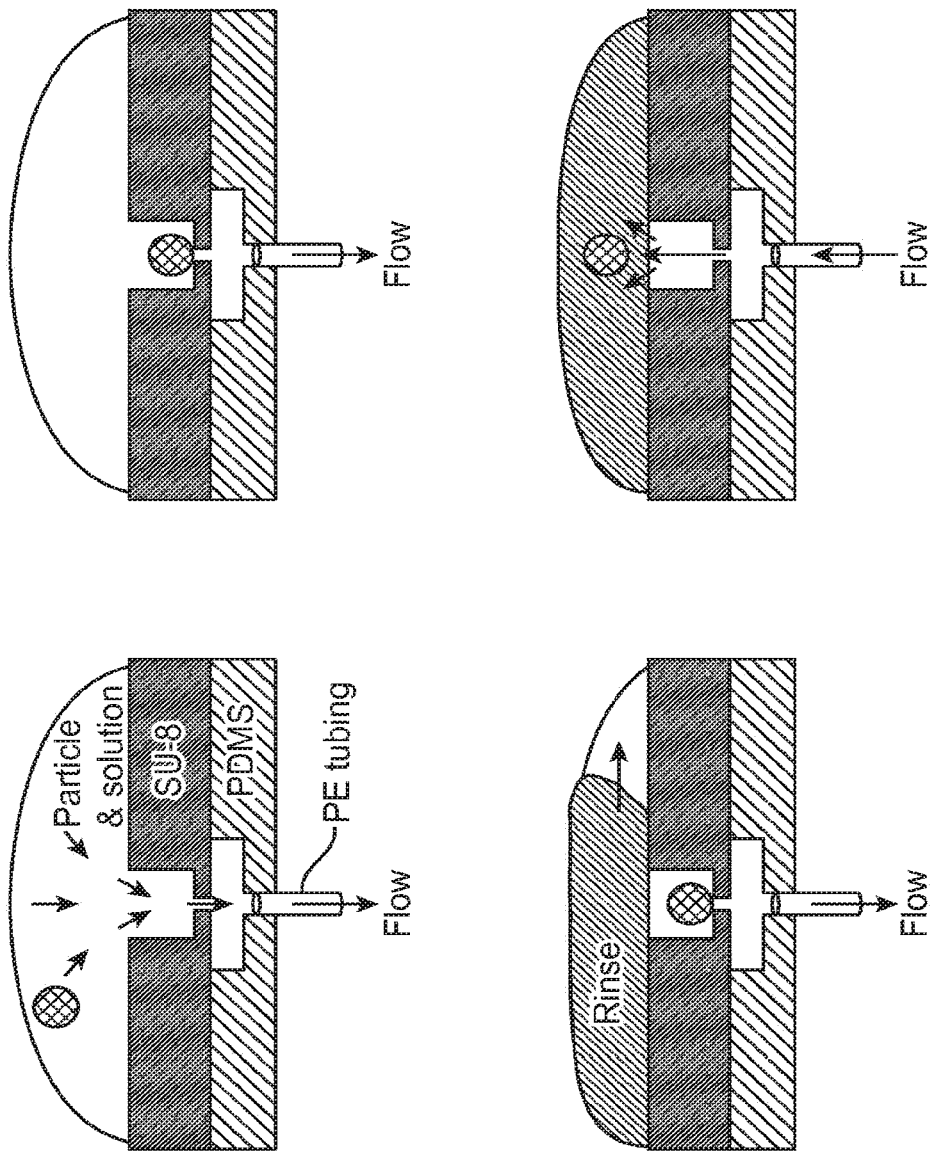
FIG. 24 illustrates the sequence for trapping an array of biological particle/cell for analysis and release according to an aspect of the present disclosure.

In some aspects, the trapped analyte can be released from the single-analyte array and analyzed. For example, FIG. 24 illustrates a possible sequence for trapping an array of biological analytes for analysis and release. In some aspects, the sequence can include, (1) applying flow from the tubing to move the fluid flow through the trap, (2) ceasing the flow in the localized region once analytes are trapped, and, (3) rinsing excess fluid and particles using a buffer.

In some aspects, the analytes trapped in the single-analyte array can undergo further analysis. In some aspects, the single-analyte array can be used with the method of sequential immunostaining and photobleaching.

In some aspects, the single-analyte analyte array can be used with methods known to those of skill in the art for analysis of nucleic acids. In some aspects, the analysis of nucleic acids can include polymerase chain reaction (PCR). In the case of performing PCR using the single-analyte array (FIG. 17), all the chambers can be filled with a single analyte in a fluid. Each chamber can be sealed (e.g., using oil) and PCR can be performed on each single analyte in parallel.

Analytes contained in the individual wells or chambers of the single-analyte array can be detected using a variety of techniques. For example, the analytes in the wells or chambers can be imaged using microscopy. In some aspects, microscopy can include bright field microscopy. In some aspects, microscopy can include fluorescence microscopy. In any case of microscopy, the sample can be placed on a stage. In some aspects, the stage can be manually operated. In other cases, the stage can be an automated translation stage that can be controlled by computer programs. In any case of microscopy, images can be acquired by CCD cameras.

Applications

The disclosure provides for the method to be used in a variety of applications. In some aspects, the method can provide a subject a diagnosis or prognosis for a condition associated with the presence of a rare particle in a fluid sample, for example a biological fluid such as a blood sample.

The methods and apparatuses described herein can comprise the steps of: (a) contacting a biological fluid from the subject with a tag under conditions suitable to transform the tag into a complex comprising said tag and an analyte; (b) detecting the presence or absence of a complex formed in step (a) in an aliquot of the biological fluid; (c) assigning a value to the aliquot based on the presence or absence of a complex formed in step (a); and (d) providing a diagnosis or prognosis to the subject based on analysis of the isolated aliquot. In some aspects, step (b) can comprise interrogating the aliquot with a source of radiation and detecting a signal emitted by the tag bound to the analyte.

In various aspects, methods are provided for identifying a plurality of markers present on an analyte within a fluid, wherein the method comprises: (a) detecting a signal from a first tag using a source of radiation, wherein the first tag is attached to a first structure that binds to a first marker on the analyte; (b) partitioning the analyte based on the presence of the first tag; (c) reducing the intensity of the signal of the first tag; (d) contacting the analyte with a second structure that binds to a second marker, wherein the second structure is attached to a second tag; and (e) detecting the second tag.

In some aspects, the partitioning of step (b) is based on the presence of the first tag and a third tag. In further aspects, the partitioning of step (b) is performed with a microfluidic device. In still further aspects, the partitioning of step (b) and the detecting in at least one of step (b) or step (e) occurs within the same microfluidic device.

In various aspects, methods are provided for detecting a plurality of markers present on an analyte, the method comprising: contacting the analyte with a first tag, wherein the analyte comprises a first marker and the first tag has an affinity for the first marker; detecting a first signal emitted by the first tag, wherein the presence of the first signal indicates the presence of the first marker; partitioning a fluid comprising the analyte based on the presence of the first signal; reducing the intensity of the first signal; contacting the analyte with a second tag, wherein the analyte comprises a second marker and the second tag has an affinity for the second marker; and detecting a second signal emitted by the second tag, wherein the presence of the second signal indicates the presence of the second marker.

In some aspects, the signal of the first tag is reduced by greater than 50%. In certain aspects, reducing the intensity of the signal is accomplished by applying radiation to the analyte. In further aspects, white light is used to reduce the intensity of the signal. In still further aspects, a laser is used to reduce the intensity of the signal. In other aspects, a light emitting diode is used to reduce the intensity of the signal. In some aspects, reducing the intensity of the signal is accomplished by applying a chemical to the first tag. In certain aspects, the chemical is a reducing agent. In further aspects, the reducing agent is dithiothreitol.

In some aspects, partitioning the fluid is based on the presence of the first signal and a third signal. In further aspects, detecting the first signal, detecting the second signal, partitioning the fluid, or a combination thereof is performed using a microfluidic device.

In some aspects, the analyte is a cell. In certain aspects, the cell is a cancerous cell. In further aspects, the cancerous cell is a rare cell. In some aspects, the analyte is a circulating tumor cell. In certain aspects, the cell is a bacterial cell, an immune cell, a fetal cell, a cell indicative of a disease remaining after treatment, or a stem cell. In further aspects, the cell is a rare cell, comprising less than 1% of the total cell population in the fluid. In certain aspects, the analyte is a dissociated cell.

In some aspects, the fluid is selected from the group consisting of: whole blood, fractionated blood, serum, plasma, sweat, tears, ear flow, sputum, lymph, bone marrow suspension, lymph, urine, saliva, semen, vaginal flow, feces, transcervical lavage, cerebrospinal fluid, brain fluid, ascites, breast milk, vitreous humor, aqueous humor, sebum, endolympth, peritoneal fluid, pleural fluid, cerumen, epicardial fluid, and secretions of the respiratory, intestinal and genitourinary tracts. In certain aspects, the fluid is whole blood. In other aspects, the fluid is fractionated whole blood.

In some aspects, the first tag is a fluorophore. In further aspects, the first tag is an antibody. In other aspects, the first tag is a probe comprised of a nucleic acid. In certain aspects, the methods further comprise imaging the signal from the first tag and the second tag. In some aspects, the analyte is present in a fluid, and the fluid is an aliquot of a larger volume of fluid. In further aspects, detecting the first signal emitted by the first tag is performed simultaneously on a plurality of analytes.

In certain aspects, the partitioning is performed semi-automatically or automatically. In certain aspects, the partitioning is performed by ensemble-decision aliquot ranking. In some aspects, a flow cytometer is not used to partition the analyte.

In further aspects, the analyte comprises a plurality of markers. In some aspects, each of the plurality of markers is a biomarker. In certain aspects, the analyte comprises an expression profile, wherein the expression profile is defined by the plurality of markers.

In further aspects, the method further comprises contacting the analyte with a buffer. In still further some aspects, the buffer contains a fixative. In certain aspects, the buffer contains a permeabilization agent. In other aspects, the buffer is a washing buffer.

In various aspects, methods are provided for isolating cells from a sample comprising a first cell type and a second cell type, the methods comprising: (a) introducing the sample into a microfluidic chip via a set of tubing wherein the microfluidic chip comprises (i) at least one channel fluidly connected to the set of tubing; (ii) a detector configured to detect signals of cells within the at least one channel; and (iii) at least one chamber fluidly connected to the at least one channel; (b) flowing a portion of the sample past the detector; (c) using the detector to detect the presence or absence of the first cell type within the portion of the sample; (d) if the first cell type is detected within the portion of the sample, directing an aliquot of the sample into the chamber, wherein the aliquot comprises the first cell type; and (e) repeating steps (b), (c), and (d), thereby isolating multiple aliquots in the chamber such that the chamber comprises greater than 80% of a total number of first cell types within the sample and less than 5% of a total number of second cell types within the sample.

In various aspects, methods are provided for isolating cells from a sample, the methods comprising: (a) introducing the sample into a microfluidic chip, wherein the sample comprises a first cell type and a second cell type, and wherein the microfluidic chip comprises: a channel; a detector configured to detect a signal emitted within the channel; a chamber in fluidic communication with the channel; (b) flowing a portion of the sample through the channel, wherein the portion comprises a plurality of the first cell type, a plurality of the second cell type, or a combination thereof; (c) detecting the presence or absence of the first cell type within the portion using the detector; (d) directing the portion into the chamber if the first cell type is present within the portion; and (e) repeating (b), (c), and (d) a sufficient number of times such that the chamber comprises more than 80% of the total number of the first cell type present within the sample and less than 5% of the total number of the second cell type present within the sample.

In some aspects, at least one of the first cell type and the second cell type is a cancerous cell. In certain aspects, the cancerous cell is a rare cell. In further aspects, at least one of the first cell type and the second cell type is a circulating tumor cell. In still further aspects, at least one of the first cell type and the second cell type is a bacterial cell, an immune cell, a fetal cell, a cell indicative of a disease remaining after treatment, or a stem cell. In some aspects, at least one of the first cell type and the second cell type is a rare cell, comprising less than 1% of the total cell population in the sample.

In some aspects, the sample is selected from the group consisting of: whole blood, fractionated blood, serum, plasma, sweat, tears, ear flow, sputum, lymph, bone marrow suspension, lymph, urine, saliva, semen, vaginal flow, feces, transcervical lavage, cerebrospinal fluid, brain fluid, ascites, breast milk, vitreous humor, aqueous humor, sebum, endolympth, peritoneal fluid, pleural fluid, cerumen, epicardial fluid, and secretions of the respiratory, intestinal and genitourinary tracts. In certain aspects, the sample is whole blood. In other aspects, the sample is fractionated whole blood.

In some aspects, the chamber is external to the microfluidic chip. In certain aspects, wherein the chamber is a vial, a microcentrifuge tube, or a well in a well plate. In further aspects, the chamber is in fluidic communication with the channel via tubing. In still further aspects, the chamber is in fluidic communication with the channel via a capillary tube.

In various aspects, methods are provided for identifying a plurality of markers present on an analyte, wherein the methods comprise: (a) partitioning a plurality of analytes by flowing the analytes over a substrate comprising a plurality of micro-cavities or micro-patches, wherein the majority of micro-cavities or micro-patches are capable of containing not more than one analyte and wherein the micro-cavities or micro-patches are located in a microfluidic device; (b) in the micro-cavities or micro-patches, contacting each analyte with a first structure that is capable of binding to a first marker, wherein the first structure is connected to a first tag; (c) detecting a signal from the first tag; (d) reducing the level of the signal of the first tag; (e) contacting the analyte with a second structure that binds to a second marker, wherein the second structure is connected to a second tag; and (f) detecting the second tag.

In some aspects, the contacting of step (b) is achieved by flowing a fluid comprising the first structure through a channel that is in fluid communication with the micro-cavities or micro-patch. In certain aspects, following the contacting step of step (b), the method further comprises: contacting the analyte with a wash buffer.

In various aspects, methods are provided for detecting a plurality of markers present on an analyte, the methods comprising: isolating an analyte in a micro-cavity or in a micro-patch by flowing a fluid over a substrate comprising the micro-cavity or micro-patch, wherein the fluid comprises the analyte; contacting the analyte with a first tag, wherein the analyte comprises a first marker, and wherein the first tag has an affinity for the first marker; detecting a first signal emitted by the first tag, wherein the presence of the first signal indicates the presence of the first marker; reducing the intensity of the first signal; contacting the analyte with a second tag, wherein the analyte comprises a second marker, and wherein the second tag has an affinity for the second marker; and detecting a second signal emitted by the second tag, wherein the presence of the second signal indicates the presence of the second marker.

In some aspects, the method is performed on a plurality of analytes isolated in a plurality of micro-cavities or micro-patches. In certain aspects, the signal of the first tag is reduced by greater than 50%. In further aspects, at least one analyte is a cell.

In some aspects, an analyte is held in a fixed position within the micro-cavities by a force generated by fluid flow, gravity, or adhesive forces. In certain aspects, an analyte is connected to a micro-cavity or micro-patch through a molecular interaction. In further aspects, an analyte is connected to a micro-cavity through a non-covalent bond. In still further aspects, the non-covalent bond is a van der Waals interaction, an electrostatic bond, a hydrophobic bond or a non-specific adsorption.

In various aspects, methods are provided for isolating an aliquot of a fluid sample within a microfluidic chip, wherein the aliquot comprises a rare particle, the methods comprising the steps of: (a) detecting the presence or absence of the rare particle in the aliquot; (b) assigning a value to the aliquot based on the presence or absence of the rare particle; and (c) directing the flow of the aliquot based on the assigned value by opening an electro-actuated valve, wherein the electro-actuated valve is located on a device that is external to the microfluidic chip. In some aspects, the microfluidic chip comprises a sample input channel, at least two output channels, and at least one directional flow channel, and wherein the electro-actuated valve controls the flow of fluid within the directional flow channel.

Diagnosis of Disease

In some aspects, analytes (e.g., cells) isolated using the present method can be further subjected to subpopulation analysis (e.g., according to genotype or phenotype) to develop a targeted treatment. For example, the isolated cells (e.g., tumor cells) can be incubated with tags (e.g., fluorescent antibodies) binding to specific biomarkers (e.g., drug targets) to determine the presence or degree of expression of a drug target. Once the expression of the drug target is confirmed, drugs can be chosen for therapy that are specifically developed to target the expression of a particular drug target. In one example, the isolated tumor cells can be incubated with fluorescent antibodies binding specifically to Her2 receptor to determine whether the breast tumor shedding CTCs is Her2-positive. If the isolated tumor cells exhibit high Her2 expression, Herceptin (trastuzumab) can be used as a therapy as this drug is designed to target and block the function of HER2 protein overexpression. Other known drug targets, including BCR-ABL or PDGFR (targeted by drug Gleevec), ERBB2 (targeted by Herceptin), EFGR (targeted by Iressa, Tarceva), RAR-alpha (targeted by ATRA), Oestrogen receptor (targeted by Tamoxifen), aromatase (targeted by Letrazole), androgen receptor (targeted by Flutamide, Biclutamide), CD20 (targeted by Rituximab), VEGF-receptor (targeted by Avastin) can also be similarly screened from the isolated tumor cells before prescribing the appropriate chemotherapy regimen.

In some aspects, the analyte can be a rare particle (e.g., a cancer cell or circulating tumor cell (CTC)). In other cases, the rare particle can be a parasitic cell or organism, for example, a species of *Giardia* or *Cryptosporidium*, a erythrocyte infected with a species of *Plasmodium*, a lymphocyte or leucocyte infected with HIV, a fetal cell in maternal blood, a stem cell, a prion-infected cell, a CD4+ T-cell, and the like.

In some aspects, the method can comprise detecting a circulating tumor cell in a blood sample from a subject. The method can include eDAR. In certain aspects, the subject can be a patient who has been diagnosed with cancer. In some aspects, the cancer can be Stage I, Stage II, Stage III, or Stage IV. In some aspects, circulating tumor cells (CTCs) can be detected in a blood sample from a patient previously diagnosed with cancer. In these cases, the patient can be further diagnosed with metastatic cancer.

In some aspects, the method can be used for diagnosing metastatic cancer in a subject that has previously been diagnosed with a solid tumor, the method comprising the steps of: (a) detecting the presence or absence of a CTC in an aliquot of a blood sample from the subject; (b) assigning a value to the aliquot based on the presence or absence of the CTC; and (c) directing the flow or collection of the aliquot based on the assigned value.

In some aspects, the absence of CTCs in the blood sample can be correlated with the subject not having metastatic cancer. The presence of at least one CTC in the blood sample can be correlated with the subject having metastatic cancer. In some aspects, the presence of at least a number of CTCs in the blood can be correlated with the subject having metastatic cancer. The method can further comprise a step of (d) diagnosing the subject as not having metastatic cancer if no CTCs are detected in the blood sample or diagnosing the subject as having metastatic cancer if at least one CTC is detected in the blood sample.

The disclosure also provides for a method for monitoring a subject diagnosed with cancer. The method can comprise detecting the presence or absence of a CTC in an aliquot of a blood sample from the subject using the eDAR method provided herein. In some aspects, the patient can be monitored for the progression of cancer to metastatic cancer at regular intervals, for example, at least once a year, at least twice a year, at least 3, 4, 5, 6, 7, 8, 9, 10, or more times a year, or at least about 3, 4, 5, 6, 7, 8, 9, 10, or more times a year. In some aspects, the subject can be monitored once a month, or at least 2, 3, 4, 5, 6, 7, 8, 9, 10, or more times a month. In some aspects, the subject can be monitored about once a month, or at least about 2, 3, 4, 5, 6, 7, 8, 9, 10, or more times a month. The absence of CTCs in the blood sample can be correlated with the subject not having metastatic cancer. The presence of at least one CTC in the blood sample can be correlated with the subject having metastatic cancer. The presence of at least a number of CTCs in the blood can be correlated with the subject having metastatic cancer.

In cases wherein a CTC is detected in a blood sample, the method can further comprise a step of subjecting one or more aliquots identified as containing a CTC to further analysis to identify one or more characteristics of the CTC cell or cells. For example, an aliquot or pool of aliquots containing a CTC can be contacted with one or more detection reagents specific for one or more cancer-specific surface antigens. Non-limiting examples of cancer-specific surface antigens that can be assayed for include, without limitation, BCR-ABL or PDGFR (targeted by drug Gleevec), ERBB2 (targeted by Herceptin), EFGR (targeted by Iressa, Tarceva), RAR-alpha (targeted by ATRA), Oestrogen receptor (targeted by Tamoxifen), aromatase (targeted by Letrazole), androgen receptor (targeted by Flutamide, Biclutamide), CD20 (targeted by Rituximab), VEGF-receptor (targeted by Avastin), and the like. In some aspects, the surface antigens can be assayed using the sequential immunostaining and photobleaching method described herein.

The methods and devices provided herein can be used to diagnose diseases other than cancer. In some aspects, malaria can be diagnosed, the method comprising detecting an erythrocyte infected with *Plasmodium*. In another case, a method for diagnosing an HIV infection is provided, the method comprising detecting a lymphocyte or leucocyte infected with the HIV virus using an eDAR method and/or apparatus provided herein. In yet another case, a method for diagnosing a disease associated with a prion is provided, the method comprising detecting a prion in a biological fluid from a human or other animal.

In some aspects, the analyte is a rare cell and the rare cell is a bacterial cell. In some aspects, the bacterial cell is present in a whole blood sample. In other aspects, a device, method, system or apparatus is used to detect the presence of the rare bacterial cell in whole blood. In some aspects a device, method, system or apparatus is used to detect the presence of a rare bacterial cell in a whole blood sample in order to provide a diagnosis, prognosis, or other therapeutic parameter related to characterizing or managing a bacterial infection or sepsis.

Prognosis of Disease

The present disclosure provides methods for a prognosis for a disease or condition associated with the presence of an analyte in a fluid. In some aspects, the analyte can be a biological particle. In some aspects the fluid can be a biological fluid. In some aspects, the method comprises the steps of: (a) detecting the presence or absence of the analyte in an aliquot of a sample from a subject; (b) assigning a value to the aliquot based on the presence or absence of the analyte; (c) directing the flow or collection of the aliquot based on the assigned value; and (d) providing either a good prognosis if no analytes are detected in the sample or a poor prognosis if analytes are detected in the sample.

In some aspects, the aliquot can be assigned a value based on the quantity or the identity of the analytes in the aliquot. In some aspects, a good or poor prognosis can be provided based on the quantity of the analytes in the sample. For example, a good prognosis can be provided if the quantity of the analytes in the sample is less than a predetermined reference value and a poor prognosis is provided if the quantity of the analytes in the sample is equal to or greater than the reference value. In some aspects, a predetermined reference value can be associated with a likelihood of responding to a particular therapy or a likelihood of overall or disease free survival for a period of time, for example at least 6 month, or at least 1, 2, 3, 4, 5, 6, 7, 8, 9, 10, 15, 20, or more years.

In some aspects, a method provided herein can be used to provide a prognosis for any disease associated with a rare particle. In some aspects, a method for providing a prognosis for malaria is provided, the method can comprise determining the number of erythrocytes infected with *Plasmodium* in a blood sample from an individual using an eDAR method and/or apparatus provided herein. In some aspects, either a good prognosis if the total number of infected erythrocytes detected in the blood sample is less than a predetermined reference value or a poor prognosis if the total number of infected erythrocytes detected in the sample is equal to or greater than the reference value can be provided. In some aspects, a method for providing a prognosis for an HIV infection is provided, the method can comprise determining the number of lymphocytes or leucocytes infected with an HIV virus in a blood sample from an individual using an eDAR method and/or apparatus provided herein and providing either a good prognosis if the total number of infected cells detected in the blood sample is less than a predetermined reference value or a poor prognosis if the total number of infected cells detected in the sample is equal to or greater than the reference value. In some aspects, a method for providing a prognosis for a disease associated with a prion is provided, the method can comprise determining the number of prions in a biological fluid sample from a subject using an eDAR method and/or apparatus provided herein and providing either a good prognosis if the total number of prions detected in the sample is less than a predetermined reference value or a poor prognosis if the total number of prions detected in the sample is equal to or greater than the reference value.

In some aspects, the present disclosure provides a method for providing a prognosis for a subject diagnosed with a solid tumor. In some aspects, the method comprises the steps of (a) detecting the presence or absence of a CTC in an aliquot of a blood sample from the subject; (b) assigning a value to the aliquot based on the presence or absence of the CTC; (c) directing the flow or collection of the aliquot based on the assigned value; and (d) providing either a good prognosis if no CTCs are detected or a poor prognosis if a CTC is detected.

In some aspects, a method is provided for providing a prognosis for a subject diagnosed with metastatic cancer. In some aspects the method comprises the steps of (a) detecting the presence or absence of a CTC in an aliquot of a blood sample from the subject; (b) assigning a value to the aliquot based on the number CTCs detected in the aliquot; (c) directing the flow or collection of the aliquot based on the assigned value; and (d) providing a good prognosis if the total number of CTCs detected in the blood sample is less than a predetermined reference value or a poor prognosis if the total number of CTCs detected in the sample is equal to or greater than the reference value.

In some aspects, a predetermined reference value can be associated with a likelihood of responding to a particular therapy or a likelihood of overall or disease free survival for a period of time, for example at least 6 month, or at least 1, 2, 3, 4, 5, 6, 7, 8, 9, 10, 15, 20, or more years.

Response of Disease to Treatment

The present disclosure provides methods for monitoring the progression of a disease or the response to a therapy. In some aspects, the method can comprise detecting an analyte in a fluid sample. In some aspects, the method comprises the steps of: (a) detecting the presence or absence of the analyte in a plurality of aliquots of a first biological sample taken from a subject at a first time; (b) assigning a value to the aliquots based on the presence, absence, quantity, or identity of the rare particle; (c) determining the total value of all the aliquots from the first sample; (d) detecting the presence or absence of the analyte in a plurality of aliquots of a second biological sample taken from the subject at a second time; (e) assigning a value to the aliquots based on the presence, absence, quantity, or identity of the analyte; (f) determining the total value of all the aliquots from the second sample; and (g) comparing the total value assigned to the first sample to the total value assigned to the second sample, wherein an increased value assigned to the second sample as compared to the first sample is correlated with a progression of the disease and/or a poor response to the therapy and/or a decreased value assigned to the second sample as compared to the first sample is correlated with a regression of the disease and/or a good response to the therapy. In some aspects, the aliquots can further be directed into a particular channel or chamber (channeled) based on the value assigned for collection, further enrichment, or further analysis.

In some aspects, methods of monitoring disease progression or response to therapy can be employed on a regular basis after diagnosis of the disease or initiation of the treatment regime. For example, samples can be collected from a subject at least once a year, at least twice a year, at least 3, 4, 5, 6, 7, 8, 9, 10, or more times a year, or at least about 3, 4, 5, 6, 7, 8, 9, 10, or more times a year. In some aspects, the subject can be monitored once a month, or at least 2, 3, 4, 5, 6, 7, 8, 9, 10, or more times a month. In some aspects, the subject can be monitored about once a month, or at least about 2, 3, 4, 5, 6, 7, 8, 9, 10, or more times a month.

In some aspects, wherein a progression of the disease or poor response to a therapy is found, the method can further comprise a step of assigning a therapy, increasing a dosage regime, changing a therapeutic regime, and the like. In some aspects, the disease or condition associated with a rare particle can be cancer, malaria, HIV/Aids, a prion-related disease, or the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. The term "about" as used herein refers to a range that is 15% plus or minus from a stated numerical value within the context of the particular usage. For example, about 10 would include a range from 8.5 to 11.5.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice. The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, $3^{rd}$ Edition or a dictionary known to those of skill in the art, such as the Oxford Dictionary of Biochemistry and Molecular Biology (Ed. Anthony Smith, Oxford University Press, Oxford, 2004).

As used herein and unless otherwise indicated, the terms "a" and "an" are taken to mean "one," "at least one" or "one or more." Unless otherwise required by context, singular terms used herein shall include pluralities and plural terms shall include the singular.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to."

Unless otherwise specified, the presently described methods and processes can be performed in any order. For example, a method describing steps (a), (b), and (c) can be performed with step (a) first, followed by step (b), and then step (c). Or, the method can be performed in a different order such as, for example, with step (b) first followed by step (c) and then step (a). Furthermore, those steps can be performed simultaneously or separately unless otherwise specified with particularity.

Words using the singular or plural number also include the plural and singular number, respectively. Additionally, the words "herein," "above," and "below" and words of similar import, when used in this application, shall refer to this application as a whole and not to any particular portions of the application.

EXAMPLES

The following examples are included to further describe some aspects of the present invention, and should not be used to limit the scope of the invention.

Example 1

Ensemble-Decision Aliquot Ranking Based on Microfluidic Components for Large-Capacity Trapping of Circulating Tumor Cells This example describes and validates a novel eDAR platform for isolating particles including cells according to an aspect of the present disclosure.

Two factors that determined the feature and performance of an eDAR platform are an efficient and active sorting scheme and a subsequent efficient purification (e.g., purification chamber) scheme. The present eDAR-platform optimizes these two components. In one example, the eDAR platform can include an integrated filtration area fabricated by standard lithography methods. The microfluidic chip can be composed of two layers on a silicon master and can be fabricated with one-step replica molding into polydimethylsiloxane (PDMS). The microfluidic chip can be finished with bonding to a glass substrate. The entire system can include an active sorting scheme. The analytical performance of the microfluidic chip and hydrodynamic switching mechanisms can be optimized for a particular recovery efficiency (e.g., 95%), a particular false positive rate (e.g., 0) and a particular throughput (e.g., 4.8 mL of whole blood per hour).

The Microfluidic Chip

The microfluidic chip used in this example had two functional areas integrated in the same design, the eDAR sorting area and the filtration unit based on slit structures. The main channel in the sorting unit, which introduced the blood into the sorting junction, had a height of 50 μm and width of 150 μm; all the other 4 channels were 50 μm tall and 200 μm wide. The slit-filters were 5 μm tall and 5 μm wide. The maximum number of slits tested was 20,000.

The silicon master was fabricated using two photolithography processes (FIGS. 5, 20 and 21). The features were designed using AutoCAD (Autodesk, San Rafael, CA), and written on a chrome mask (TRICR Corporation, SF, CA). Positive resist lithography and deep reactive ion etching (DRIE) were chosen for forming the first layer, the microfilter feature. AZ 1512 was used as a positive photoresist, which was provided by Micromanufacturing Facility (MMF) at The University of Washington. DRIE process was optimized to achieve a depth in the range of 4.5-5 μm. The second layer of the eDAR feature was fabricated using the SU-8-3050 as a negative photoresist (MicroChem, Newton, MA), and the height of the feature was controlled to be 50 μm. After the master was silanized using tridecafluoro-1,1,2,2-tetrahydrooctyl-1-trichlorosilane (Sigma-Aldrich, St. Louis, MO), uncured PDMS was poured onto the silicon wafer and baked for 2 hours at 70° C. The piece of PDMS with the desired micro-feature was peeled off the silicon master, and then bonded with a piece of cover glass using the standard process of plasma oxidation.

Biological and Clinical Samples

Three breast cancer cell lines, SKBr-3, MCF-7, and MDA-MB-231 cells (American Type Culture Collection (ATCC), Manassas, VA) were used to characterize and optimize the eDAR system. SKBr-3 cells were cultured in McCoy's 5, MCF-7 was cultured in Eagle's Minimum Essential Medium (EMEM), and MDA-MB-231 was cultured in Dulbecco's Modified Eagle's Medium (DMEM) (ATCC, Manassas, VA). All cell culture media also contained 2 mM L-glutamine, 10% fetal bovine serum (PBS) (ATCC, Manassas, VA), and 50 μg/mL penicillin/streptomycin (ATCC, Manassas, VA). Incubations were done at 37° C.

with 5% $CO_2$ in a humidified environment. The MDA-MB-231-GFP cell line was provided by Prof. Gail Sonenshein at Tuffs University and cultured in the DMEM medium with 10% FBS and 1 µg/mL puromycin (Life Technologies, Carlsbad, CA). Control blood from healthy donors was purchased from Plasma International Lab (Everett, WA); the first tube of the blood draw was discarded to prevent any possible contamination from skin cells. Whole blood samples were drawn from patients with metastatic pancreatic cancer based on a protocol approved by Fred Hutchinson Cancer Research Center's institutional review board. Patient samples were collected at the Seattle Cancer Care Alliance (SCCA) using Vacutainer tubes (BD, Franklin Lakes, NJ) containing EDTA as an anti-coagulant, stored at 4° C., and analyzed within 4 hours.

Sample Preparation and eDAR Analysis

Isoton (Beckman Coulter Inc., Chino, CA) was used as the buffer for all the experiments unless otherwise specified. For a typical eDAR experiment, 1 mL of whole blood samples was labeled with anti-EpCAM conjugated with phycoerythrin (PE) (Lot No. 515776, Abnova, Walnut, CA) for 30 minutes at room temperature in dark. All the labeling parameters have been optimized. The labeled samples were diluted to 14 mL and then centrifuged to remove the free antibodies. The final volume was adjusted to be the same as the initial volume. The prepared sample was next injected to the microfluidic chip using a syringe pump. Traces from fiber-coupled avalanche photodiodes (APDs) (Excelitas Technologies, Waltham, MA) were collected by a PCI data acquisition card (PCI 6602, National Instruments, Austin, TX). The sorting process of eDAR was automatically controlled using a home-written LabVIEW (National Instruments, Austin, TX) script and a field-programmable-gate-array (FPGA) device built in house. The hydrodynamic switching, which collected the sorted aliquots, was controlled by a solenoid (INKA1226212H) purchased from the Lee Company (Westbrook, CT).

After all the positive aliquots were collected onto the filtration area, isoton was used to quickly wash the filtration area in less than 1 minute. If any cytoplasmic markers were used for the secondary labeling, 4% of paraformaldehyde (PFA) was loaded into the filtration area to fix the cells. Surfynol® 465 (Air product, Allentown, PA) was used to permeabilize the fixed cells. Anti-EpCAM-PE and anti-Cytokeratin-APC (Lot No. MAB5131, Abnova, Walnut, CA) and anti-CD45− fluorescein isothiocyanate (FITC) (Lot No. B116314, BioLegend San Diego, CA,) were typically used as the antibodies for the secondary labeling. Hoechst (Life Technologies, Carlsbad, CA) was also used as the nuclear stain to verify the labeled target was actually nucleated cells.

The method of eDAR was as follows, the blood sample was injected into the microfluidic chip and divided into aliquots. A line-confocal detection scheme was then applied to rank the aliquots as "positive" or "negative," which was determined by the labeling scheme. For example, in many applications, blood was labeled with anti-EpCAM-PE so only an aliquot that had a fluorescent signal from the particular dye conjugated to that antibody was ranked as a positive event. An automatic feedback scheme was applied to generate a switch of the direction of blood flow, which permitted the positive aliquot to be collected quickly. Due to the very low concentration of CTCs, more than 99.999% of the aliquots were discarded because of the absence of the desired fluorescence signal. Those aliquots that gave the positive fluorescence signal were transferred to another area on the microfluidic chip to be further purified and then counted. A series of downstream analyses can be performed on the trapped cells, such as a secondary immunostaining step, a more complicated staining/bleaching process, or the manipulation and culture at the single-analyte level.

Redesigned Hydrodynamic Sorting Scheme.

Previously, the eDAR had a mechanical valve to control the active sorting step, which was fast (about 2 milliseconds response time) and robust compared to other reported switching mechanisms, such as the electroosmotic flow or the sol-gel transformation. Although promising, some design factors of this mechanical valve scheme potentially constrained the potential application of eDAR. To form the mechanical valve on the microfluidic chip, 3 individual structural layers were required—the solenoid, its PDMS thread, and the microchannels on a 150 µm PDMS film. This would make the microfluidic chip preparation complicated and time-consuming Another shortcoming was the direct contact between the captured blood aliquots and the mechanical valve, which potentially increased the risk of the loss or damage of CTCs. In the present example, the solenoid was replaced with an off-chip model, which is normally closed but can be opened in 2 to 3 milliseconds when a 5V DC voltage is applied. Because this in-line solenoid was not a part of the microfluidic chip, the preparation of the microfluidic device was significantly simplified. The solenoids can be easily connected with any microchannels to test hydrodynamic sorting schemes. Eight different schemes were designed and tested (FIG. 6) to drive the fluidic switch. Because of the structure of this type of solenoid and the elastic nature of PDMS, the fluidic performance varied (Table 1), and each scheme was characterized for the best performance.

Figure 7:
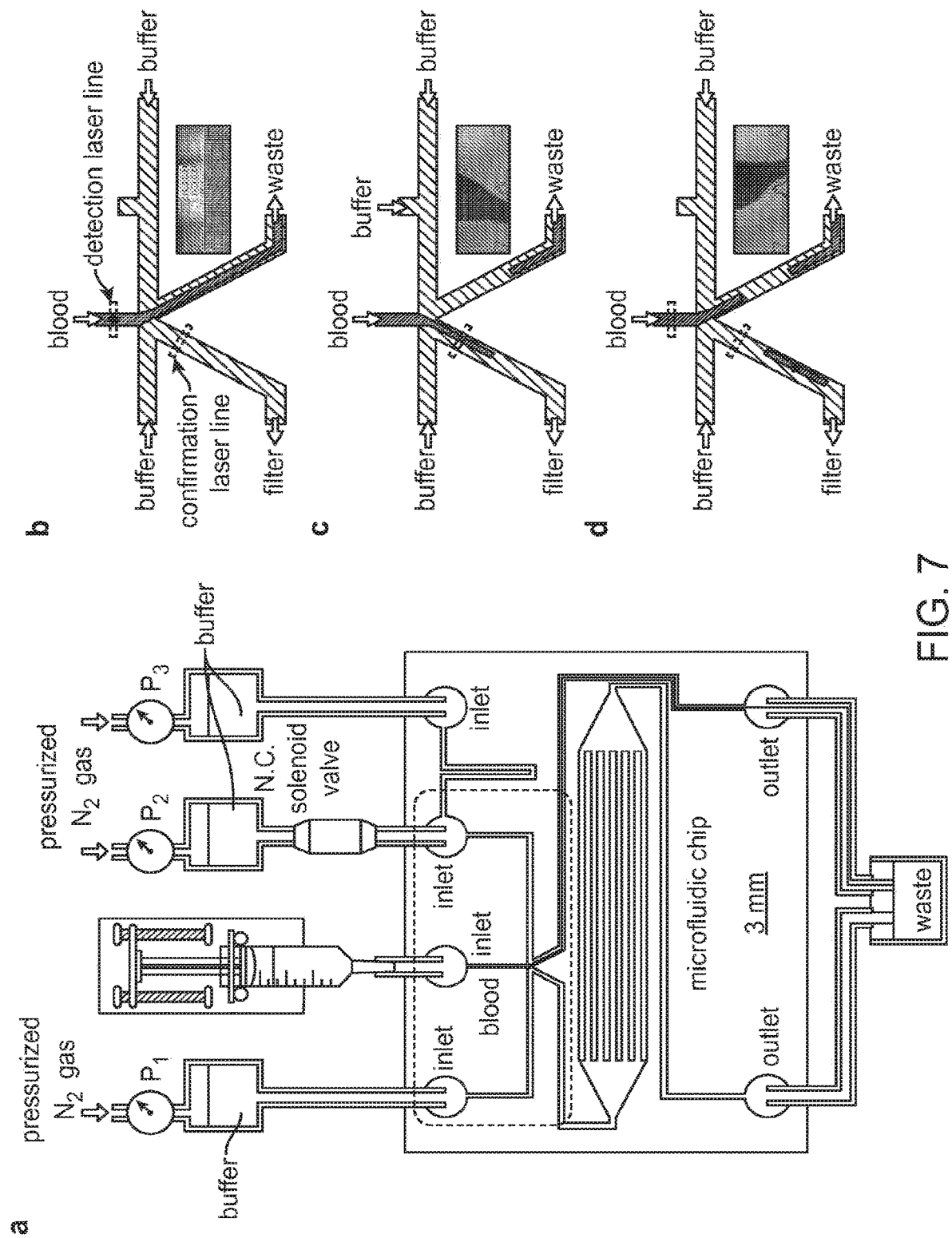
FIG. 7 shows the microfluidic chip and hydrodynamic switching scheme of ensemble eDAR according to an aspect of the present disclosure.

After characterization and optimization, the structure of the platform and the corresponding scheme of the hydrodynamic sorting were chosen for eDAR (FIG. 7). The labeled blood sample was injected into the top channel of the microfluidic chip using a syringe pump (FIG. 7a). Two side channels, where buffer flowed through, were used to control the active sorting step. There were two ports placed on the right-side channel, and both of them were connected to a pressurized buffer source. The normally closed solenoid was connected to the port near the sorting junction to control the hydrodynamic switch. There were two channels after the sorting junction. The one on the left was used to collect positive aliquots and deliver them to the filtration and collection area for further purification (e.g., purification chamber); the one on the right was the waste collection channel where all the negative aliquots flowed through.

Figure 8:
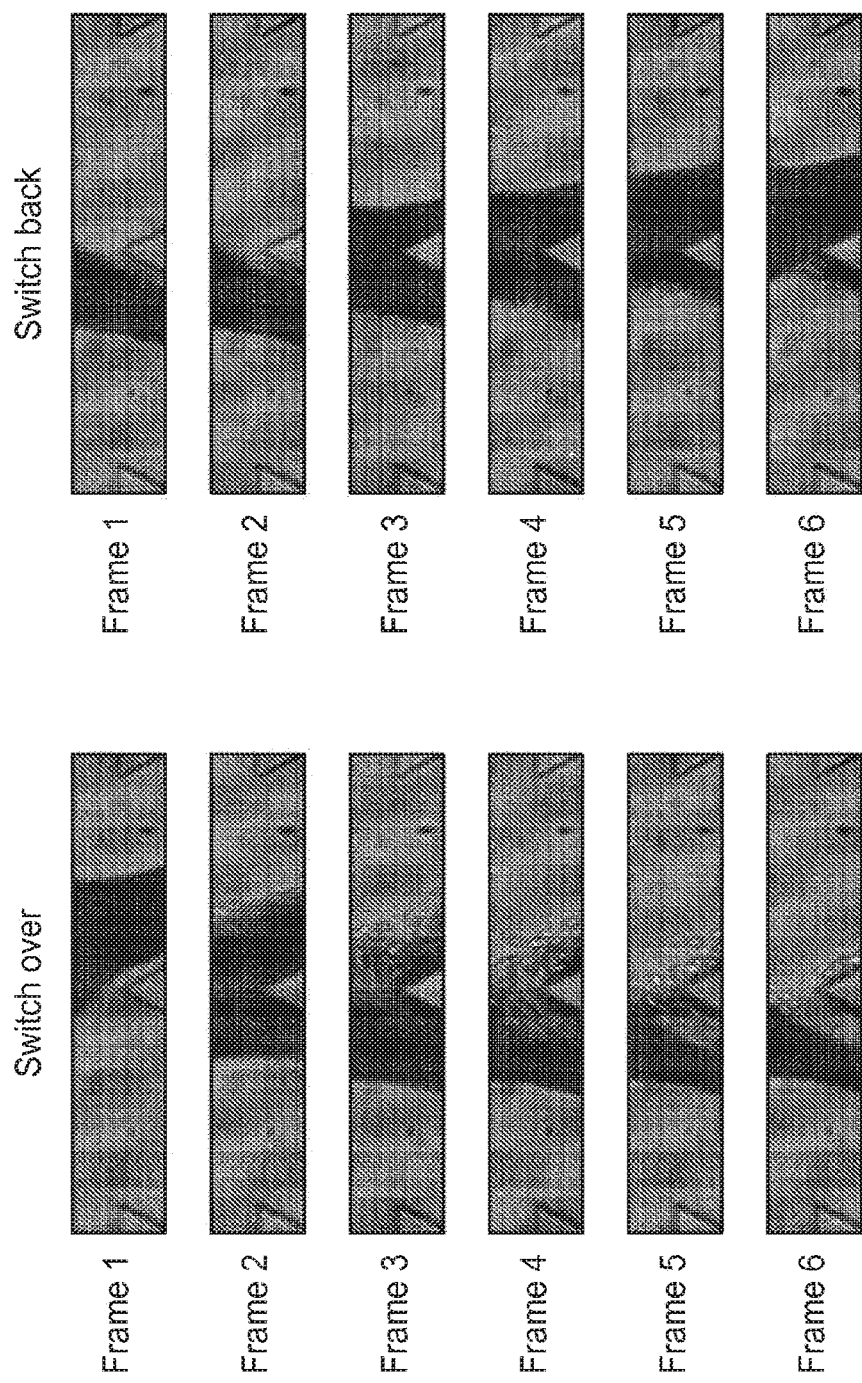
FIG. 8 depicts an example of the switching time for the current fluidic scheme recorded by high speed camera according to an aspect of the present disclosure.

When those aliquots were ranked as "negative" (FIG. 7b), there was no voltage applied on the solenoid so it was closed. An initial pressure drop was set between the No. 1 and 3 buffer sources so the blood could only flow into the channel that collected the waste, which is also shown in the bright field image in FIG. 7b. When a positive event was detected by the first detection window, a 5V DC voltage was immediately applied on the solenoid to open the buffer flow from the No. 2 buffer reservoir. This decreased the flow resistance of the buffer channel on the right side and generated a higher flow rate there. The blood flow was pushed from the right side to the left to collect the positive aliquot (FIG. 7c). After this aliquot was collected and confirmed by the second detection window, the solenoid was closed to switch the blood flow back to the waste collection channel (FIG. 7d). The time required for the switch-over and back was determined to be 2 to 3 milliseconds for each (FIG. 8). This process was stable enough for eDAR even after more than $10^5$ on-off cycles tested. The in-line solenoid was placed on the buffer line so blood could not come into contact with the solenoid, which eliminated the possibility of the blood-coagulation and cross-contamination. Moreover, in this scheme, there was a constant flow of buffer in the CTC collection channel during the eDAR process. This improved the efficiency of the subsequent purification (e.g., purification chamber) step and prevented the formation of aggregates of cells.

In some aspects of the present example, positive aliquots can be collected onto the filtration area and Isoton used to wash the filtration area in less than 1 minute. Cytoplasmic markers can be used for secondary labeling and can involve loading of 4% paraformaldehyde into the filtration area to fix the cells. Surfynol® 465 (Air product, Allentown, PA) can be used to permeabilize fixed cells. Anti-EpCAM-PE and anti-Cytokeratin-APC (Abnova, Walnut, CA) and anti-CD45– fluorescein isothiocyanate (FITC) (BioLegend San Diego, CA,) can be used secondary labeling. Hoechst (Life Technologies, Carlsbad, CA) can be used as a nuclear stain to verify nucleated cells.

Design of the Purification (e.g., Purification Chamber) Mechanism

Yet another aspect of the example can include a new scheme of on-chip filtration based micro-slit structures that can be made of PDMS and may not require additional layers (FIG. 10a). FIG. 10a shows the basic structure of an example of these microslits, which was used to capture the CTCs without retaining any red blood cells (RBCs). The size of the slit was optimized to be 5 μm tall and 5 μm wide (FIG. 10b), to avoid loss of any small CTCs. Many WBCs were not captured using this size of filter, which is smaller than the ones used in most of the CTC methods based on filtration. Because the micro-filter was made of PDMS and bonded with a piece of coverslip, the imaging quality was improved significantly (FIGS. 10c and 10D) compared to the polycarbonate filter, which is not fully transparent and can generate the scattering and aberration. Moreover, because the cells could only be trapped along the array of slits, they could be easily referenced and tracked; in many other methods, the cells are distributed randomly on the surface. This trapping along the slits made the imaging procedure faster and the results of enumeration more accurate. The slits also made it faster and more efficient to perform the secondary labeling on the trapped CTCs. FIG. 10e shows that two cancer cells labeled with anti-EpCAM-PE were trapped on the microslit. Cells were fixed, permeabilzed, and labeled using anti-Cytokeratin-Alexa488, anti-Her2-Alexa647 and Hoechst. Fluorescence images showed the expression of these markers on these two cells clearly, and the bright field image also confirmed their morphology. Two cells were also labeled with anti-CD45-Alexa700 as a negative control marker, and no signal from the color channel corresponded to this tag.

Characterization and Analytical Performance of eDAR

Figure 9:
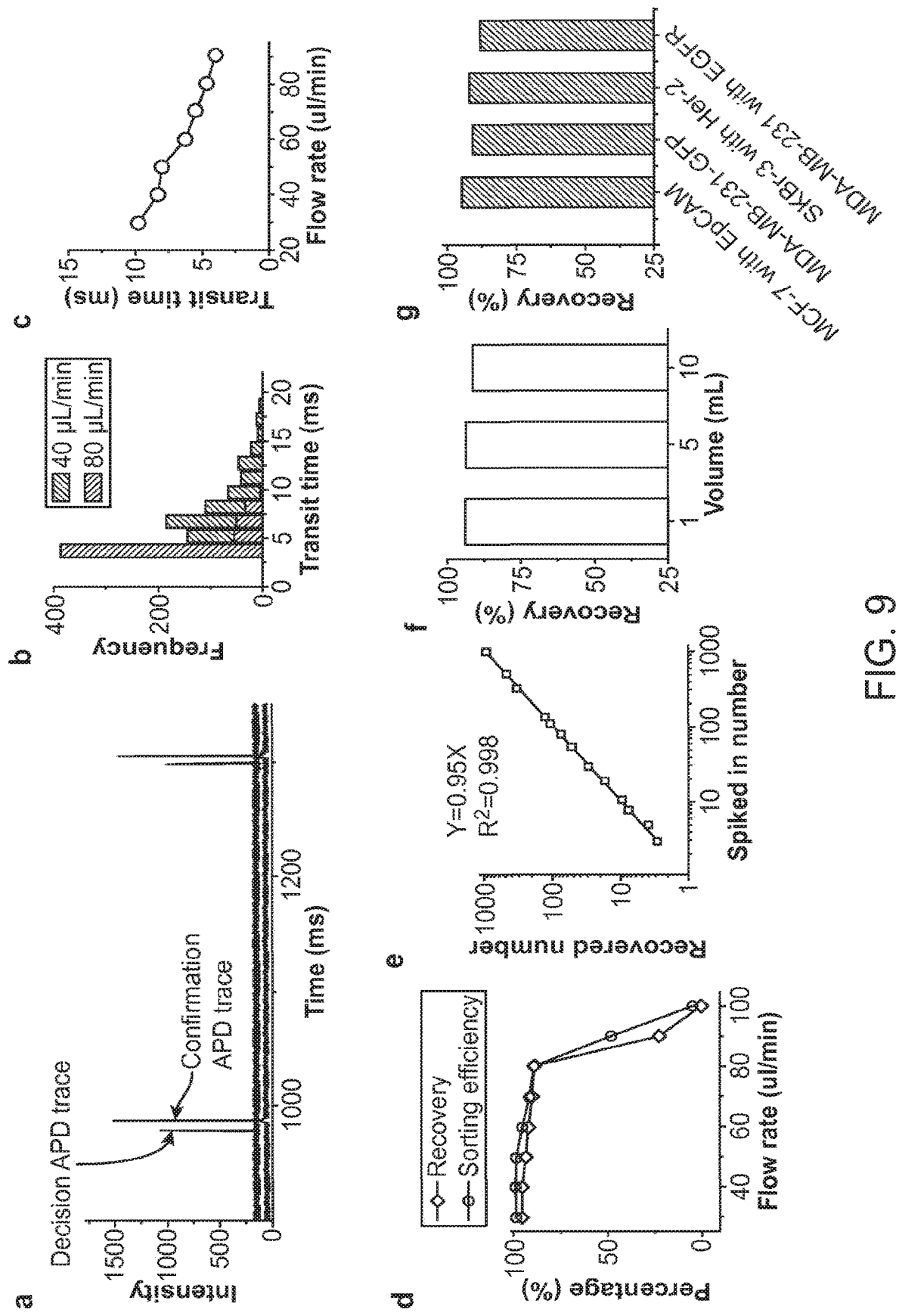
FIG. 9 shows the characterization and analytical performances of eDAR according to an aspect of the present disclosure.

The efficiency of the active sorting step was monitored in real time. FIG. 9 shows a small portion of the APD data from a pancreatic cancer patient sample. The "Decision APD trace" was from the first detection window that ranked the aliquots and controlled the sorting. The two peaks at 978 and 1298 milliseconds represented two CTCs labeled with anti-EpCAM-PE that triggered the aliquot sorting. The two peaks of the "Confirmation APD trace" show that two cancer cells flowed through the second detection window located on the collection channel, confirming that the two positive aliquots were actually sorted. It is worthwhile to point out that the background change from the second detector (FIG. 9a) also confirmed that only a small portion of blood was collected by eDAR, contributing to the high enrichment ratio of CTCs (up to a million fold for a typical clinical sample).

Because the labeled CTC had to flow from the first detection window to the second one, a time difference between the decision APD peak and its confirmation signal was observed. This time difference was defined as the transit time of the sorted CTCs, which can vary because the CTCs can have different linear flow rates due to the nature of laminar flow in the microchannel. FIG. 9b shows the distribution histogram of the transit time at flow rates of 40 and 80 μL/min. Generally, a higher volumetric flow rate of the blood resulted in a shortened transit time of the sorted CTCs (FIG. 9c). When the flow rate was 90 μL/min, the average transit time was lowered to 4 milliseconds, very close to the switching time of the sorting scheme (2 to 3 milliseconds), which implies that this is the limit for the throughput for this particular embodiment of a design for eDAR. In other embodiments, the present eDAR design may yield transit times less than 2 milliseconds.

If the transit time for a sorted CTC was shorter than the hydrodynamic switching time, the cell may not have been reliably sorted on this platform. The sorting efficiency was thus defined as the number of collected events versus the total number of events that triggered the sorting. FIG. 9d shows the values of sorting efficiency at the flow rate of 30 to 100 μL/min. When the flow rate was 30 μL/min, the sorting efficiency was almost 100% because the average transit time at that flow rate was around 10 milliseconds (FIG. 9c). This transit time was long enough for the active sorting step to collect the CTCs. The sorting efficiency decreased to 90% at the flow rate of 80 μL/min, and then dropped to 49% when the flow rate was 90 μL/min. FIG. 9d also shows the recovery efficiency of eDAR at different flow rates, which had a similar trend compared to the sorting efficiency. However, the recovery efficiency was defined as the number of spiked-in cells versus the number of recovered cells counted using multicolor fluorescence imaging on the microfluidic chip. This performance is a combination of many factors, including the antibody-labeling efficiency, the line-confocal detection efficiency and the sorting efficiency. This explains the difference between the recovery and sorting efficiency at the same flow rate. As a result, for this current generation of eDAR, the upper limit of the throughput was 80 μL/min (12.5 minutes for 1 mL of blood) with an 88% recovery ratio. Although this throughput is higher than most CTC technologies for the analysis of whole blood, it can be further improved by designing a wider blood inlet channel or moving the first detection beam farther up.

Three to 975 MCF-7 cells were spiked into 1 mL of healthy blood to analyze the recovery efficiency at the flow rate of 50 μL/min. To ensure the accuracy of the cell numbers at the low end, a capillary counting method was used to precisely spike in cultured cells when the concentration was lower than 100 cells/mL. The average recovery ratio was 95% with an $R^2$ value of 0.998 (FIG. 9e), which is a little higher than the first generation of eDAR (93%). Because the concentration of CTCs is usually very low, the enumeration results were affected by the Poisson distribution. In this case, the ability to analyze a larger volume of whole blood sample with an acceptable throughput and recovery ratio was very important. The same number of MCF-7 cells was spiked into 1, 5 and 10 mL of healthy blood, and then these three samples were analyzed at the flow rate of 50 μL/min. There was no significant change in their recovery ratio (FIG. 9l), which shows that the method is capable of running a large amount of whole blood with high efficiency and throughput.

Although EpCAM was used in most of the CTC studies to select tumor cells, increasingly more studies have reported that CTCs with a low EpCAM expression have more mesenchymal characteristics and are more aggressive. The latest eDAR platform is sufficiently flexible to use any labeling scheme to select rare cells to capture tumor cells using biomarkers other than EpCAM. Three schemes were designed to select different cultured breast cancer cell lines (FIG. 9g). EpCAM was used to select MCF-7 cells, Her-2 was used to select SKBr-3 cells, and EGFR was used to select MDA-MB-231 cells. All these three schemes isolated and trapped the targeted cells with a recovery ratio higher than 88%. Another unique and important feature of eDAR is the independence of where the marker is located. For example, in other technologies, such as the surface capture methods or immunomagnetic methods, only can capture the antigens on the cell surface. The present method was able to select cells with an intracellular marker, such as GFP (FIG. 9d). The recovery ratio of the MDA-MB-231-GFP cells spiked into whole human blood was 91% (FIG. 9g). Since fluorescent proteins are widely used in animal models to study the progression and mechanisms of metastasis, eDAR is an ideal tool to select CTCs in these models without any immunostaining steps.

High-Throughput Analysis of Samples from Patients with Pancreatic Cancer

Figure 25:
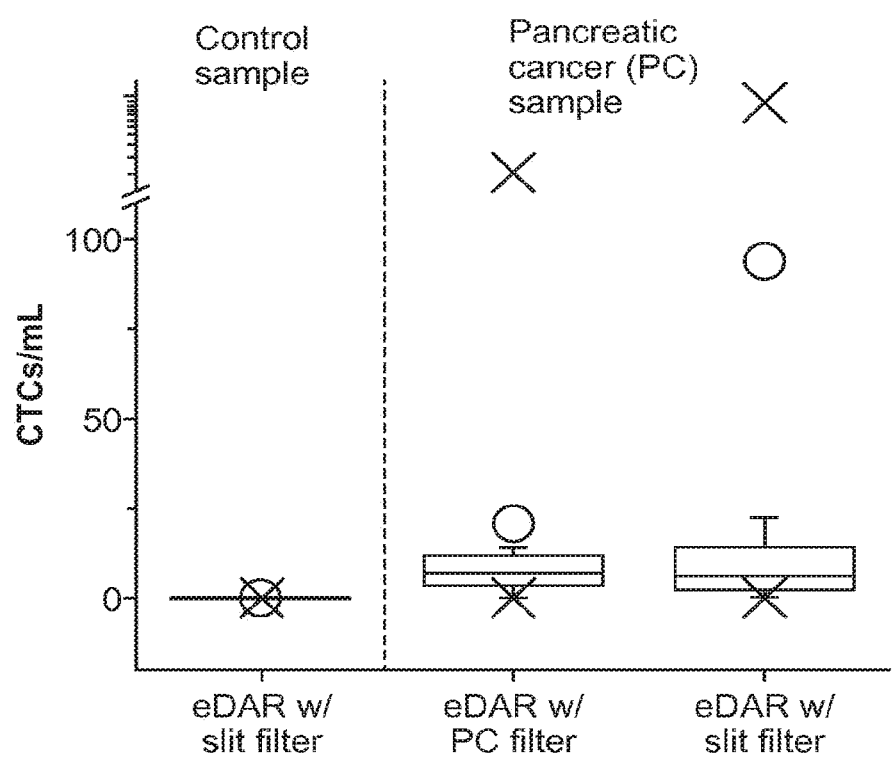
FIG. 25 shows the distribution of 15 control samples and 10 pancreatic cancer samples that can be analyzed by the method reported herein according to an aspect of the present disclosure.

Blood samples from 15 healthy donors were used to evaluate the false positive ratio of this method; no CTCs were found in any of them. 26 blood samples were collected from the patients with pancreatic cancer. Sixteen of them were analyzed using the first generation of eDAR and the other 10 samples were analyzed using the newer eDAR platform. FIG. 25 shows the distribution of the three data sets: the control blood analyzed by the current method, pancreatic cancer samples analyzed by the first generation of eDAR, and the pancreatic cancer samples analyzed by the current method. The raw data of those clinical samples are in Table 3 (below).

TABLE 3

Shows raw data of the control and the pancreatic cancer samples.

| Sample | Volume (mL) | CTC counts |
|---|---|---|
| Control 1 | 1 | 0 |
| Control 2 | 1 | 0 |
| Control 3 | 1 | 0 |
| Control 4 | 1 | 0 |
| Control 5 | 1 | 0 |
| Control 6 | 1 | 0 |
| Control 7 | 1 | 0 |
| Control 8 | 1 | 0 |
| Control 9 | 1 | 0 |
| Control 10 | 1 | 0 |
| Control 11 | 1 | 0 |
| Control 12 | 1 | 0 |
| Control 13 | 1 | 0 |
| Control 14 | 1 | 0 |
| Control 15 | 1 | 0 |
| Patient 1 | 1 | 183 |
| Patient 2 | 1 | 9 |
| Patient 3 | 1 | 7 |
| Patient 4 | 1 | 3 |
| Patient 5 | 1 | 14 |
| Patient 6 | 1 | 6 |
| Patient 7 | 1 | 4 |
| Patient 8 | 1 | 0 |
| Patient 9 | 1 | 0 |
| Patient 10 | 1 | 27 |
| Patient 11 | 1 | 44 |
| Patient 12 | 1 | 5 |
| Patient 13 | 1 | 7 |
| Patient 14 | 1 | 8 |
| Patient 15 | 1 | 2 |
| Patient 16 | 1 | 10 |
| Patient 17 | 1 | 872 |
| Patient 18 | 1 | 2 |
| Patient 19 | 1 | 5 |
| Patient 20 | 1 | 12 |
| Patient 21 | 1 | 22 |
| Patient 22 | 1 | 2 |
| Patient 23 | 1 | 0 |
| Patient 24 | 1 | 14 |
| Patient 25 | 1 | 0 |
| Patient 26 | 1 | 7 |

Figure 26:
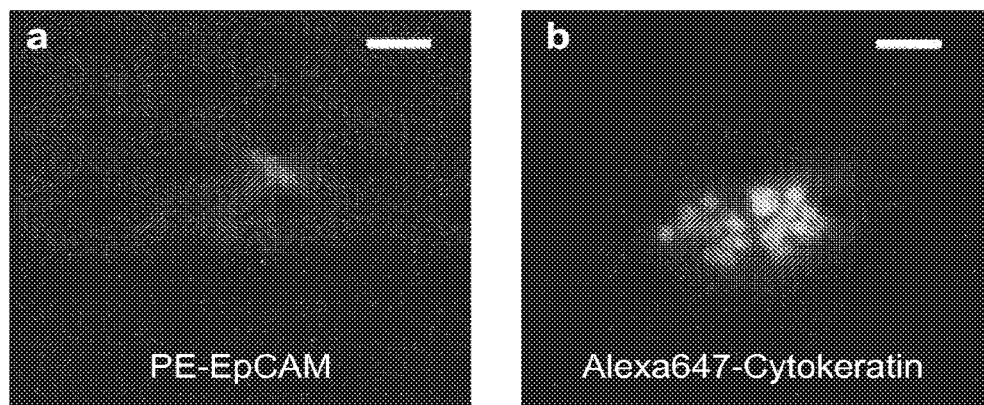
FIG. 26 shows a CTC cluster with low epithelial cell-adhesion marker (EpCAM) expression from a pancreatic cancer sample according to an aspect of the present disclosure.

With this method, CTCs were detected in 80% (8 of 10) of the samples ranging from 2 to 872 cells/mL. CTC clusters, reported by previous studies, were also observed in the patient blood samples. It is interesting to point out that many of the clusters observed in experiments had low EpCAM expression. FIG. 26 shows a cluster of CTCs which had a high expression of cytokeratin but a low expression of EpCAM.

Example 2

Imaging Multiple Biomarkers in Captured Rare Cells by Sequential Immunostaining and Photobleaching In this example, a preferred scheme for the sequential immunostaining and photobleaching process is disclosed. In a preferred example, an inline staining and washing system are coupled with eDAR in order to minimize the dead volume; decrease the amount of antibodies used; avoid introducing air bubbles; and automate the process.

This example describes an optimized, simple and semi-automatic method to perform expression analysis of protein markers on trapped CTCs. An inline immunostaining and photobleaching system can allow for labeling and fluorescence imaging on selected CTCs. The method can include, labeling CTCs with a group of antibodies conjugated to different fluorophores followed by photobleaching and re-labeling with different fluorescent antibodies against another group of biomarkers. This process can be repeated multiple times to study several groups of protein biomarkers. In an exemplary case, two protein markers of interest can be combined with a positive control marker (e.g., nuclear stain) and a negative control marker (e.g., CD45) to create a group. One group can be studied in each round, followed by photobleaching before a second round (e.g., four rounds of immunostaining and photobleaching) to look at the expression of protein markers of interest.

Microfluidic Components and Line-Confocal Optics

The polydimethylsiloxane (PDMS) microfluidic chips were fabricated using methods described previously. Briefly, the features were designed using AutoCAD (AutoDesk, San Rafael, CA), and then written on a transparency mask by Fineline Imaging (Colorado Springs, CO). Micro-features were fabricated on a silicon wafer using SU-8-3050 (Micro-Chem Corp., Newton, MA) as a negative photoresist; the feature height was controlled to be 50 μm. Once the features were developed, uncured PDMS was poured onto the silicon master, incubated at 75° C. for 2 hours, peeled off and then bonded to a glass coverslip using the plasma oxidation method.

The line-confocal detection scheme used two laser sources, 488 and 633 nm, to form the two detection windows using a series of dichroic mirrors, cylindrical lens and beam splitters. The first detection window, having the two laser beams overlapped at the same time, was used to detect the fluorescence signals from the labeled CTCs, and then controlled the sorting automatically. The second detection window was used to confirm the sorted aliquots and monitor the sorting efficiency.

Biological Materials and eDAR Process

Isoton (Beckman Coulter Inc., Chino, CA) was used as the buffer for all the experiments unless otherwise specified. The breast cancer cell lines MCF-7, SKBr-3 and MDA-MB-231 (American Type Culture Collection (ATCC), Manassas, VA) were used to characterize the system. Cell culture was performed under the conditions recommended by the vendor, and harvested once a week. MCF-7 was cultured in Eagle's Minimum Essential Medium (EMEM); SKBr-3 cells were cultured in McCoy's 5; and MDA-MB-231 was cultured Dulbecco's Modified Eagle's Medium (DMEM) (ATCC, Manassas, VA). All media also contained 2 mM L-glutamine, 10% fetal bovine serum (FBS) (ATCC, Manassas, VA), and 50 µg/mL penicillin/streptomycin. Human whole blood drawn from healthy donors was purchased from Plasma Lab International (Everett, WA) and stored at 4° C. upon arrival. Each 20 mL draw came in four 5 mL Vacutainer tubes coated with EDTA as an anti-coagulant. The first tube of each draw was discarded to avoid potential contamination from skin cells.

Antibodies were centrifuged for 5 minutes at 14,000 rpm to remove possible aggregates before any labeling procedure. Each blood sample was labeled with anti-epithelial cell adhesion molecule (EpCAM) conjugated with phycoerythrin (PE) (Abnova, Taipei City, Taiwan) in darkness and incubated at room temperature for 30 min. The labeled blood sample was washed and centrifuged (2,300 rpm for 10 min) to remove the free antibodies. The sample was immediately injected into the microfluidic chip using a syringe pump. Typically, the flow rate was set to 50 µL/min for the operation of eDAR, although based on the previous optimization methods, it can be higher. APD signal traces were collected by a PCI data acquisition card (PCI 6602, National Instruments, Austin, TX) and analyzed by a MATLAB (MathWorks, Natick, MA) script developed in-house. A home-built electronic box was programmed to give an automatic feedback control based on the detected APD signals, and apply a voltage on the solenoid (S-10-38-H-40, Magnetic sensor systems, Van Nuys, CA) connected to the microfluidic chip. More details about eDAR were described previously.

Sequential Immunostaining and Photobleaching Process

After washing the cells isolated by eDAR, main, side and waste channels were closed by turning off the inline valve. A 400-µL aliquot of cell fixation buffer (BioLegend, San Diego, CA) was introduced into the microfluidic chip by a peristaltic pump (Fisher Scientific, Pittsburgh, PA) at a flow rate of 15 µL/min. After washing with the buffer for 5 minutes at the same flow rate, the cells were permeablized by flowing through 250 µL of 2.5% surfynol 465 surfactant (Air Products and Chemicals Inc, Allentown, PA) for 15 min. After this step, four rounds of immunostaining and photobleaching of the cells were performed. For each round of staining, 220 µL of a staining solution with four biomarkers conjugated to four different fluorescent dyes were prepared. The details about the antibodies and nuclear stain used in each round are summarized in Table 2. After a centrifugation step (14,000 rpm for 5 min) to remove the aggregates, 200 µL of the supernatant was collected as the staining buffer. The supernatant was injected into the microfluidic chip at a flow rate of 20 µL/min. When the antibody solution filled the whole filtration area, the flow was stopped. Incubation took place for 20 minutes in dark to ensure all the trapped cells came into contact with the antibodies efficiently. After this step, the cells were washed for 10 minutes to remove any free antibodies and minimize the fluorescence background. Photobleaching was performed using a xenon arc lamp as the light source (Sutter instrument, Novato, CA). Each bleaching step took 15 min. A 20× objective was used for epi-fluorescence imaging and photobleaching. Fluorescence images were collected before and after the photobleaching step from 4 different emission channels: yellow (555 to 605 nm for PE), blue (435 to 485 nm for Hoechst), green (510 to 540 nm for FITC or Alexa 488) and red (665 to 695 nm for Alexa 647 or APC).

Safety Consideration for the Photobleaching Process

To ensure safety when running the photobleaching tests, the highest power was locked to 10 mW. Certain protective methods should be considered when the sample is exposed to the light source, such as wearing protective goggles or covering the photobleaching area with a black box.

CTCs Isolated by eDAR

Whole blood sample was pre-labeled with the antibodies conjugated to fluorophores and then introduced to the microfluidic chip. In many applications, EpCAM was used as the biomarker for the positive selection. However, the method can be flexible in using a different or more complicated selection logic.

In eDAR, a virtual aliquot was first defined by a combination of the laser detection beam, the volumetric flow rate, and the sorting speed. Based on these factors, the labeled blood sample was virtually divided up into half a million aliquots per 1 mL with 2 nL per an aliquot. The line-confocal detection method detected the fluorescence emission with single-analyte sensitivity. As a result, these virtual aliquots were ranked based on the primary labeling schemes as "positive" or "negative." Because of the very low concentration of CTCs, more than 99.999% of the aliquots were discarded (FIG. 10A), which resulted in a greater than 1-million-fold enrichment ratio.

Based on the results of the aliquot ranking, an automatic feedback mechanism was applied to trigger a hydrodynamic switch of the blood flow so that the "positive" aliquots could be collected and transferred to an area for further purification (e.g., purification chamber) and analysis. Two design elements controlled this hydrodynamic switch—a solenoid and the pressure drop in the two side buffer lines. A solenoid was placed in the CTC collection channel in the closed position on the left (FIG. 4A) so the "negative" aliquots only flowed into the waste channel on the right. There was also a pressure drop between the two side channels where the buffer flowed, which switched the blood flow from the waste channel to the collection side when the solenoid was open. This simple scheme was fast enough at 2 to 3 milliseconds to collect CTCs with minimum amount of blood cells. A second line-confocal detection window was also placed on the collection side to monitor the efficiency of the hydrodynamic switching in real time. FIG. 4B shows a small part of the data from a sample taken from a lung cancer patient. In this figure, the green signal shows the APD traces from the first detection area which controlled the aliquot sorting;

the signal in red was the APD counts from the second detection area confirming that the aliquots were actually sorted.

These sorted aliquots were transferred to an area where CTCs could be trapped and most of the blood cells discarded (FIG. 4A). Although there are many possible ways to further purify the captured cells, a small piece of polycarbonate filter (5×5 μm pore size) was incorporated onto the microfluidic chip. The trapped cells were imaged and further labeled with more biomarkers on the microfluidic chip to determine their identities. For example, FIG. 26a and FIG. 26b shows a cancer cell trapped on the microfluidic chip, which was positive against EpCAM, cytokeratin, and the nuclear stain but negative against CD45. This cell was also observed by bright-field microscopy, which provided the morphological information.

Sequential Immunostaining and Photobleaching

An inline staining and washing system was developed and coupled with eDAR in order to minimize the dead volume; decrease the amount of antibodies used; avoid introducing air bubbles; and automate the process. As shown in FIG. 13A, two ports on the microfluidic chip were left open to perform the perfusion labeling and washing steps while all the other three ports were completely closed. A peristaltic pump delivered the washing buffer and labeling reagents to the microfluidic chip and was coupled with the pressurized buffer source via a six-way valve. The other three ports on this valve were completely blocked to prevent any possible leakage or contamination. When running the eDAR experiment, the six-way valve was turned to the pressurized buffer side to provide a stable control of the hydrodynamic switching. It was turned to the peristaltic-pump side to inject accurate amounts of reagents to the microfluidic chip without introducing any air bubbles. Using this scheme, a few nanograms of the antibodies were introduced to the trapped cells in less than 5 min; a typical incubation step took less than 20 minutes (FIG. 13B).

If there was a need to perform intracellular marker testing, the captured cells were fixed and permeabilized on the microfluidic chip prior to the test. Then multiple rounds of the staining, washing, imaging and bleaching experiments were performed sequentially. In each round, four colors of fluorescence, i.e., yellow (PE), red (Alexa 647 or APC), green (FITC), and blue (nuclear stain), were monitored.

For this part of the study, an assay for the expression of protein markers on captured CTCs based on four rounds of sequential immunostaining and photobleaching processes was designed. Four different makers in each round through four individual channels using epi-fluorenscence microscopy were monitored. Each set of markers had a nuclear stain (Hoechst) as a positive control marker, CD45 conjugated with FITC as a negative control marker, and two protein markers conjugated with PE or Alexa 647. The system was designed not to bleach the Hoechst stain for two reasons: the stain was used as a positive control marker, and it would require a UV exposure to bleach the stain, which could cause significant cellular damage. CD45 is widely expressed on many types of white blood cells (WBCs), which are considered to be the biggest interferences in the separation of CTCs. Therefore, they are frequently used as negative control markers.

Many protein markers can be tested on CTCs but as a proof of concept, eight antigens were selected and divided them into four groups (Table 2). The first set had EpCAM and cytokeratin, which are the most widely used markers to identify CTCs. The immunostaining test set was applied right after the capture of CTCs by eDAR to further confirm and enumerate the CTCs with epithelial biomarkers. Table 2 shows that there were six tumor cells trapped on the microfluidic chip, which are positive to the Hoechst stain but negative to CD45. Two of them had a strong expression of EpCAM and cytokeratin, which implied the cells had epithelial characteristics.

The second set was designed to investigate other epithelial markers which are important for clinical and biological studies. Her2 and MUC1 were selected as the two protein markers for this set since these two biomarkers play important roles in the cancer pathogenesis and resistance to drugs. They are also potential targets of the anti-tumor drugs and immunotherapy. The second round of labeling in FIG. 14 shows that part of the cells trapped on the microfluidic chip had MUC1 expression but all of them were really low in their Her2 expression.

Cancer stem cells have been shown to play important roles in tumor progression and have been observed in the population of CTCs. The third set of markers had two cancer stem cell antigens, CD44 and CD24. They are extensively studied as stem cell markers for breast cancer and possibly for other types of cancers as well. The data in Table 2 shows that 4 cells had a strong expression of CD44+/CD24−, and the other two are CD44−/CD24+. Other stem cell markers, such as CD133 and CD105, can also be used in this group based on the type of primary cancer.

The last set of markers in Table 2 was designed to look at the expression of EGFR and CD166 to demonstrate the mesenchymal characteristics of tumor cells. EGFR has been shown to be associated with the EMT process, and CD166 was used to define mesenchymal stem cells in bone marrow. Other related markers, such as vimentin and cadherin, can be used in this group as well.

Characterization of Photobleaching

There are two critical factors that can determine the efficiency of the photobleaching step—exposure power and time which were characterized and optimized them to improve the efficiency and throughput while ensuring that the cells were not damaged by potential heating. The photobleaching curve under different exposure powers was studied first (FIG. 15A). MCF-7 cells were labeled with anti-EpCAM-PE, and placed on a No. 2 coverslip. Labeled single cells were bleached with three different power settings. The bleaching curves show that the exposure time can be controlled under 10 minutes to get a more than 95% bleaching efficiency when the exposure power was higher than 2 mW.

Based on this, any of the bleaching curves of the four fluorophores, PE, FITC, Alexa 488 and Alexa 647, can be directly applied in the scheme. FIG. 15B shows that the fluorescent emission of PE, FITC and Alexa 488 can be bleached to less than 10% in less than 5 min; the photobleaching times for Alexa 647 took longer, partly because the power of the light source between 610 to 660 nm (red excitation) was lower than that in the range of yellow and green excitation. As a result, the bleaching time was set to 15 minutes to get a high bleaching efficiency with an acceptable throughput. This can be improved by raising the power of the light source, although this may potentially increase the risk of heating and cellular damage.

Example 3

Single-Analyte Trapping for Sequential Immunostaining and Imaging

This example describes a single-analyte trapping apparatus coupled with the method of sequential immunostaining and imaging.

The relevant dimensions involved in an effective serial-flow resistance trap design, as well as a schematic of a device having arbitrary trapping density and dimensions (FIG. 17), with an inset showing a magnified region are depicted in FIG. 18. The schematic in FIG. 18A shows the relative dimensions of the device, such as the width of the main channel, the width of the constriction, the length from the main channel constriction entrance to the main channel constriction exit, the length across the constriction, as well as the heights of the main channel, the constriction, and the constriction chamber. FIG. 18C shows an exemplary microfluidic device design that utilizes the serial-flow resistance trap. The design comprises an inlet where sample is introduced (left side) and an outlet where excess liquid phases are removed (right side). The center of the device design depicts the high density of flow resistance traps that is incorporated. FIG. 18B shows a magnified region of FIG. 18C and shows the flow resistance traps that constitute the functional part of the device.

FIG. 19 depicts a parallel flow resistance trap. Top panels of FIG. 19 depict three-dimensional cross-sectional side views of wells from the device showing shape variations in the well and constrictions. The well design can be in differing or similar combinations of shapes such as cylinder, cone, square, hexagon, dome, etc. Dimensions of the well can be defined by $h_1$=depth of well, $h_2$=depth of constriction, $r_1$=radius of well, and $r_2$=radius of constriction. According to this aspect, the device is capable of trapping single particles/cells from a solution such as beads, cells, etc. Multiple wells can be arranged in parallel to form the device.

FIG. 20 is a schematic depiction of a procedure that is used to build some of the devices described herein this disclosure. In this process, a solid substrate (e.g., silicon wafer) is spin-coated with photoresist. The coated substrate is placed in hard contact with a photolithographic mask imprinted with the desired design depicted in UV-transparent and opaque regions. The mask and substrate are exposed to UV-light, which initiates photochemical crosslinking reactions in the photoresist. The first layer of the fabricated device is completed by developing the resultant crosslinked pattern, dissolving away the non-crosslinked portion of the photoresist. The second layer of the fabrication proceeds by coating, exposing, and developing a second layer of photoresist. The result is a mold used for forming channel, chamber, and well structures in a curable material (e.g., PDMS) or embossable material. For example, the mold is placed into a dish. Second, PDMS is poured over the mold and cured. Third, the PDMS is released (peeled) from the mold, and at this point inlets and outlets are punched (not depicted). Finally, the patterned PDMS is sealed to a flat glass or PDMS piece to enclose the channels and chambers/wells.

FIG. 21 shows an example of a microfabrication method that is used to produce a parallel flow resistance trap. The device is fabricated in material other than photoresist (e.g., SU-8) as described above. Available materials can include but are not limited to polymeric material, photoresist, polymethydisoloxane (PDMS), polymethylmethacrylate (PMMA), polymethylurethane (PUMA), etc. (1) A sacrificial layer can be spin-coated on silicon (Si) wafer. (2) Photoresist (SU-8) can be deposited on top. (3) A photomask with the microarray pattern is aligned, and the wafer is exposed to UV. (4) Uncrosslinked photoresist is processed and removed leaving the desired pattern on the silicon wafer. A 2-layer design is used in one aspect. In that case, a second layer of photoresist is spin-coated and processed. (5) The SU-8 layer is released from the Si wafer and is assembled onto (path 1 only) a porous polycarbonate filter and/or (path 1-2) PDMS mount with a single outlet for inserting tubing.

Figure 22:
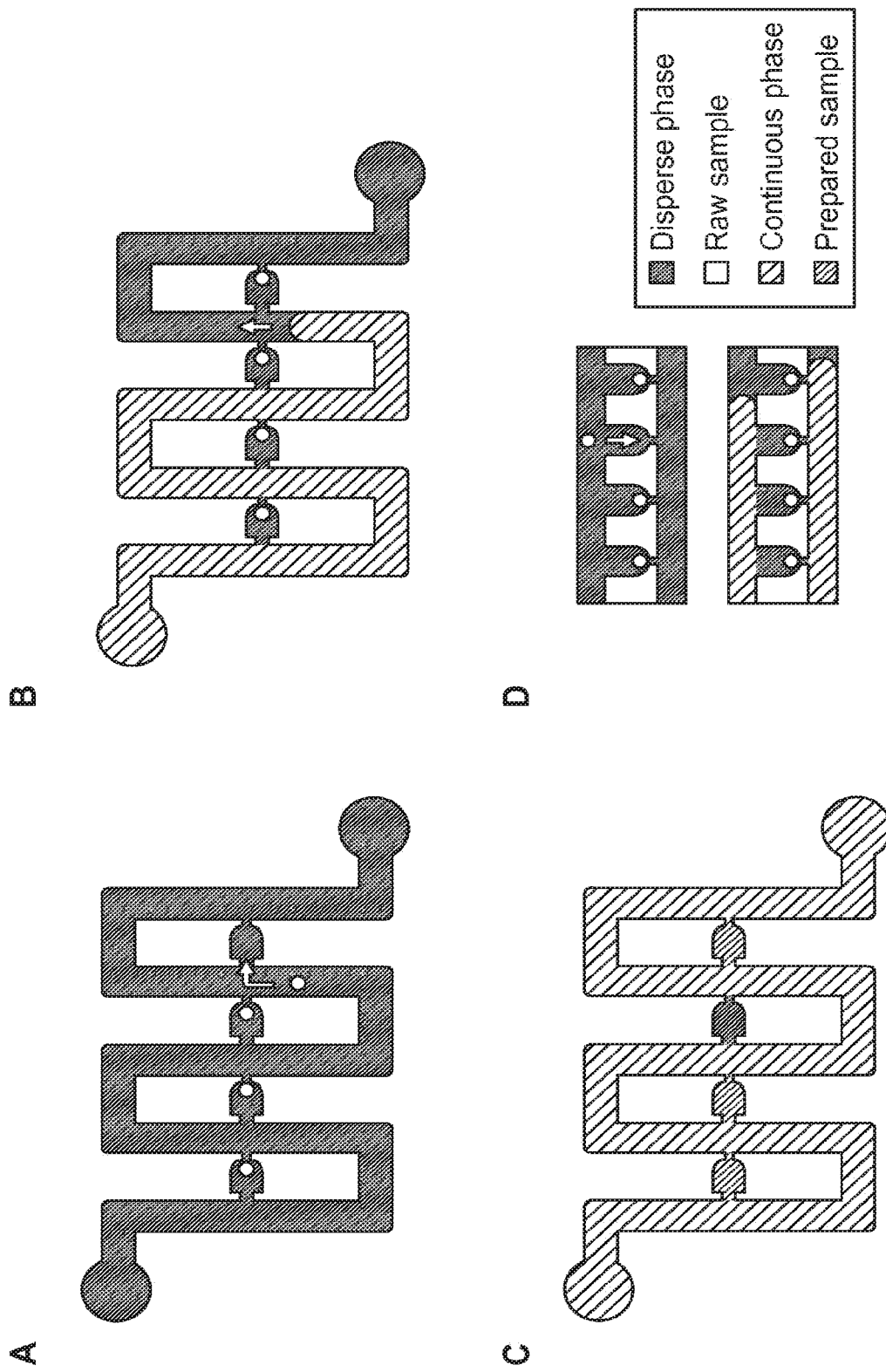
FIG. 22 depicts the steps by which the serial-flow resistance trap and parallel flow resistance trap can collect, discretize, and read out biologically derived samples according to an aspect of the present disclosure.

FIG. 22 depicts a set of steps by which the serial-flow resistance trap and parallel flow resistance trap function to collect, discretize, and readout biologically derived samples. Part A shows how samples serially fill the defined locations. This process occurs when the critical dimension (diameter) of the sample is smaller than the height and width of the main channel, as well as larger than the height or width of the constriction. Differential resistance to flow steers the sample into the defined region, whereupon the constriction is occluded and flow is stopped. Subsequent samples follow a flow path through the main channel, to the next trapping location, until all traps are filled. Part B shows how an immiscible liquid phase is introduced through the sample inlet, and serially discretizes the trapped samples. The immiscible liquid will not flow into the sample regions because of lack of fluid flow due to the occluded restriction, as well as by an interfacial barrier that is created by the differential contact angles of the immiscible phases with the channel material and the dimensions of the trapping region. Part C demonstrates how varied chemical natures of the discretized samples are detected. As a consequence of the serial nature of filling, temporal information regarding each sample is also physically encoded in each location. Part D illustrates the first step of samples filling the parallel flow resistance trap. Sample particles follow flow from the top of the device into the defined trapping wells. Due to the parallel nature of the design, multiple samples are trapped simultaneously for faster sample collection than certain other trapping schemes presented herein. Part E shows how an immiscible phase is replaced both above and below the plane of the trapping wells, thereby generating the discretized samples. Part F displays how samples of varying chemical nature are detected simultaneously.

Figure 23:
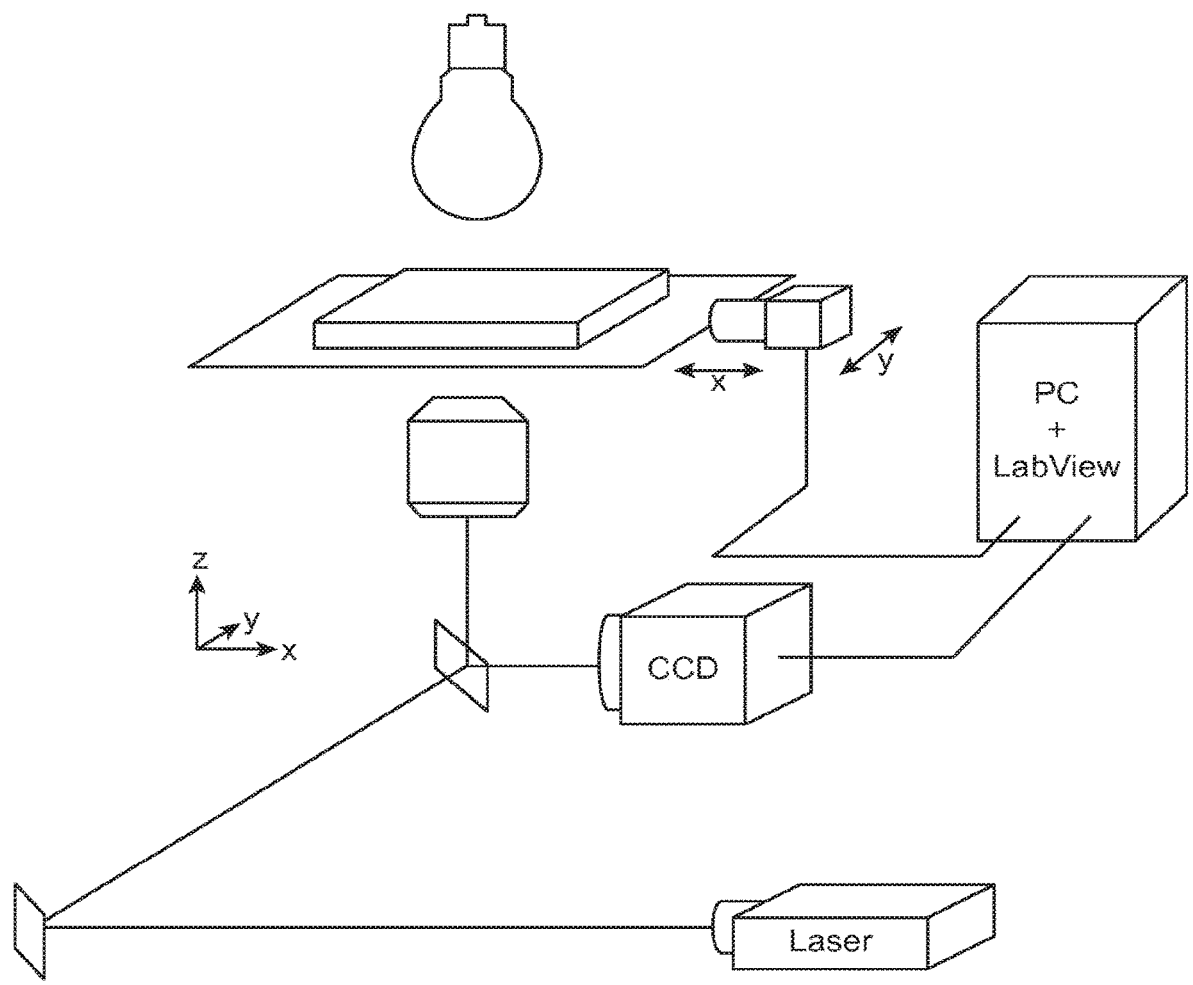
FIG. 23 shows a detection and read-out scheme for arrays of micro-wells and side chambers based on brightfield and fluorescence microscopy according to an aspect of the present disclosure.

FIG. 23 shows a detection and read-out scheme for arrays of micro-wells and side chambers based on brightfield microscopy and fluorescence microscopy. The sample is placed on an automated translation stage controlled by computer programs. Images are acquired by high speed CCD cameras.

FIG. 24 illustrates the sequence for trapping an array of biological particle/cell for analysis and release. (1) Flow is applied from the tubing to facilitate fluid flow through the trap. Free standing particles/cells in the fluid follow the flow pattern into the open well. (2) Once trapped, flow ceases in that localized region. (3) Solution is used to rinse off excess fluid and particles/cells. The device allows for the following analysis to be performed on the particle/cell, such as repeated cycle of fluorescence imaging, bleaching, and analysis. Upon completion of analysis, (4) flow in the tubing is reversed to release the particle.

Example 4

Dual Capture eDAR

This example describes a "dual-capture" version of eDAR according to an aspect of the present disclosure. The dual-capture eDAR can separate two different subpopulations of CTCs from the same human blood sample on the same microfluidic device simultaneously. Those two subpopulations can be trapped separately on two different regions on the microfluidic chip, with a high recovery and purity, respectively.

FIG. 11 shows the general structure of the microfluidic device. Blood samples were pre-labeled with two kinds of antibodies conjugated with different fluorescent tags. For example, the blood sample was labeled with an epithelial marker, such as anti-EpCAM conjugated with PE, as well as a mesenchymal marker, such as anti-EGFR or anti-vimentin conjugated with another fluorophore having a different wavelength of emission compared to PE, such as FITC. The labeled blood sample was injected into the microfluidic chip, the CTCs with EpCAM expression could be detected using the line-confocal scheme with a peak in the yellow channel, and then an active sorting event was triggered to collect that aliquot into the collection channel #1. Similarly, if the aliquot was ranked as positive to the mesenchymal markers, it was sorted to the collection channel #2. The two subpopulations were then trapped and enriched on the microfluidic chip separately. The filtration area was built on the same design of microslits used in the second generation of eDAR.

The fluidic switching scheme is summarized as follows. When the aliquots were ranked as negative to any marker applied, then both of the solenoids in FIG. 11 were closed. If the pressure on the two side channels was balanced, the blood flowed to the bottom center channel, which was used to collect the waste. When the aliquots were ranked as positive to epithelial marker only, solenoid #2 opened immediately so the blood flow was pushed to the collection channel on the left (FIG. 12B). After the aliquot was collected, solenoid #2 closed again, so the blood flow switched back to the center. When the aliquots were ranked as positive to epithelial marker only, solenoid #1 opened immediately so the blood flow was pushed to the right side (FIG. 12C). The response time for the two types of eDAR sorting events was about 2 to 3 milliseconds.

FIG. 11 shows the general structure of the "dual-capture" eDAR. Labeled blood was introduced into the main channel on the top. Buffer was flowing in the two side channels to control the hydrodynamic switching of the blood flow using two solenoids. Two subpopulations of CTCs were separated and trapped on two different filtration areas on the same microfluidic chip.

FIG. 12 depicts bright field images of the three status of the blood flow. A) The blood flowed into the waste collection channel, because the aliquots were ranked as negative to either markers. B) The blood was switched to the collection channel #1, and the first subpopulation of CTCs transferred to there. C) The blood was switched to the collection channel #2, and the second subpopulation of CTCs transferred there.

ADDITIONAL ASPECTS

Described herein are methods and apparatuses for analyzing particles, particularly particles in aliquots of a fluid sample wherein the particles are analytes and the analytes are cells, in order to (1) identify a plurality of markers present on an analyte within a fluid, particularly by using a tag for at least each marker on the analyte and detecting the signal emitted by each tag prior to removing the signal emitted by each tag and repeating the process of detecting and reducing the signal, (2) isolate cells from a sample comprising a mixture of first and second subtypes of cells, particularly by introducing the sample into a microfluidic chip comprising at least one channel fluidly connected to the set of tubing and to at least one chamber, (3) partition cells expressing a specific biomarker profile from a fluid sample, particularly using an apparatus that comprises a set of tubing connected to a microfluidic chip that has at least one channel, (4) identify a plurality of markers present on an analyte, particularly by partitioning a plurality of analytes using a substrate comprising a plurality of micro-cavities or micro-patches so as to contain no more than one analyte in each micro-cavity or micro-patch, (5) detect a particle in a fluid sample, particularly using a microfluidic chip with at least one sample input channel, at least one directional flow channel, and at least two output channels, and an electro-actuated valve that is located on a device that is not part of the microfluidic chip, (6) isolate an aliquot of a fluid sample within a microfluidic chip, particularly by assigning a value to the aliquot based on the presence or absence of the rare particle and directing the flow of the aliquot based on the assigned value by opening an electro-actuated valve located on a device that is external to the microfluidic chip; and (7) detect a rare particle in a fluid sample using a device with at least two output channels, particularly with at least one of the two output channels is fluidly connected with an array of micro-apertures, and using the device to sort the one or more rare particles.

In some aspects, this disclosure provides methods for identifying a plurality of markers present on an analyte within a fluid, wherein the method comprises: (a) detecting a signal from a first tag using a source of radiation, wherein the first tag is attached to a first structure that binds to a first marker on the analyte; (b) partitioning the analyte based on the presence of the first tag; reducing the level of the signal of the first tag; (c) contacting the analyte with a second structure that binds to a second marker, wherein the second structure is attached to a second tag; and (d) detecting the second tag. In some embodiments of these aspects, the signal of the first tag is reduced by greater than 50%. In some aspects, the partitioning of step (a) is based on the presence of the first tag and a third tag. In some aspects, the partitioning of step (a) is performed with a microfluidic device. In some aspects, the partitioning of step (a) and the detecting in step (b) occurs within the same microfluidic device. In some aspects, the analyte is a cell. In some aspects, the cell is a cancerous cell. In some aspects, the cancerous cell is a rare cell. In some aspects, the analyte is a circulating tumor cell. In some aspects, the cell is an immune cell, a fetal cell, a cell indicative of a disease remaining after treatment, or a stem cell. In some aspects, the fluid is selected from the group consisting of: whole blood, fractionated blood, serum, plasma, sweat, tears, ear flow, sputum, lymph, bone marrow suspension, lymph, urine, saliva, semen, vaginal flow, feces, transcervical lavage, cerebrospinal fluid, brain fluid, ascites, breast milk, vitreous humor, aqueous humor, sebum, endolymph, peritoneal fluid, pleural fluid, cerumen, epicardial fluid, and secretions of the respiratory, intestinal and genitourinary tracts. In some aspects, the fluid is whole blood. In some aspects, the fluid is fractionated whole blood. In some aspects, the first tag is an antibody. In some aspects, the first tag is a fluorophore. In some aspects, the first tag is a probe comprised of a nucleic acid. In some aspects, the reduction of the signal in step (c) is accomplished by applying radiation to the analyte. In some aspects, the radiation is white light. In some aspects, the reduction of the signal in step (c) is accomplished by applying a chemical to the first tag. In some aspects, the chemical is a reducing agent. In some aspects, the reducing agent is dithiothreitol. In some aspects, the radiation is applied using a laser. In some aspects, the radiation is applied using a light emitting diode (LED).

In some aspects, the method may further comprise imaging the signal from the first tag and the second tag. In some aspects, the analyte is present in a fluid, and the fluid is an aliquot of a larger volume of fluid. In some aspects, the partitioning is performed semi-automatically or automatically. In some aspects, partitioning is performed by ensemble-decision aliquot ranking. The In some aspects, each marker is a biomarker. In some aspects, the plurality of biomarkers is characterized by an expression profile.

In some aspects, the method further comprises contacting the analyte with a buffer. In some aspects, the buffer contains a fixative. In some aspects, the buffer contains permeabilization agent. In some aspects, the buffer is a washing buffer. In some aspects, a flow cytometer is not used to partition the analyte. In some aspects, at the time of the detecting in step a, the analyte is not a cell that is connected to additional cells within a tissue.

Described herein are methods and compositions for isolating cells from a cellular sample, in some aspects, the method of isolating cells from a cellular sample may comprise a first cell subtype and a second cell subtype that may further comprise, (a) introducing the sample into a microfluidic chip via a set of tubing wherein the microfluidic chip comprises, (i) at least one channel fluidly connected to the set of tubing; (ii) a detector configured to detect signals of cells within the at least one channel; and (iii) at least one chamber fluidly connected to the at least one channel; (b) flowing a portion of the cellular sample past the detector; (c) using the detector to detect the presence or absence of the first cell subtype within the portion of the cellular sample; (d) if the first cell subtype is detected within the portion of the cellular sample, directing an aliquot of the cellular sample into the chamber, wherein the aliquot comprises the first cell subtype; and, (e) repeating steps (b)-(d), thereby isolating multiple aliquots in the chamber such that the chamber comprises greater than 80% of a total number of first cell subtypes within the sample and less than 5% of a total number of second cell subtypes within the sample.

In some aspects, provided herein are apparatuses for partitioning cells expressing a specific biomarker profile from a sample derived from a fluid, wherein: the apparatus comprises a set of tubing connected to a microfluidic chip that has at least one channel and a chamber; and the apparatus is capable of isolating the cells in the chamber, wherein, after isolation, the chamber comprises greater than 80% of the total population of cells in the sample expressing the specific biomarker profile and wherein, after isolation, the chamber comprises less than 5% of the total population of cells in the sample expressing a different biomarker profile. In some aspects, the isolation of the cells expressing a specific biomarker profile occurs in less than 20 minutes. In some aspects, the specific biomarker profile is present on less than 5% of the cells in the sample of fluid. In some aspects, the fluid is blood. In some aspects, the fluid is fractionated whole blood. In some aspects, the fluid is the nucleated cell fraction of whole blood.

In some aspects, provided herein are methods for identifying a plurality of markers present on an analyte, wherein the method comprises: (a) partitioning a plurality of analytes by flowing the analytes over a substrate comprising a plurality of micro-cavities or micro-patches, wherein the majority of micro-cavities or micro-patches are capable of containing not more than one analyte and wherein the micro-cavities or micro-patches are located in a microfluidic device; (b) in the micro-cavities or micro-patches, contacting each analyte with a first structure that is capable of binding to a first marker, wherein the first structure is connected to a first tag; (c) detecting a signal from the first tag; reducing the level of the signal of the first tag; (d) contacting the analyte with a second structure that binds to a second marker, wherein the second structure is connected to a second tag; and (e) detecting the second tag. In some aspects, the signal of the first tag is reduced by greater than 50%. In some aspects, the contacting of step b is achieved by flowing a fluid comprising the first structure through a channel that is in fluid communication with the micro-cavities or micro-patch. In some aspects, following the contacting step of step (b), the method further comprises: contacting the analyte with a wash buffer. In some aspects, the analytes are cells. In some aspects, the analytes are held in a fixed position within the micro-cavities by a force generated by fluid flow, gravity, or adhesive forces. In some aspects, each analyte is connected to a micro-cavity or micro-patch through a molecular interaction. In some aspects, each analyte is connected to a micro-cavity through a non-covalent bond. In some aspects, the non-covalent bond is a van der Waals interaction, electrostatic bond, hydrophobic bond or non-specific adsorption.

In some aspects, provided herein are devices for detecting a particle in a fluid sample, the device comprising: a microfluidic chip comprising at least one sample input channel, at least one directional flow channel, and at least two output channels, wherein the at least one directional flow channel intersects the sample input channel; an electro-actuated valve that is located on a device that is not part of the microfluidic chip, wherein the electro-actuated valve controls the flow of a liquid by controlling an input channel that intersects at least one directional flow channel or at least one of the at least two output channels; at least one detector capable of detecting one or more analytes in an aliquot of the fluid sample; and a digital processor capable of assigning a value to the aliquot based on the presence, absence, identity, composition, or quantity of analytes in the aliquot, wherein the digital processor is in communication with the detector and the electro-actuated valve. In some aspects, the electro-actuated valve is a solenoid valve. In some aspects, the electro-actuated valve controls the flow of the liquid in at least one directional flow channel. In some aspects, the electro-actuated valve is normally closed and wherein the electro-activated valve opens after receiving a signal from the computer. In some aspects, the electro-actuated valve is normally open and wherein the electro-activated valve closes after receiving a signal from the computer. In some aspects, the at least one directional flow channel comprises at least two ports and wherein the electro-actuated valve controls the flow of fluid through one of the ports. In some aspects, the device comprises a second detector. In some aspects, at least one of the output channels is fluidly connected to a filter. In some aspects, the electro-actuated valve directly controls the flow of a liquid in at least one directional flow channel. In some aspects, the electro-actuated valve directly controls the flow of a liquid in a channel that feeds into at least one directional flow channel. In some aspects, the electro-actuated valve directly controls the flow of a liquid in only one directional flow channel. In some aspects, the electro-actuated valve directly controls the flow of a liquid in one of the at least two output channels. In some aspects, the electro-actuated valve directly controls the flow of a liquid in a channel that feeds into one of the at least two output channels. In some aspects, the at least one directional flow channel intersects the at least two output channels at one or more junctions. In some aspects, the device comprises a detector. In some aspects, the device comprises a confirmatory laser. In some aspects, the detector is located on at least one channel that is not an output channel. In some aspects, the confirmatory laser is located on at least one channel that is not an input channel. In some aspects, the electro-actuated valve is a piezo-electric valve.

In some aspects, provided herein are methods for isolating an aliquot of a fluid sample within a microfluidic chip, wherein the aliquot comprises a rare particle, the method comprising the steps of: detecting the presence or absence of the rare particle in the aliquot; assigning a value to the aliquot based on the presence or absence of the rare particle; and directing the flow of the aliquot based on the assigned value by opening an electro-actuated valve, wherein the electro-actuated valve is located on a device that is external to the microfluidic chip. In some aspects, the microfluidic chip comprises a sample input channel, at least two output channels, and at least one directional flow channel, and wherein the electro-actuated valve controls the flow of fluid within the directional flow channel.

In some aspects, provided herein are devices for detecting a rare particle in a fluid sample, the device comprising: at least a first sample input channel; at least two output channels, wherein at least one of the two output channels is fluidly connected with an array of micro-apertures; at least one detector capable of detecting one or more rare particles in an aliquot of the fluid sample; and a mechanism for sorting the one or more rare particles by directing the flow of aliquots containing the one or more rare particles through a first output channel. In some aspects, the mechanism directs the flow of the aliquots into a second output channel if the aliquot does not contain a rare particle. In some aspects, the array of apertures is disposed between the first sample input channel and the at least two output channels. In some aspects, the array of apertures is in the same plane as the first sample input channel and the output channels. In some aspects, the array of apertures is configured so that the rare particles cannot pass through the apertures but at least one other particle is capable of passing through the apertures. In some aspects, the array of apertures comprises greater than 1000 apertures. In some aspects, the mechanism for sorting the rare particles comprises an electrode, a magnetic element, an acoustic element, or an electro-actuated element. In some aspects, the detector is selected from the group consisting of a camera, an electron multiplier, a charge-coupled device (CCD) image sensor, a photomultiplier tube (PMT), an avalanche photodiode (APD), a single-photon avalanche diode (SPAD), a silicon photomultiplier (SiPM), and a complementary metal oxide semiconductor (CMOS) image sensor.

In various aspects, methods are provided for identifying a plurality of markers present on an analyte within a fluid, wherein the methods comprise: (a) detecting a signal from a first tag using a source of radiation, wherein the first tag is attached to a first structure that binds to a first marker on the analyte; (b) partitioning the analyte based on the presence of the first tag; (c) reducing the level of the signal of the first tag; (d) contacting the analyte with a second structure that binds to a second marker, wherein the second structure is attached to a second tag; and (e) detecting the second tag.

In some aspects, the signal of the first tag is reduced by greater than 50%. In other aspects, the partitioning of step (a) is based on the presence of the first tag and a third tag. In further aspects, the partitioning of step (a) is performed with a microfluidic device. In still further aspects, the partitioning of step (a) and the detecting in step (b) occurs within the same microfluidic device. In some aspects, the analyte is a cell. In other aspects, the cell is a cancerous cell. In further aspects, the cancerous cell is a rare cell. In still further aspects, the analyte is a circulating tumor cell. In some aspects, the cell is an immune cell, a fetal cell, a cell indicative of a disease remaining after treatment, or a stem cell. In other aspects, the fluid is selected from the group consisting of: whole blood, fractionated blood, serum, plasma, sweat, tears, ear flow, sputum, lymph, bone marrow suspension, lymph, urine, saliva, semen, vaginal flow, feces, transcervical lavage, cerebrospinal fluid, brain fluid, ascites, breast milk, vitreous humor, aqueous humor, sebum, endolympth, peritoneal fluid, pleural fluid, cerumen, epicardial fluid, and secretions of the respiratory, intestinal and genitourinary tracts. In some aspects, the fluid is whole blood. In further aspects, the fluid is fractionated whole blood. In still further aspects, the first tag is an antibody. In some aspects, the first tag is a fluorophore. In some aspects, the first tag is a probe comprised of a nucleic acid. In other aspects, the reduction of the signal in step (c) is accomplished by applying radiation to the analyte. In further aspects, the radiation is white light. In still further aspects, the reduction of the signal in step (c) is accomplished by applying a chemical to the first tag. In some aspects, the chemical is a reducing agent. In further aspects, the reducing agent is dithiothreitol. In some aspects, the radiation is applied using a laser. In other aspects, the radiation is applied using a light emitting diode (LED). In further aspects, the method further comprises imaging the signal from the first tag and the second tag. In still further aspects, the analyte is present in a fluid, and the fluid is an aliquot of a larger volume of fluid. In some aspects, the partitioning is performed semi-automatically or automatically. In other aspects, the partitioning is performed by ensemble-decision aliquot ranking. In some aspects, the each marker is a biomarker. In further aspects, the plurality of biomarkers is characterized by an expression profile. In still further aspects, the method further comprises contacting the analyte with a buffer. In some aspects, the buffer contains a fixative. In other aspects, the buffer contains permeabilization agent. In further aspects, the buffer is a washing buffer. In still further aspects, a flow cytometer is not used to partition the analyte. In some aspects, at the time of the detecting in step a, the analyte is not a cell that is connected to additional cells within a tissue.

In various aspects, methods are provided for isolating cells from a cellular sample comprising a first cell subtype and a second cell subtype comprising: (a) introducing the sample into a microfluidic chip via a set of tubing wherein the microfluidic chip comprises (i) at least one channel fluidly connected to the set of tubing; (ii) a detector configured to detect signals of cells within the at least one channel; and (iii) at least one chamber fluidly connected to the at least one channel; (b) flowing a portion of the cellular sample past the detector; (c) using the detector to detect the presence or absence of the first cell subtype within the portion of the cellular sample; (d) if the first cell subtype is detected within the portion of the cellular sample, directing an aliquot of the cellular sample into the chamber, wherein the aliquot comprises the first cell subtype; and (e) repeating steps (b), (c), and (d), thereby isolating multiple aliquots in the chamber such that the chamber comprises greater than 80% of a total number of first cell subtypes within the sample and less than 5% of a total number of second cell subtypes within the sample.

In various aspects, apparatuses are provided for partitioning cells expressing a specific biomarker profile from a sample derived from a fluid, wherein: (a) the apparatuses comprise a set of tubing connected to a microfluidic chip that has at least one channel and a chamber; and (b) the apparatuses are capable of isolating the cells in the chamber, wherein, after isolation, the chamber comprises greater than 80% of the total population of cells in the sample expressing the specific biomarker profile and wherein, after isolation, the chamber comprises less than 5% of the total population of cells in the sample expressing a different biomarker profile. In some aspects, the isolation of the cells expressing a specific biomarker profile occurs in less than 20 minutes.

In other aspects, the specific biomarker profile is present on less than 5% of the cells in the sample of fluid. In further aspects, the fluid is blood. In still further aspects, the fluid is fractionated whole blood. In some aspects, the fluid is the nucleated cell fraction of whole blood.

In various aspects, methods are provided for identifying a plurality of markers present on an analyte, wherein the methods comprise: (a) partitioning a plurality of analytes by flowing the analytes over a substrate comprising a plurality of micro-cavities or micro-patches, wherein the majority of micro-cavities or micro-patches are capable of containing not more than one analyte and wherein the micro-cavities or micro-patches are located in a microfluidic device; (b) in the micro-cavities or micro-patches, contacting each analyte with a first structure that is capable of binding to a first marker, wherein the first structure is connected to a first tag; (c) detecting a signal from the first tag; (d) reducing the level of the signal of the first tag; (e) contacting the analyte with a second structure that binds to a second marker, wherein the second structure is connected to a second tag; and (f) detecting the second tag.

In some aspects, the signal of the first tag is reduced by greater than 50%. In other aspects, the contacting of step b is achieved by flowing a fluid comprising the first structure through a channel that is in fluid communication with the micro-cavities or micro-patch. In further aspects, following the contacting step of step (b), the method further comprises: contacting the analyte with a wash buffer. In still further aspects, the analytes are cells. In some aspects, the analytes are held in a fixed position within the micro-cavities by a force generated by fluid flow, gravity, or adhesive forces. In other aspects, each analyte is connected to a micro-cavity or micro-patch through a molecular interaction. In further aspects, each analyte is connected to a micro-cavity through a non-covalent bond. In still further aspects, the non-covalent bond is a van der Waals interaction, electrostatic bond, hydrophobic bond or non-specific adsorption.

In various aspects, devices are provided for detecting a particle in a fluid sample, the devices comprising: (a) a microfluidic chip comprising at least one sample input channel, at least one directional flow channel, and at least two output channels, wherein the at least one directional flow channel intersects the sample input channel; (b) an electro-actuated valve that is located on a device that is not part of the microfluidic chip, wherein the electro-actuated valve controls the flow of a liquid by controlling an input channel that intersects at least one directional flow channel or at least one of the at least two output channels; (c) at least one detector capable of detecting one or more analytes in an aliquot of the fluid sample; and (d) a digital processor capable of assigning a value to the aliquot based on the presence, absence, identity, composition, or quantity of analytes in the aliquot, wherein the digital processor is in communication with the detector and the electro-actuated valve. In some aspects, the electro-actuated valve is a solenoid valve. In other aspects, the electro-actuated valve controls the flow of the liquid in at least one directional flow channel.

In further aspects, the electro-actuated valve is normally closed and wherein the electro-activated valve opens after receiving a signal from the computer. In still further aspects, the electro-actuated valve is normally open and wherein the electro-activated valve closes after receiving a signal from the computer. In some aspects, the at least one directional flow channel comprises at least two ports and wherein the electro-actuated valve controls the flow of fluid through one of the ports. In other aspects, the device comprises a second detector. In further aspects, at least one of the output channels is fluidly connected to a filter.

In various aspects, methods are provided for isolating an aliquot of a fluid sample within a microfluidic chip, wherein the aliquot comprises a rare particle, the methods comprising the steps of: (a) detecting the presence or absence of the rare particle in the aliquot; (b) assigning a value to the aliquot based on the presence or absence of the rare particle; and (c) directing the flow of the aliquot based on the assigned value by opening an electro-actuated valve, wherein the electro-actuated valve is located on a device that is external to the microfluidic chip.

In some aspects, the microfluidic chip comprises a sample input channel, at least two output channels, and at least one directional flow channel, and wherein the electro-actuated valve controls the flow of fluid within the directional flow channel.

In various aspects, devices are provided for detecting a rare particle in a fluid sample, the device comprising: (a) at least a first sample input channel; (b) at least two output channels, wherein at least one of the two output channels is fluidly connected with an array of micro-apertures; (c) at least one detector capable of detecting one or more rare particles in an aliquot of the fluid sample; and (d) a mechanism for sorting the one or more rare particles by directing the flow of aliquots containing the one or more rare particles through a first output channel.

In some aspects, the mechanism directs the flow of the aliquots into a second output channel if the aliquot does not contain a rare particle. In some aspects, the array of apertures is disposed between the first sample input channel and the at least two output channels. In some aspects, the array of apertures is in the same plane as the first sample input channel and the output channels. In some aspects, the array of apertures is configured so that the rare particles cannot pass through the apertures but at least one other particle is capable of passing through the apertures. In some aspects, the array of apertures comprises greater than 1000 apertures. In some aspects, the mechanism for sorting the rare particles comprises an electrode, a magnetic element, an acoustic element, or an electro-actuated element. In some aspects, the detector is selected from the group consisting of a camera, an electron multiplier, a charge-coupled device (CCD) image sensor, a photomultiplier tube (PMT), an avalanche photodiode (APD), a single-photon avalanche diode (SPAD), a silicon photomultiplier (SiPM), and a complementary metal oxide semiconductor (CMOS) image sensor. In some aspects, the electro-actuated valve directly controls the flow of a liquid in at least one directional flow channel. In some aspects, the electro-actuated valve directly controls the flow of a liquid in a channel that feeds into at least one directional flow channel. In some aspects, the electro-actuated valve directly controls the flow of a liquid in only one directional flow channel. In some aspects, the electro-actuated valve directly controls the flow of a liquid in one of the at least two output channels. In some aspects, the electro-actuated valve directly controls the flow of a liquid in a channel that feeds into one of the at least two output channels. In some aspects, the at least one directional flow channel intersects the at least two output channels at one or more junctions. In some aspects, the device comprises a detector. In some aspects, the device comprises a confirmatory laser. In some aspects, the detector is located on at least one channel that is not an output channel. In some aspects, the confirmatory laser is located on at least one channel that is not an input channel. In some aspects, the electro-actuated valve is a piezo-electric valve.

What is claimed is:

1. A system for detecting a particle in a fluid sample, the system comprising:
   a microfluidic chip comprising:
      at least one sample input channel;
      at least one directional flow channel; and
      at least two output channels, wherein the at least one directional flow channel intersects the at least one sample input channel;
   an electro-actuated valve disposed on a device that is not part of the microfluidic chip, wherein the electro-actuated valve controls flow of a fluid by controlling the at least one directional flow channel;
   at least one detector capable of detecting one or more analytes in an aliquot of the fluid sample;
   a source of radiation;
   a source of light; and
   a controller operatively coupled to the electro-actuated valve, the at least one detector, the source of radiation, and the source of light, wherein the controller is programmed containing logic that when executed causes the system to perform operations including:
      illuminating the aliquot with the source of radiation;
      detecting a first signal from a first tag with the at least one detector, wherein the first tag is connected to a first structure, and wherein the first structure is configured to bind to a first marker;
      assigning a value to the aliquot based on the first signal;
      reducing, with light from the source of light, a level of the first signal of the first tag;
      contacting the one or more analytes with a second structure configured to bind to a second marker, wherein the second structure is connected to a second tag; and
      detecting the second tag.

2. The system of claim 1, further comprising a chamber in fluidic communication with an output channel of the at least two output channels, wherein the controller further includes logic that when executed causes the system to perform operations including:
   partitioning, with the electro-actuated valve, the aliquot in the chamber based on the value.

3. The system of claim 2, wherein the chamber is enclosed by walls.

4. The system of claim 1, further comprising an in-line staining and washing system in fluidic communication with a source of the second tag and in selective fluidic communication with the at least one directional flow channel.

5. The system of claim 1, further comprising a filter element configured so that a rare cell cannot pass through the filter element.

6. The system of claim 5, wherein the filter element comprises an array of apertures in fluidic communication with at least an output channel of the at least two output channels.

7. The system of claim 1, wherein the electro-actuated valve is a solenoid valve.

8. The system of claim 1, wherein the controller further includes logic that, when executed, is programmed to cause the system to perform operations including:
   contacting the aliquot with the first structure configured to bind to the first marker.

9. The system of claim 1, wherein the electro-actuated valve is normally closed, and wherein the electro-actuated valve opens after receiving a signal from the controller.

10. The system of claim 1, wherein the electro-actuated valve is normally open, and wherein the electro-actuated valve closes after receiving a signal from the controller.

11. The system of claim 1, wherein the at least one directional flow channel comprises at least two ports, and wherein the electro-actuated valve controls the flow of fluid through a port of the at least two ports.

12. The system of claim 1, wherein the electro-actuated valve directly controls flow of a fluid in the at least one directional flow channel.

13. The system of claim 1, wherein the electro-actuated valve directly controls flow of a fluid in a channel that feeds into the at least one directional flow channel.

14. The system of claim 1, wherein the electro-actuated valve directly controls flow of a fluid in only the at least one directional flow channel.

15. The system of claim 1, wherein the electro-actuated valve directly controls flow of a fluid in an output channel of the at least two output channels.

16. The system of claim 1, wherein the electro-actuated valve directly controls the flow of a fluid in a channel that feeds into an output channel of the at least two output channels.

17. The system of claim 1, wherein the electro-actuated valve is a piezo-electric valve.

18. The system of claim 1, wherein the at least one directional flow channel intersects an output channel of the at least two output channels at a junction.

19. The system of claim 1, wherein the at least one detector is located on at least one channel that is not an output channel of the at least two output channels.

20. The system of claim 1, wherein the device comprises a confirmatory laser, wherein the confirmatory laser is configured to illuminate at least one channel that is not the at least one sample input channel.

* * * * *